United States Patent
Fortson

(10) Patent No.: US 8,663,252 B2
(45) Date of Patent: Mar. 4, 2014

(54) SUTURING DEVICES AND METHODS

(75) Inventor: Aaron M. Fortson, Fremont, CA (US)

(73) Assignee: Abbott Cardiovascular Systems, Inc., Santa Clara, CA (US)

(*) Notice: Subject to any disclaimer, the term of this patent is extended or adjusted under 35 U.S.C. 154(b) by 394 days.

(21) Appl. No.: 12/873,728

(22) Filed: Sep. 1, 2010

(65) Prior Publication Data

US 2012/0053600 A1    Mar. 1, 2012

(51) Int. Cl.
*A61B 17/04* (2006.01)
*A61B 17/12* (2006.01)

(52) U.S. Cl.
USPC .......................................................... 606/145

(58) Field of Classification Search
USPC ......................................... 606/139, 144–150
See application file for complete search history.

(56) References Cited

U.S. PATENT DOCUMENTS

| | | | |
|---|---|---|---|
| 312,408 A | 2/1885 | Wackerhagen |
| 597,165 A | 1/1898 | Hall |
| 659,422 A | 10/1900 | Shidler |
| 989,231 A | 4/1911 | Davis |
| 1,574,362 A | 9/1922 | Callahan |
| 1,625,602 A | 4/1927 | Gould et al. |
| 1,940,351 A | 3/1933 | Howard |
| 2,012,776 A | 8/1935 | Roeder |
| 2,131,321 A | 10/1937 | Hart |
| 2,127,903 A | 8/1938 | Bowen |
| 2,371,978 A | 3/1945 | Perham |
| 2,397,823 A | 4/1946 | Walter |
| RE22,857 E | 3/1947 | Ogburn |
| 2,595,086 A | 11/1948 | Larzelere |
| 2,588,589 A | 3/1952 | Tauber |
| 2,646,045 A | 7/1953 | Priestley |
| 2,692,599 A | 10/1954 | Creelman |
| 2,941,489 A | 6/1960 | Fischbein |
| 2,959,172 A | 11/1960 | Held |
| 3,033,156 A | 5/1962 | Verlish |
| 3,104,666 A | 9/1963 | Hale et al. |
| 3,197,102 A | 7/1965 | Bates et al. |

(Continued)

FOREIGN PATENT DOCUMENTS

| | | |
|---|---|---|
| DE | 912619 | 5/1954 |
| DE | 4210724 | 7/1993 |

(Continued)

OTHER PUBLICATIONS

Issue Notification, U.S. Appl. No. 12/257,127, mailed Jan. 9, 2013.

(Continued)

*Primary Examiner* — Melanie Tyson
(74) *Attorney, Agent, or Firm* — Workman Nydegger; Randy Shen

(57) ABSTRACT

A surgical device for suturing body lumen is described, as well as methods for suturing tissue employing the surgical device. The device can include a body having a shaft and a foot for insertion into an opening in a body lumen. The body can include tissue ports between the shaft and the foot configured to receive tissue of the body lumen surrounding the opening. The foot can include a suture secured to needle capture devices. Needle can be advanced within the shaft, through tissue within the tissue ports, and into the needle capture devices. The needle capture devices cuffs can then be withdrawn, thereby harvesting the suture, which can then be used to close the opening in the body lumen.

18 Claims, 28 Drawing Sheets

(56) References Cited

U.S. PATENT DOCUMENTS

| | | |
|---|---|---|
| 3,359,983 A | 12/1967 | Northey |
| 3,413,397 A | 11/1968 | Bierbaum et al. |
| 3,422,181 A | 1/1969 | Chirgwin, Jr. |
| 3,470,875 A | 10/1969 | Johnson |
| 3,485,234 A | 12/1969 | Stevens |
| 3,587,115 A | 6/1971 | Shiley |
| 3,630,205 A | 12/1971 | Listner |
| 3,653,388 A | 4/1972 | Tenckhoff |
| 3,665,926 A | 5/1972 | Flores |
| 3,776,237 A | 12/1973 | Hill et al. |
| 3,802,438 A | 4/1974 | Wolvek |
| 3,820,544 A | 6/1974 | Semm |
| 3,840,017 A | 10/1974 | Violante |
| 3,874,388 A | 4/1975 | King et al. |
| 3,878,848 A | 4/1975 | Hiebert |
| 3,918,455 A | 11/1975 | Coplan |
| 3,926,194 A | 12/1975 | Greenberg et al. |
| 3,939,820 A | 2/1976 | Grayzel |
| 3,985,138 A | 10/1976 | Jarvik |
| 4,018,228 A | 4/1977 | Goosen |
| 4,069,825 A | 1/1978 | Akiyama |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,168,073 A | 9/1979 | LaRue |
| 4,182,339 A | 1/1980 | Hardy, Jr. |
| 4,185,636 A | 1/1980 | Gabbay et al. |
| 4,216,776 A | 8/1980 | Downie et al. |
| 4,217,665 A | 8/1980 | Bex et al. |
| 4,235,177 A | 11/1980 | Arbuckle |
| 4,235,238 A | 11/1980 | Ogiu et al. |
| 4,316,469 A | 2/1982 | Kapitanov |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,469,101 A | 9/1984 | Coleman et al. |
| 4,492,229 A | 1/1985 | Grunwald |
| 4,493,323 A | 1/1985 | Albright et al. |
| 4,553,543 A | 11/1985 | Amarasinghe |
| 4,586,614 A | 5/1986 | Ger |
| 4,587,969 A | 5/1986 | Gillis |
| 4,596,559 A | 6/1986 | Fleischhacker |
| 4,610,248 A | 9/1986 | Rosenberg |
| 4,629,450 A | 12/1986 | Suzuki et al. |
| 4,651,733 A | 3/1987 | Mobin-Uddin |
| 4,655,211 A | 4/1987 | Sakamoto et al. |
| 4,702,250 A | 10/1987 | Orvil et al. |
| 4,723,549 A | 2/1988 | Wholey et al. |
| 4,738,666 A | 4/1988 | Fuqua |
| 4,744,364 A | 5/1988 | Kensey |
| 4,748,982 A | 6/1988 | Horzewski et al. |
| 4,782,954 A | 11/1988 | Reynolds |
| 4,803,984 A | 2/1989 | Narayanan et al. |
| 4,836,205 A | 6/1989 | Barrett |
| 4,845,851 A | 7/1989 | Warthen |
| 4,848,341 A | 7/1989 | Ahmad |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,917,089 A | 4/1990 | Sideris |
| 4,926,860 A | 5/1990 | Stice et al. |
| 4,929,246 A | 5/1990 | Sinofsky |
| 4,935,027 A | 6/1990 | Yoon |
| 4,950,285 A | 8/1990 | Wilk |
| 4,957,498 A | 9/1990 | Caspari et al. |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,041,129 A | 8/1991 | Hayhurst et al. |
| 5,047,039 A | 9/1991 | Avant et al. |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,080,664 A | 1/1992 | Jain |
| 5,100,419 A | 3/1992 | Ehlers |
| 5,100,422 A | 3/1992 | Berguer et al. |
| 5,100,432 A | 3/1992 | Matsutani |
| 5,108,421 A | 4/1992 | Fowler |
| 5,109,780 A | 5/1992 | Slouf et al. |
| 5,129,882 A | 7/1992 | Weldon et al. |
| 5,129,912 A | 7/1992 | Noda et al. |
| 5,129,913 A | 7/1992 | Ruppert |
| 5,144,961 A | 9/1992 | Chen et al. |
| 5,147,373 A | 9/1992 | Ferzli |
| 5,156,788 A | 10/1992 | Chesterfield et al. |
| 5,160,339 A | 11/1992 | Chen et al. |
| 5,163,946 A | 11/1992 | Li |
| 5,169,041 A | 12/1992 | Tan |
| 5,171,251 A | 12/1992 | Bregen et al. |
| 5,176,691 A | 1/1993 | Pierce |
| 5,178,629 A | 1/1993 | Kammerer |
| 5,192,294 A | 3/1993 | Blake, III |
| 5,192,301 A | 3/1993 | Kamiya et al. |
| 5,192,302 A | 3/1993 | Kensey et al. |
| 5,201,744 A | 4/1993 | Jones |
| 5,207,703 A | 5/1993 | Jain |
| 5,211,650 A | 5/1993 | Noda |
| 5,217,470 A | 6/1993 | Weston |
| 5,217,485 A | 6/1993 | Liu et al. |
| 5,219,358 A | 6/1993 | Bendel et al. |
| 5,222,974 A | 6/1993 | Kensey et al. |
| 5,234,443 A | 8/1993 | Phan et al. |
| 5,234,445 A | 8/1993 | Walker et al. |
| 5,237,985 A | 8/1993 | Hodgson et al. |
| 5,242,427 A | 9/1993 | Bilweis |
| 5,250,033 A | 10/1993 | Evans et al. |
| 5,250,053 A | 10/1993 | Snyder |
| 5,250,054 A | 10/1993 | Li |
| 5,254,105 A | 10/1993 | Haaga |
| 5,254,113 A | 10/1993 | Wilk |
| 5,254,126 A | 10/1993 | Filipi et al. |
| 5,258,003 A | 11/1993 | Ciaglia et al. |
| 5,259,846 A | 11/1993 | Granger et al. |
| 5,275,616 A | 1/1994 | Fowler |
| 5,279,311 A | 1/1994 | Snyder |
| 5,281,236 A | 1/1994 | Bognato et al. |
| 5,281,237 A | 1/1994 | Gimpelson |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,290,310 A | 3/1994 | Makower et al. |
| 5,292,309 A | 3/1994 | Van Tassel et al. |
| 5,292,327 A | 3/1994 | Dodd et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway et al. |
| 5,304,185 A | 4/1994 | Taylor |
| 5,306,254 A | 4/1994 | Nash et al. |
| 5,312,024 A | 5/1994 | Grant et al. |
| 5,312,423 A | 5/1994 | Rosenbluth et al. |
| 5,318,578 A | 6/1994 | Hasson |
| 5,320,629 A | 6/1994 | Noda et al. |
| 5,320,632 A | 6/1994 | Heidmueller |
| 5,330,445 A | 7/1994 | Haaga |
| 5,330,491 A | 7/1994 | Walker et al. |
| 5,334,217 A | 8/1994 | Das |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,353,974 A | 10/1994 | Maurizio |

(56) References Cited

U.S. PATENT DOCUMENTS

| | | |
|---|---|---|
| 5,354,312 A | 10/1994 | Brinkerhoff et al. |
| 5,364,407 A | 11/1994 | Poll |
| 5,364,408 A | 11/1994 | Gordon |
| 5,368,595 A | 11/1994 | Lewis |
| 5,368,601 A | 11/1994 | Sauer et al. |
| 5,374,275 A | 12/1994 | Bradley et al. |
| 5,374,278 A | 12/1994 | Chesterfield et al. |
| 5,376,096 A | 12/1994 | Foster |
| 5,383,896 A | 1/1995 | Gershony et al. |
| 5,383,905 A | 1/1995 | Golds et al. |
| 5,385,569 A | 1/1995 | Swor |
| 5,387,221 A | 2/1995 | Bisgaard |
| 5,387,227 A | 2/1995 | Grice |
| 5,391,176 A | 2/1995 | de la Torre |
| 5,391,182 A | 2/1995 | Chin |
| 5,395,332 A | 3/1995 | Ressemann et al. |
| 5,395,349 A | 3/1995 | Quiachon et al. |
| 5,397,310 A | 3/1995 | Chu et al. |
| 5,397,325 A | 3/1995 | Delia Badia et al. |
| 5,397,326 A | 3/1995 | Mangum |
| 5,403,329 A | 4/1995 | Hinchcliffe |
| 5,403,331 A | 4/1995 | Chesterfield et al. |
| 5,403,338 A | 4/1995 | Milo |
| 5,405,352 A | 4/1995 | Weston |
| 5,411,481 A | 5/1995 | Allen et al. |
| 5,413,571 A | 5/1995 | Katsaros et al. |
| 5,417,684 A | 5/1995 | Jackson et al. |
| 5,417,699 A | 5/1995 | Klein et al. |
| 5,419,765 A | 5/1995 | Weldon et al. |
| 5,425,705 A | 6/1995 | Evard et al. |
| 5,425,737 A | 6/1995 | Burbank et al. |
| 5,425,740 A | 6/1995 | Hutchinson, Jr. |
| 5,431,666 A | 7/1995 | Sauer et al. |
| 5,433,700 A | 7/1995 | Peters |
| 5,452,733 A | 9/1995 | Sterman et al. |
| 5,454,822 A | 10/1995 | Schob et al. |
| 5,454,834 A | 10/1995 | Boebel et al. |
| 5,458,574 A | 10/1995 | Machold et al. |
| 5,462,560 A | 10/1995 | Stevens |
| 5,462,561 A | 10/1995 | Voda |
| 5,464,426 A | 11/1995 | Bonutti |
| 5,466,241 A | 11/1995 | Leroy et al. |
| 5,470,338 A | 11/1995 | Whitfield et al. |
| 5,474,568 A | 12/1995 | Scott |
| 5,476,469 A | 12/1995 | Hathaway et al. |
| 5,476,470 A | 12/1995 | Fitzgibbons, Jr. |
| 5,478,309 A | 12/1995 | Sweezer et al. |
| 5,478,353 A | 12/1995 | Yoon |
| 5,480,407 A | 1/1996 | Wan et al. |
| 5,486,190 A | 1/1996 | Green |
| 5,489,295 A | 2/1996 | Piplani et al. |
| 5,496,332 A | 3/1996 | Sierra et al. |
| 5,507,744 A | 4/1996 | Tay et al. |
| 5,507,755 A | 4/1996 | Gresl et al. |
| 5,507,757 A | 4/1996 | Sauer et al. |
| 5,507,758 A | 4/1996 | Thomason et al. |
| 5,509,902 A | 4/1996 | Raulerson |
| 5,520,655 A | 5/1996 | Davila et al. |
| 5,520,665 A | 5/1996 | Fleetwood |
| 5,520,691 A | 5/1996 | Branch |
| 5,520,702 A | 5/1996 | Sauer et al. |
| 5,527,321 A | 6/1996 | Hinchliffe |
| 5,527,322 A | 6/1996 | Klein et al. |
| D372,310 S | 7/1996 | Hartnett |
| 5,531,700 A | 7/1996 | Moore et al. |
| 5,536,273 A | 7/1996 | Lehrer |
| 5,540,701 A | 7/1996 | Sharkey et al. |
| 5,540,703 A | 7/1996 | Barker, Jr. et al. |
| 5,540,704 A | 7/1996 | Gordon et al. |
| 5,545,171 A | 8/1996 | Sharkey et al. |
| 5,545,178 A | 8/1996 | Kensey et al. |
| 5,545,180 A | 8/1996 | Le et al. |
| 5,549,618 A | 8/1996 | Fleenor et al. |
| 5,549,631 A | 8/1996 | Bonutti |
| 5,554,162 A | 9/1996 | DeLange |
| 5,562,684 A | 10/1996 | Kammerer |
| 5,562,686 A | 10/1996 | Sauer et al. |
| 5,562,688 A | 10/1996 | Riza |
| 5,562,728 A | 10/1996 | Lazarus et al. |
| 5,567,435 A | 10/1996 | Hubbell et al. |
| 5,569,269 A | 10/1996 | Hart et al. |
| 5,569,271 A | 10/1996 | Hoel |
| 5,571,120 A | 11/1996 | Yoon |
| 5,573,540 A | 11/1996 | Yoon |
| 5,584,842 A | 12/1996 | Fogarty et al. |
| 5,591,177 A | 1/1997 | Lehrer |
| 5,591,179 A | 1/1997 | Edelstein |
| 5,591,206 A | 1/1997 | Moufarrege |
| 5,593,421 A | 1/1997 | Bauer |
| 5,601,572 A | 2/1997 | Middleman et al. |
| 5,603,718 A | 2/1997 | Xu |
| 5,607,435 A | 3/1997 | Sachdeva et al. |
| 5,609,597 A | 3/1997 | Lehrer |
| 5,611,794 A | 3/1997 | Sauer et al. |
| 5,613,974 A | 3/1997 | Andreas et al. |
| 5,613,975 A | 3/1997 | Christy |
| 5,624,446 A | 4/1997 | Harryman, II |
| 5,626,588 A | 5/1997 | Sauer et al. |
| 5,643,289 A | 7/1997 | Sauer et al. |
| 5,643,295 A | 7/1997 | Yoon |
| 5,643,318 A | 7/1997 | Tsukernik et al. |
| 5,649,959 A | 7/1997 | Hannam et al. |
| 5,662,664 A | 9/1997 | Gordon et al. |
| 5,669,917 A | 9/1997 | Sauer et al. |
| 5,676,689 A | 10/1997 | Kensey et al. |
| 5,700,273 A | 12/1997 | Buelna et al. |
| 5,707,379 A | 1/1998 | Fleenor et al. |
| 5,713,910 A | 2/1998 | Gordon et al. |
| 5,716,369 A | 2/1998 | Riza |
| 5,720,574 A | 2/1998 | Barella |
| 5,720,757 A | 2/1998 | Hathaway et al. |
| 5,722,981 A | 3/1998 | Stevens |
| 5,725,552 A | 3/1998 | Kotula et al. |
| 5,728,109 A | 3/1998 | Schulze et al. |
| 5,728,114 A | 3/1998 | Evans et al. |
| 5,728,133 A | 3/1998 | Kontos |
| 5,728,151 A | 3/1998 | Garrison et al. |
| 5,741,276 A | 4/1998 | Poloyko et al. |
| 5,741,280 A | 4/1998 | Fleenor |
| 5,746,755 A | 5/1998 | Wood et al. |
| 5,749,890 A | 5/1998 | Shaknovich |
| 5,755,727 A | 5/1998 | Kontos |
| 5,759,188 A | 6/1998 | Yoon |
| 5,766,183 A | 6/1998 | Sauer |
| 5,766,186 A | 6/1998 | Faraz et al. |
| 5,766,217 A | 6/1998 | Christy |
| 5,769,862 A | 6/1998 | Kammerer et al. |
| 5,779,719 A | 7/1998 | Klein et al. |
| 5,782,860 A | 7/1998 | Epstein et al. |
| 5,782,861 A | 7/1998 | Cragg et al. |
| 5,792,151 A | 8/1998 | Heck et al. |
| 5,792,152 A | 8/1998 | Klein et al. |
| 5,797,928 A | 8/1998 | Kogasaka |
| 5,797,929 A | 8/1998 | Andreas et al. |
| 5,799,661 A | 9/1998 | Boyd et al. |
| 5,810,849 A | 9/1998 | Kontos |
| 5,810,850 A | 9/1998 | Hathaway et al. |
| 5,814,069 A | 9/1998 | Schulze et al. |
| 5,817,113 A | 10/1998 | Gifford, III et al. |
| 5,820,631 A | 10/1998 | Nobles |
| 5,824,010 A | 10/1998 | McDonald |
| 5,824,111 A | 10/1998 | Schall et al. |
| 5,830,125 A | 11/1998 | Scribner et al. |
| 5,836,955 A | 11/1998 | Buelna et al. |
| 5,836,956 A | 11/1998 | Buelna et al. |
| 5,846,253 A | 12/1998 | Buelna et al. |
| 5,848,714 A | 12/1998 | Robson et al. |
| 5,855,585 A | 1/1999 | Kontos |
| 5,860,963 A | 1/1999 | Azam et al. |
| 5,860,990 A | 1/1999 | Nobles et al. |
| 5,860,991 A | 1/1999 | Klein et al. |
| 5,861,005 A | 1/1999 | Kontos |
| 5,871,490 A | 2/1999 | Schulze et al. |
| 5,871,502 A | 2/1999 | Suryadevara |

(56) References Cited

U.S. PATENT DOCUMENTS

| | | | |
|---|---|---|---|
| 5,873,876 | A | 2/1999 | Christy |
| 5,876,411 | A | 3/1999 | Kontos |
| 5,897,487 | A | 4/1999 | Ouchi |
| 5,897,564 | A | 4/1999 | Schulze et al. |
| 5,902,311 | A | 5/1999 | Andreas et al. |
| 5,904,597 | A | 5/1999 | Doi et al. |
| 5,904,690 | A | 5/1999 | Middleman et al. |
| 5,904,697 | A | 5/1999 | Gifford, III et al. |
| 5,906,631 | A | 5/1999 | Imran |
| 5,919,207 | A | 7/1999 | Taheri |
| 5,921,994 | A | 7/1999 | Andreas et al. |
| 5,928,266 | A | 7/1999 | Kontos |
| 5,951,590 | A | 9/1999 | Goldfarb |
| 5,954,732 | A | 9/1999 | Hart et al. |
| 5,957,936 | A | 9/1999 | Yoon et al. |
| 5,957,937 | A | 9/1999 | Yoon |
| 5,957,938 | A | 9/1999 | Zhu et al. |
| 5,964,773 | A | 10/1999 | Greenstein |
| 5,964,782 | A | 10/1999 | Lafontaine et al. |
| 5,972,030 | A | 10/1999 | Garrison et al. |
| 5,976,161 | A | 11/1999 | Kirsch et al. |
| 5,980,539 | A | 11/1999 | Kontos |
| 5,997,555 | A | 12/1999 | Kontos |
| 6,001,109 | A | 12/1999 | Kontos |
| 6,022,372 | A | 2/2000 | Kontos |
| 6,024,747 | A | 2/2000 | Kontos |
| 6,036,699 | A | 3/2000 | Andreas et al. |
| 6,042,601 | A | 3/2000 | Smith |
| 6,048,351 | A | 4/2000 | Gordon et al. |
| 6,048,354 | A | 4/2000 | Lawrence |
| 6,048,357 | A | 4/2000 | Kontos |
| 6,068,603 | A | 5/2000 | Suzuki |
| 6,077,276 | A | 6/2000 | Kontos |
| 6,077,279 | A | 6/2000 | Kontos |
| 6,117,144 | A | 9/2000 | Nobles et al. |
| 6,117,145 | A | 9/2000 | Wood et al. |
| 6,126,675 | A | 10/2000 | Shchervinsky et al. |
| 6,132,439 | A | 10/2000 | Kontos |
| 6,132,440 | A | 10/2000 | Hathaway et al. |
| 6,136,010 | A | 10/2000 | Modesitt et al. |
| 6,139,556 | A | 10/2000 | Kontos |
| 6,152,936 | A | 11/2000 | Christy et al. |
| 6,165,183 | A | 12/2000 | Kuehn et al. |
| 6,165,204 | A | 12/2000 | Levinson et al. |
| 6,190,396 | B1 | 2/2001 | Whitin et al. |
| 6,197,042 | B1 | 3/2001 | Ginn et al. |
| 6,206,893 | B1 | 3/2001 | Klein et al. |
| 6,206,895 | B1 | 3/2001 | Levinson |
| 6,245,079 | B1 | 6/2001 | Nobles et al. |
| 6,248,124 | B1 | 6/2001 | Pedros et al. |
| 6,296,657 | B1 | 10/2001 | Brucker |
| 6,348,059 | B1 | 2/2002 | Hathaway et al. |
| 6,355,050 | B1 | 3/2002 | Andreas et al. |
| 6,358,258 | B1 | 3/2002 | Arcia et al. |
| 6,395,015 | B1 | 5/2002 | Borst et al. |
| 6,428,472 | B1 | 8/2002 | Haas |
| 6,428,549 | B1 | 8/2002 | Kontos |
| 6,436,109 | B1 | 8/2002 | Kontos |
| 6,443,963 | B1 | 9/2002 | Baldwin et al. |
| 6,451,031 | B1 | 9/2002 | Kontos |
| 6,511,489 | B2 | 1/2003 | Field et al. |
| 6,517,553 | B2 | 2/2003 | Klein et al. |
| 6,533,812 | B2 | 3/2003 | Swanson et al. |
| 6,551,330 | B1 | 4/2003 | Bain et al. |
| 6,558,399 | B1 | 5/2003 | Isbell et al. |
| 6,562,052 | B2 | 5/2003 | Nobles et al. |
| 6,569,185 | B2 | 5/2003 | Ungs |
| 6,572,629 | B2 | 6/2003 | Kalloo et al. |
| 6,610,072 | B1 | 8/2003 | Christy et al. |
| 6,623,509 | B2 | 9/2003 | Ginn |
| 6,623,510 | B2 | 9/2003 | Carley et al. |
| 6,632,237 | B2 | 10/2003 | Ben-David et al. |
| 6,641,592 | B1 | 11/2003 | Sauer et al. |
| 6,663,655 | B2 | 12/2003 | Ginn et al. |
| 6,676,685 | B2 | 1/2004 | Pedros et al. |
| 6,695,867 | B2 | 2/2004 | Ginn et al. |
| 6,716,228 | B2 | 4/2004 | Tal |
| 6,743,195 | B2 | 6/2004 | Zucker |
| 6,743,259 | B2 | 6/2004 | Ginn |
| 6,749,621 | B2 | 6/2004 | Pantages et al. |
| 6,749,622 | B2 | 6/2004 | McGuckin, Jr. et al. |
| 6,837,906 | B2 | 1/2005 | Ginn |
| 6,846,319 | B2 | 1/2005 | Ginn et al. |
| 6,890,343 | B2 | 5/2005 | Ginn et al. |
| 6,896,692 | B2 | 5/2005 | Ginn et al. |
| 6,911,034 | B2 | 6/2005 | Nobles et al. |
| 6,939,357 | B2 | 9/2005 | Navarro et al. |
| 6,964,668 | B2 | 11/2005 | Modesitt et al. |
| 6,969,397 | B2 | 11/2005 | Ginn |
| 7,001,400 | B1 | 2/2006 | Modesitt et al. |
| 7,029,480 | B2 | 4/2006 | Klein et al. |
| 7,029,481 | B1 | 4/2006 | Burdulis, Jr. et al. |
| 7,048,747 | B2 | 5/2006 | Arcia et al. |
| 7,063,710 | B2 | 6/2006 | Takamoto et al. |
| 7,083,635 | B2 | 8/2006 | Ginn |
| 7,108,710 | B2 | 9/2006 | Anderson |
| 7,112,225 | B2 | 9/2006 | Ginn |
| 7,160,309 | B2 | 1/2007 | Voss |
| 7,179,266 | B2 | 2/2007 | Kontos |
| 7,229,458 | B2 | 6/2007 | Boecker et al. |
| 7,235,087 | B2 | 6/2007 | Modesitt et al. |
| 7,316,704 | B2 | 1/2008 | Bagaoisan et al. |
| 7,326,230 | B2 | 2/2008 | Ravikumar |
| 7,331,979 | B2 | 2/2008 | Khosravi et al. |
| 7,335,220 | B2 | 2/2008 | Khosravi et al. |
| 7,361,183 | B2 | 4/2008 | Ginn |
| 7,361,185 | B2 | 4/2008 | O'Malley et al. |
| 7,377,927 | B2 | 5/2008 | Burdulis, Jr. et al. |
| 7,390,328 | B2 | 6/2008 | Modesitt |
| 7,393,363 | B2 | 7/2008 | Ginn |
| 7,442,198 | B2 | 10/2008 | Gellman et al. |
| 7,445,626 | B2 | 11/2008 | Songer et al. |
| 7,449,024 | B2 | 11/2008 | Stafford |
| 7,462,188 | B2 | 12/2008 | McIntosh |
| 7,753,923 | B2 | 7/2010 | St. Goar et al. |
| 7,837,696 | B2 | 11/2010 | Modesitt et al. |
| 7,842,047 | B2 | 11/2010 | Modesitt et al. |
| 7,842,048 | B2 | 11/2010 | Ma |
| 7,842,049 | B2 | 11/2010 | Voss |
| 7,846,170 | B2 | 12/2010 | Modesitt et al. |
| 7,850,701 | B2 | 12/2010 | Modesitt |
| 7,883,517 | B2 | 2/2011 | Pantages et al. |
| 8,038,688 | B2 | 10/2011 | Modesitt et al. |
| 8,048,092 | B2 | 11/2011 | Modesitt et al. |
| 8,057,491 | B2 | 11/2011 | Modesitt et al. |
| 8,083,754 | B2 | 12/2011 | Pantages et al. |
| 8,137,364 | B2 | 3/2012 | Zung et al. |
| 8,211,122 | B2 | 7/2012 | McIntosh |
| 2001/0046518 | A1 | 11/2001 | Sawhney |
| 2002/0045908 | A1 | 4/2002 | Nobles et al. |
| 2002/0095164 | A1 | 7/2002 | Andreas et al. |
| 2002/0099389 | A1 | 7/2002 | Michler et al. |
| 2002/0106409 | A1 | 8/2002 | Sawhney et al. |
| 2002/0177876 | A1 | 11/2002 | Roby et al. |
| 2003/0093093 | A1 | 5/2003 | Modesitt et al. |
| 2003/0195529 | A1 | 10/2003 | Takamoto et al. |
| 2004/0009205 | A1 | 1/2004 | Sawhney |
| 2004/0092964 | A1 | 5/2004 | Modesitt et al. |
| 2004/0093027 | A1 | 5/2004 | Fabisiak et al. |
| 2004/0097978 | A1 | 5/2004 | Modesitt et al. |
| 2004/0127940 | A1 | 7/2004 | Ginn et al. |
| 2004/0143290 | A1 | 7/2004 | Brightbill |
| 2004/0158127 | A1 | 8/2004 | Okada |
| 2004/0158287 | A1 | 8/2004 | Cragg et al. |
| 2004/0167511 | A1 | 8/2004 | Buehlmann et al. |
| 2004/0181238 | A1 | 9/2004 | Zarbatany et al. |
| 2004/0186487 | A1 | 9/2004 | Klein et al. |
| 2004/0191277 | A1 | 9/2004 | Sawhney et al. |
| 2004/0215232 | A1 | 10/2004 | Belhe et al. |
| 2004/0225301 | A1 | 11/2004 | Roop et al. |
| 2004/0267193 | A1 | 12/2004 | Bagaoisan et al. |
| 2004/0267308 | A1 | 12/2004 | Bagaoisan et al. |
| 2005/0070923 | A1 | 3/2005 | McIntosh |
| 2005/0075665 | A1 | 4/2005 | Brenzel et al. |

(56) References Cited

U.S. PATENT DOCUMENTS

| | | | |
|---|---|---|---|
| 2005/0085851 A1 | 4/2005 | Fiehler et al. | |
| 2005/0085854 A1 | 4/2005 | Ginn | |
| 2005/0085855 A1 | 4/2005 | Forsberg | |
| 2005/0121042 A1 | 6/2005 | Belhe et al. | |
| 2005/0149117 A1 | 7/2005 | Khosravi et al. | |
| 2005/0177189 A1 | 8/2005 | Ginn et al. | |
| 2005/0222614 A1 | 10/2005 | Ginn et al. | |
| 2005/0245876 A1 | 11/2005 | Khosravi et al. | |
| 2005/0267528 A1 | 12/2005 | Ginn et al. | |
| 2005/0273137 A1 | 12/2005 | Ginn | |
| 2006/0034930 A1 | 2/2006 | Khosravi et al. | |
| 2006/0047313 A1 | 3/2006 | Khanna et al. | |
| 2006/0100664 A1 | 5/2006 | Pai et al. | |
| 2006/0167477 A1 | 7/2006 | Arcia et al. | |
| 2006/0173469 A1 | 8/2006 | Klein | |
| 2006/0253037 A1 | 11/2006 | Ginn et al. | |
| 2006/0253072 A1 | 11/2006 | Pai et al. | |
| 2007/0005079 A1* | 1/2007 | Zarbatany et al. | 606/139 |
| 2007/0032801 A1 | 2/2007 | Pantages et al. | |
| 2007/0060950 A1 | 3/2007 | Khosravi et al. | |
| 2007/0123817 A1 | 5/2007 | Khosravi et al. | |
| 2007/0276410 A1 | 11/2007 | McIntosh | |
| 2007/0282354 A1 | 12/2007 | McIntosh | |
| 2008/0009794 A1 | 1/2008 | Bagaoisan et al. | |
| 2008/0065151 A1 | 3/2008 | Ginn | |
| 2008/0065152 A1 | 3/2008 | Carley | |
| 2008/0287967 A1 | 11/2008 | Andreas et al. | |
| 2008/0319458 A1 | 12/2008 | Reynolds | |
| 2009/0005793 A1 | 1/2009 | Pantages et al. | |
| 2009/0036906 A1* | 2/2009 | Stafford | 606/144 |
| 2009/0048615 A1 | 2/2009 | McIntosh | |
| 2009/0088779 A1 | 4/2009 | Zung et al. | |
| 2009/0157105 A1 | 6/2009 | Zung et al. | |
| 2011/0066184 A1 | 3/2011 | Modesitt et al. | |
| 2011/0071472 A1 | 3/2011 | Voss | |
| 2011/0071552 A1 | 3/2011 | Ma | |
| 2011/0071567 A1 | 3/2011 | Modesitt et al. | |
| 2011/0196387 A1 | 8/2011 | Pantages et al. | |
| 2012/0150201 A1 | 6/2012 | Pantages et al. | |
| 2012/0316579 A1 | 12/2012 | Ma | |
| 2013/0006277 A1 | 1/2013 | Stafford | |
| 2013/0012962 A1* | 1/2013 | Stone | 606/144 |
| 2013/0066340 A1 | 3/2013 | Pantages et al. | |
| 2013/0190781 A1 | 7/2013 | Fortson et al. | |

FOREIGN PATENT DOCUMENTS

| | | |
|---|---|---|
| DE | 9217932 | 7/1993 |
| DE | 4220283 | 12/1993 |
| DE | 10211360 | 10/2003 |
| EP | 0 140 557 | 5/1985 |
| EP | 0 207 545 | 1/1987 |
| EP | 0 474 887 | 3/1992 |
| EP | 0 478 358 | 4/1992 |
| EP | 0 478 887 | 4/1992 |
| EP | 0 542 126 | 5/1993 |
| EP | 0 568 098 | 11/1993 |
| EP | 0 589 409 | 3/1994 |
| EP | 0 624 343 | 11/1994 |
| EP | 0 669 101 | 8/1995 |
| EP | 0 669 102 | 8/1995 |
| EP | 0 669 103 | 8/1995 |
| EP | 0 684 012 | 11/1995 |
| EP | 0 812 571 | 12/1997 |
| EP | 0 941 698 | 9/1999 |
| FR | 1059544 | 3/1954 |
| FR | 2768324 | 3/1999 |
| JP | 51143386 | 11/1976 |
| JP | 5220794 | 2/1977 |
| JP | 2119866 | 5/1990 |
| JP | 542161 | 2/1993 |
| SU | 820810 | 4/1981 |
| SU | 993922 | 2/1983 |
| SU | 1093329 | 5/1984 |
| SU | 1174036 | 8/1985 |
| SU | 1544383 | 2/1990 |
| SU | 1648400 | 5/1991 |
| WO | WO 85/03858 | 9/1985 |
| WO | WO 01/35833 | 2/1994 |
| WO | WO 94/05213 | 3/1994 |
| WO | WO 94/13211 | 6/1994 |
| WO | WO 94/27503 | 12/1994 |
| WO | WO 94/28801 | 12/1994 |
| WO | WO 95/05121 | 2/1995 |
| WO | WO 95/13021 | 5/1995 |
| WO | WO 95/25468 | 9/1995 |
| WO | WO 95/35065 | 12/1995 |
| WO | WO 96/09006 | 3/1996 |
| WO | WO 97/00046 | 1/1997 |
| WO | WO 97/03613 | 2/1997 |
| WO | WO 97/07745 | 3/1997 |
| WO | WO 97/10764 | 3/1997 |
| WO | WO 97/13461 | 4/1997 |
| WO | WO 97/17901 | 5/1997 |
| WO | WO 97/20505 | 6/1997 |
| WO | WO 97/27897 | 8/1997 |
| WO | WO 98/04195 | 2/1998 |
| WO | WO 98/42262 | 10/1998 |
| WO | WO 99/47049 | 9/1999 |
| WO | WO 00/12013 | 3/2000 |
| WO | WO 00/51498 | 9/2000 |
| WO | WO 00/69342 | 11/2000 |
| WO | WO 01/19259 | 3/2001 |
| WO | WO 02/36021 | 5/2002 |
| WO | WO 02/062234 | 8/2002 |
| WO | WO 03/003925 | 1/2003 |
| WO | WO 03/094748 | 11/2003 |
| WO | WO 03/099134 | 12/2003 |
| WO | WO 2005/000126 | 1/2005 |
| WO | WO 2005/023119 | 3/2005 |
| WO | WO 2005/025430 | 3/2005 |
| WO | WO 2005/030060 | 4/2005 |
| WO | WO 2005/041782 | 5/2005 |
| WO | WO 2005/063129 | 7/2005 |
| WO | WO 2005/065549 | 7/2005 |
| WO | WO 2005/092204 | 10/2005 |
| WO | WO 2005/112782 | 12/2005 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/115901 | 11/2006 |
| WO | WO 2006/115904 | 11/2006 |
| WO | WO 2006/118877 | 11/2006 |
| WO | WO 2007/019016 | 2/2007 |
| WO | WO 2007/081836 | 7/2007 |

OTHER PUBLICATIONS

Notice of Allowance, U.S. Appl. No. 13/593,154, mailed Jan. 8, 2013.
Office Action, U.S. Appl. No. 12/334,077, mailed Jan. 16, 2013.
Office Action, U.S. Appl. No. 13/615,530, mailed Jan. 17, 2013.
Issue Notification, U.S. Appl. No. 12/247,012, mailed Mar. 27, 2013.
Issue Notification, U.S. Appl. No. 13/593,154, mailed Apr. 10, 2013.
U.S. Appl. No. 13/752,095, filed Jan. 28, 2013, McIntosh.
U.S. Appl. No. 60/506,536, filed Sep. 26, 2003, McIntosh.
U.S. Appl. No. 60/540,811, filed Jan. 30, 2004, McIntosh.
U.S. Appl. No. 60/946,063, filed Jun. 25, 2007, Reynolds.
U.S. Appl. No. 90/006,469, filed Nov. 29, 2002, Modesitt, et al.
US 5,820,544, 6/1974, Semm (withdrawn).
Cardiac Catheterization and Angiography, 3rd Ed., Lea N. ad Febiger, Philadelphia, pp. 1-49, 52-247. 1986.
Cardio-Thoracic Systems Prospectus dated Mar. 20, 1996. pp. 1-4, 25-40.
Datascope Corporation, Montvale, NJ, Nov. 1991; 1 PG, American Heart Assoc. Meeting, Anaheim.
Elgiloy Brochure, Jun. 23, 1959; Elgin National Watch Co., Elgin, IL.
Kensey Nash Corporation, Exton, PA, "The Hemostatic Puncture Closure Device", retrieved Oct. 23, 2007, 2 pages.
Laurus Medical Corporation, "Endoscopic Suturing Made Simple," The Laurus ND-2600 Needle Driver, Irvine, CA., Oct. 1994, 1 page.

(56) References Cited

OTHER PUBLICATIONS

Marshall, A.C. & Lock, J.E.; "Structural and compliant anatomy of the patent foramen ovale in patients undergoing transcatheter closure", Am. Heart Journ., 140(2):303-307, Aug. 2000.
Nakamura, S. et al., Techniques for Palmaz-Schatz Stent Deployment in Lesions With a Large Side Branch, Catheterization and Cardiovascular Diagnosis, 34: 353-361, 1995.
Product Brochure, "SuperStitch—Closure Made SimpleTM", Sutura, Inc. (2003).
Product Brochure, Laurus Medical Corporation, Irvine, CA "The Laurus In-Line Endoscopic Suturing Device" (Oct. 1994) 1 page.
Rema-Medizintechnik GmbH, Product Brochure entitled "REMA," Apr. 2001, 7 pages.
Serruys, PW et al., A Comparision of Balloon-Expandable-Stent Implantaion With Balloon Angioplasty in Patients With Coronary Artery Disease, New England Journal of Medicine, 331:489-495, 1994.
Taber's Cyclopedic Medical Dictionary, 18th Ed., p. 747, Feb. 1997.
Office Action, U.S. Appl. No. 07/989,611, mailed May 12, 1993.
Office Action, U.S. Appl. No. 07/989,611, mailed Aug. 1, 1994.
Notice of Allowance, U.S. Appl. No. 07/989,611, mailed Nov. 3, 1994.
Office Action, U.S. Appl. No. 08/148,809, mailed Sep. 16, 1994.
Office Action, U.S. Appl. No. 08/148,809, mailed May 30, 1995.
Notice of Allowance, U.S. Appl. No. 08/148,809, mailed Dec. 15, 1995.
Office Action, U.S. Appl. No. 08/252,124, mailed Jun. 5, 1995.
Office Action, U.S. Appl. No. 08/252,124, mailed Jan. 5, 1996.
Notice of Allowance, U.S. Appl. No. 08/252,124, mailed May 22, 1996.
Office Action, U.S. Appl. No. 08/259,410, mailed Feb. 2, 1995.
Office Action, U.S. Appl. No. 08/259,410, mailed Jun. 1, 1995.
Notice of Allowance, U.S. Appl. No. 08/259,410, mailed Feb. 6, 1998.
Office Action, U.S. Appl. No. 08/638076, mailed Jan. 21, 1997.
Notice of Allowance, U.S. Appl. No. 08/638,076, mailed Oct. 17, 1997.
Office Action, U.S. Appl. No. 08/824,031, mailed Mar. 16, 1998.
Office Action, U.S. Appl. No. 08/824,031, mailed Sep. 14, 1998.
Office Action, U.S. Appl. No. 08/824,031, mailed Apr. 13, 1999.
Notice of Allowance, U.S. Appl. No. 08/824,031, mailed Jul. 15, 1999.
Office Action, U.S. Appl. No. 08/883,246, mailed Jul. 23, 1998.
Office Action, U.S. Appl. No. 08/883,246, mailed Apr. 12, 1999.
Office Action, U.S. Appl. No. 08/883,246, mailed Oct. 13, 1999.
Office Action, U.S. Appl. No. 08/883,246, mailed Oct. 23, 2000.
Office Action, U.S. Appl. No. 08/883,246, mailed Jul. 11, 2001.
Notice of Allowance, U.S. Appl. No. 08/883,246, mailed Sep. 11, 2001.
Office Action, U.S. Appl. No. 09/057,108, mailed Jul. 10, 2000.
Notice of Allowance, U.S. Appl. No. 09/057,108, mailed Oct. 25, 2000.
Office Action, U.S. Appl. No. 09/262,402, mailed Mar. 29, 2000.
Notice of Allowance, U.S. Appl. No. 09/262,402, mailed May 30, 2000.
Office Action, U.S. Appl. No. 09/395,901, mailed Jun. 27, 2000.
Office Action, U.S. Appl. No. 09/395,901, mailed Nov. 6, 2000.
Notice of Allowance, U.S. Appl. No. 09/395,901, mailed Apr. 20, 2001.
Notice of Allowance, U.S. Appl. No. 09/395,901, mailed Sep. 10, 2001.
Office Action, U.S. Appl. No. 09/610,099, mailed Jul. 11, 2002.
Notice of Allowance, U.S. Appl. No. 09/610,099, mailed Dec. 24, 2002.
Office Action, U.S. Appl. No. 09/651,344, mailed Feb. 28, 2003.
Office Action, U.S. Appl. No. 09/651,344, mailed Nov. 7, 2003.
Notice of Allowance, U.S. Appl. No. 09/651,344, mailed Apr. 20, 2004.
Office Action, U.S. Appl. No. 09/707,746, mailed Feb. 16, 2005.
Office Action, U.S. Appl. No. 09/707,746, mailed Jul. 7, 2005.
Notice of Allowance, U.S. Appl. No. 09/707,746, mailed Nov. 15, 2005.
Office Action, U.S. Appl. No. 09/769,109, mailed Oct. 23, 2001.
Office Action, U.S. Appl. No. 09/769,109, mailed Jun. 17, 2002.
Notice of Allowance, U.S. Appl. No. 09/769,109, mailed Sep. 9, 2002.
Office Action, U.S. Appl. No. 09/988,541, mailed Mar. 17, 2004.
Office Action, U.S. Appl. No. 09/988,541, mailed Feb. 28, 2005.
Office Action, U.S. Appl. No. 09/988,541, mailed May 25, 2005.
Office Action, U.S. Appl. No. 09/988,541, mailed Aug. 24, 2005.
Office Action, U.S. Appl. No. 09/988,541, mailed Nov. 8, 2005.
Notice of Allowance, U.S. Appl. No. 09/988,541, mailed Dec. 13, 2005.
Office Action, U.S. Appl. No. 10/033,689, mailed Sep. 30, 2003.
Office Action, U.S. Appl. No. 10/152,272, mailed Jan. 24, 2005.
Notice of Allowance, U.S. Appl. No. 10/152,272, mailed May 13, 2005.
Office Action, U.S. Appl. No. 10/335,065, mailed Mar. 17, 2005.
Office Action, U.S. Appl. No. 10/335,065, mailed Jun. 10, 2005.
Notice of Allowance, U.S. Appl. No. 10/335,065, mailed Nov. 17, 2005.
Office Action, U.S. Appl. No. 10/335,147, mailed Dec. 13, 2005.
Office Action, U.S. Appl. No. 10/335,147, mailed Apr. 17, 2006.
Notice of Allowance, U.S. Appl. No. 10/335,147, mailed Oct. 4, 2006.
Office Action, U.S. Appl. No. 10/335,147, mailed Oct. 4, 2006.
Office Action, U.S. Appl. No. 10/357,984, mailed Mar. 16, 2006.
Office Action, U.S. Appl. No. 10/357,984, mailed Sep. 28, 2006.
Office Action, U.S. Appl. No. 10/357,984, mailed Mar. 23, 2007.
Office Action, U.S. Appl. No. 10/357,984 , mailed Nov. 14, 2007.
Office Action, U.S. Appl. No. 10/652,182, mailed Aug. 9, 2006.
Notice of Allowance, U.S. Appl. No. 10/652,182, mailed Feb. 22, 2007.
Office Action, U.S. Appl. No. 10/660,288, mailed Nov. 15, 2005.
Office Action, U.S. Appl. No. 10/660,288, mailed Mar. 9, 2006.
Office Action, U.S. Appl. No. 10/660,288, mailed Aug. 24, 2006.
Office Action, U.S. Appl. No. 10/660,288, mailed Feb. 1, 2007.
Office Action, U.S. Appl. No. 10/660,288, mailed Jun. 28, 2007.
Office Action, U.S. Appl. No. 10/660,288, mailed Apr. 29, 2009.
Office Action, U.S. Appl. No. 10/660,288, mailed Aug. 3, 2009.
Office Action, U.S. Appl. No. 10/660,288, mailed Mar. 30, 2010.
Office Action, U.S .Appl. No. 10/660,288, mailed Mar. 29, 2011.
Notice of Allowance, U.S. Appl. No. 10/660,288, mailed Sep. 30, 2011.
Office Action, U.S. Appl. No. 10/729,541, mailed Dec. 12, 2006.
Office Action, U.S. Appl. No. 10/729,541, mailed Jun. 18, 2007.
Office Action, U.S. Appl. No. 10/729,541, mailed Jan. 8, 2008.
Office Action, U.S Appl. No. 10/729,541, mailed Sep. 23, 2008.
Office Action, U.S. Appl. No. 10/729,541, mailed May 1, 2009.
Notice of Allowance, U.S. Appl. No. 10/729,541, mailed Nov. 16, 2009.
Notice of Allowance, U.S. Appl. No. 10/729,541, mailed Mar. 25, 2010.
Notice of Allowance, U.S. Appl No. 10/729,541, mailed Jul. 12, 2010.
Issue Notification, U.S. Appl. No. 10/729,541, mailed Nov. 3, 2010.
Office Action, U.S. Appl No. 10/737,668, mailed Nov. 2, 2005.
Office Action, U.S. Appl. No. 10/737,668, mailed Feb. 16, 2006.
Office Action, U.S. Appl. No. 10/737,668, mailed Oct. 19, 2006.
Office Action, U.S. Appl. No. 10/737,668, mailed Jun. 7, 2007.
Office Action, U.S. Appl. No. 10/737,668, mailed Nov. 28, 2007.
Notice of Allowance, U.S. Appl. No. 10/737,668, mailed Jun. 26, 2008.
Office Action, U.S. Appl. No. 10/742,406, mailed Mar. 23, 2007.
Notice of Allowance, U.S. Appl. No. 10/742,406, mailed Sep. 10, 2007.
Notice of Allowance, U.S. Appl. No. 10/742,406, mailed Jan. 11, 2008.
Office Action, U.S. Appl. No. 10/746,210, mailed Apr. 5, 2007.
Office Action, U.S. Appl. No. 10/746,210, mailed Aug. 21, 2007.
Notice of Allowance, U.S. Appl. No. 10/746,210, mailed Jul. 9, 2008.
Office Action, U.S. Appl. No. 10/813,449, mailed Sep. 5, 2006.
Office Action, U.S. Appl. No. 10/813,449, mailed Jul. 16, 2007.

(56) References Cited

OTHER PUBLICATIONS

Office Action, U.S. Appl. No. 10/813,449, mailed Jan. 25, 2008.
Office Action, U.S. Appl. No. 10/813,449, mailed Aug. 14, 2008.
Office Action, U.S. Appl. No. 10/813,449, mailed Sep. 15, 2008.
Office Action, U.S. Appl. No. 10/813,449, mailed Feb. 3, 2009.
Office Action, U.S. Appl. No. 10/813,449, mailed Aug. 28, 2009.
Office Action, U.S. Appl. No. 10/813,449, mailed May 27, 2010.
Office Action, U.S. Appl. No. 10/909,531, mailed Apr. 4, 2007.
Office Action, U.S. Appl. No. 10/909,531, mailed Dec. 26, 2007.
Office Action, U.S. Appl. No. 10/909,531, mailed Jun. 13, 2008.
Office Action, U.S. Appl. No. 10/909,531, mailed Feb. 9, 2009.
Office Action, U.S. Appl. No. 10/909,531, mailed Sep. 16, 2009.
Notice of Allowance, U.S. Appl. No. 10/909,531, mailed Apr. 29, 2010.
Notice of Allowance, U.S. Appl. No. 10/909,531, mailed Aug. 20, 2010.
Issue Notification, U.S. Appl. No. 10/909,531, mailed Nov. 23, 2010.
Office Action, U.S. Appl. No. 10/948,445, mailed Jul. 11, 2007.
Office Action, U.S. Appl. No. 11/199,338, mailed Jan. 25, 2007.
Office Action, U.S. Appl. No. 11/199,338, mailed Oct. 5, 2007.
Office Action, U.S. Appl. No. 11/199,338, mailed Dec. 28, 2007.
Office Action, U.S. Appl. No. 11/199,338, mailed Apr. 23, 2008.
Office Action, U.S. Appl. No. 11/199,338, mailed Jan. 6, 2009.
Office Action, U.S. Appl. No. 11/199,496, mailed Apr. 1, 2009.
Office Action, U.S. Appl. No. 11/199,496, mailed Aug. 21, 2009.
Office Action, U.S. Appl. No. 11/199,496, mailed Apr. 23, 2010.
Office Action, U.S. Appl. No. 11/199,496, mailed Apr. 28, 2011.
Notice of Allowance, U.S. Appl. No. 11/199,496, mailed Aug. 18, 2011.
Office Action, U.S. Appl. No. 11/199,515, mailed Aug. 20, 2008.
Office Action, U.S. Appl. No. 11/199,515, mailed Nov. 13, 2008.
Office Action, U.S. Appl. No. 11/199,515, mailed Jun. 10, 2009.
Notice of Allowance, U.S. Appl. No. 11/199,515, mailed Dec. 24, 2009.
Notice of Allowance, U.S. Appl. No. 11/199,515, mailed Apr. 2, 2010.
Notice of Allowance, U.S. Appl. No. 11/199,515, mailed Aug. 2, 2010.
Office Action, U.S. Appl. No. 11/273,107, mailed Jun. 14, 2007.
Office Action, U.S. Appl. No. 11/273,107, mailed Jan. 18, 2008.
Office Action, U.S. Appl. No. 11/273,107, mailed Sep. 5, 2008.
Office Action, U.S. Appl. No. 11/273,107, mailed Apr. 9, 2009.
Office Action, U.S. Appl. No. 11/273,107, mailed Oct. 28, 2009.
Office Action, U.S. Appl. No. 11/273,107, mailed Jun. 2, 2010.
Office Action, U.S. Appl. No. 11/273,107, mailed Oct. 27, 2010.
Notice of Allowance, U.S. Appl. No. 11/273,107, mailed Jun. 2, 2011.
Office Action, U.S. Appl. No. 11/363,005, mailed Jun. 22, 2007.
Office Action, U.S. Appl. No. 11/363,005, mailed Dec. 14, 2007.
Office Action, U.S. Appl. No. 11/363,005, mailed Apr. 17, 2008.
Office Action, U.S. Appl. No. 11/363,005, mailed Dec. 23, 2008.
Notice of Allowance, U.S. Appl. No. 11/363,005, mailed Jul. 10, 2009.
Notice of Allowance, U.S. Appl. No. 11/363,005, mailed Jan. 14, 2010.
Notice of Allowance, U.S. Appl. No. 11/363,005, mailed Jul. 23, 2010.
Issue Notification, U.S. Appl. No. 11/363,005, mailed Nov. 10, 2010.
Notice of Allowance, U.S. Appl. No. 11/389,762, mailed Sep. 20, 2007.
Notice of Allowance, U.S. Appl. No. 11/389,762, mailed Nov. 23, 2007.
Office Action, U.S. Appl. No. 11/390,937, mailed Sep. 7, 2007.
Office Action, U.S. Appl. No. 11/391,951, mailed Oct. 28, 2008.
Office Action, U.S. Appl. No. 11/391,951, mailed Jan. 30, 2009.
Office Action, U.S. Appl. No. 11/391,951, mailed Aug. 26, 2009.
Office Action, U.S. Appl. No. 11/391,951, mailed Jun. 23, 2010.
Office Action, U.S. Appl. No. 11/465,527, mailed Feb. 3, 2010.
Notice of Allowance, U.S. Appl. No. 11/465,527, mailed Jul. 23, 2010.
Issue Notification, U.S. Appl. No. 11/465,527, mailed Nov. 10, 2010.
Office Action, U.S. Appl. No. 11/552,593, mailed Aug. 21, 2008.
Office Action, U.S. Appl. No. 11/552,593, mailed Feb. 5, 2009.
Notice of Allowance, U.S. Appl. No. 11/552,593, mailed Oct. 13, 2009.
Notice of Allowance, U.S. Appl. No. 11/552,593, mailed Mar. 22, 2010.
Notice of Allowance, U.S. Appl. No. 11/552,593, mailed Jul. 22, 2010.
Issue Notification, U.S. Appl. No. 11/552,593, mailed Nov. 10, 2010.
Office Action, U.S. Appl. No. 11/688,722, mailed Mar. 10, 2010.
Notice of Allowance, U.S. Appl. No. 11/688,722, mailed Jul. 29, 2010.
Issue Notification, U.S. Appl. No. 11/688,722, mailed Nov. 17, 2010.
Office Action, U.S. Appl. No. 11/891,358, mailed Apr. 26, 2010.
Office Action, U.S. Appl. No. 11/891,358, mailed Oct. 19, 2010.
Office Action, U.S. Appl. No. 11/891,358, mailed Aug. 31, 2011.
Notice of Allowance, U.S. Appl. No. 11/891,358, mailed Nov. 18, 2011.
Notice of Allowance, U.S. Appl. No. 11/891,358, mailed Apr. 10, 2012.
Office Action, U.S. Appl. No. 11/891,513, mailed Apr. 9, 2010.
Office Action, U.S. Appl. No. 11/891,513, mailed Sep. 28, 2010.
Office Action, U.S. Appl. No. 11/891,513, mailed Aug. 31, 2011.
Notice of Allowance, U.S. Appl. No. 11/891,513, mailed Nov. 1, 2011.
Office Action, U.S. Appl. No. 11/960,593, mailed Sep. 14, 2010.
Office Action, U.S. Appl. No. 11/960,593, mailed Nov. 3, 2010.
Office Action, U.S. Appl. No. 11/960,593, mailed Apr. 28, 2011.
Office Action, U.S. Appl. No. 11/997,379, mailed Jul. 13, 2011.
Office Action, U.S. Appl. No. 11/997,379, mailed Feb. 28, 2012.
Office Action, U.S. Appl. No. 12/182,836, mailed Oct. 5, 2010.
Office Action, U.S. Appl. No. 12/182,836, mailed Jun. 23, 2011.
Office Action, U.S. Appl. No. 12/247,012, mailed Oct. 13, 2011.
Office Action, U.S. Appl. No. 12/247,012, mailed Mar. 16, 2012.
Office Action, U.S. Appl. No. 12/257,127, mailed Aug. 30, 2010.
Office Action, U.S. Appl. No. 12/257,127, mailed Dec. 22, 2010.
Office Action, U.S. Appl. No. 12/257,127, mailed Jul. 6, 2011.
Office Action, U.S. Appl. No. 12/257,127, mailed Jan. 12, 2012.
Office Action, U.S. Appl. No. 12/334,077, mailed Oct. 27, 2010.
Office Action, U.S. Appl. No. 12/334,077, mailed Jul. 21, 2011.
Office Action, U.S. Appl No. 12/334,085, mailed Dec. 23, 2010.
Office Action, U.S. Appl. No. 12/334,085, mailed Aug. 4, 2011.
Notice of Allowance, U.S. Appl. No. 12/334,085, mailed Jan. 9, 2012.
Office Action, U.S. Appl. No. 12/950,338, mailed Jun. 15, 2011.
Notice of Allowance, U.S. Appl. No. 12/950,338, mailed Nov. 1, 2011.
Office Action, U.S. Appl. No. 12/955,848, mailed Jun. 30, 2011.
Office Action, U.S. Appl. No. 12/955,848, mailed Nov. 15, 2011.
Office Action, U.S. Appl. No. 12/955,863, mailed Jan. 6, 2012.
Office Action, U.S. Appl. No. 12/955,869, mailed Oct. 18, 2011.
Notice of Allowance, U.S. Appl. No. 12/955,869, mailed Mar. 22, 2012.
Notice of Allowance, U.S. Appl. No. 12/961,239, mailed Jul. 26, 2011.
Notice of Allowance, U.S. Appl. No. 12/966,961, mailed Aug. 18, 2011.
Office Action, U.S. Appl. No. 13/022,050, mailed Jul. 11, 2011.
Request for Re-Examination, U.S. Appl. No. 90/006,469, mailed Nov. 29, 2002.
Office Action, U.S. Appl. No. 90/006,469, mailed Sep. 10, 2004.
Notice of Re-Issue, U.S. Appl. No. 90/006,469, mailed Sep. 27, 2005.
Re-Examination Certification, U.S. Appl. No. 90/006,469, mailed Jun. 27, 2006.
Notice of Allowance, U.S. Appl. No. 11/891,513, mailed May 8, 2012.
Notice of Allowance, U.S. Appl. No. 11/997,379, mailed May 11, 2012.
Notice of Allowance, U.S. Appl. No. 12/955,863, mailed May 15, 2012.
Office Action, U.S. Appl. No. 13/022,050, mailed Apr. 26, 2012.
Issue Notification, U.S. Appl. No. 11/891,358, mailed Jun. 13, 2012.

(56) References Cited

OTHER PUBLICATIONS

U.S. Appl. No. 13/525,875, filed Jun. 18, 2012, Voss.
Notice of Allowance, U.S. Appl. No. 13/022,050, mailed Jul. 6, 2012.
Notice of Allowance, U.S. Appl. No. 12/247,012, mailed Aug. 13, 2012.
Notice of Allowance, U.S. Appl. No. 12/950,338, mailed Aug. 8, 2012.
Issue Notification, U.S. Appl. No. 12/955,863, mailed Aug. 8, 2012.
Notice of Allowance, U.S. Appl. No. 12/257,127, mailed Sep. 20, 2012.
U.S. Appl. No. 13/443,659, filed Apr. 10, 2012, Fortson et al.
U.S. Appl. No. 13/445,053, filed Apr. 24, 2012, Fortson et al.
Issue Notification, U.S. Appl. No. 12/950,338, mailed Nov. 14, 2012.
Issue Notification, U.S. Appl. No. 13/022,050, mailed Oct. 31, 2012.
Notice of Allowance, U.S. Appl. No. 11/960,593, mailed Jul. 1, 2013.
Office Action, U.S. Appl. No. 12/182,836, mailed May 17, 2013.
Notice of Allowance, U.S. Appl. No. 13/615,530, mailed Jun. 12, 2013.
U.S. Appl. No. 13/870,628, filed Apr. 25, 2013, Ma.

\* cited by examiner

SUTURING DEVICES AND METHODS

CROSS-REFERENCE TO RELATED APPLICATIONS

N/A.

FIELD OF THE INVENTION

The present invention relates generally to medical devices, systems, and methods. In particular, the present disclosure relates to devices and methods for suturing of openings in body lumens. More specifically, the present invention relates to devices and methods for closing arterial and venous puncture sites.

BACKGROUND OF THE INVENTION

Catheterization and interventional procedures, such as, for example, angioplasty, catheterization, and the placement of stents, are commonly performed by inserting a hollow needle through the skin and tissue of a patient into the patient's vascular system. A guide wire is then often advanced through the needle and into the patient's blood vessel. The needle is then removed, enabling an introducer sheath to be advanced over the guidewire into the vessel, e.g., in conjunction with, or subsequent to, a dilator. A catheter or other device may then be advanced through a lumen of the introducer sheath and over the guidewire into a position for performing a medical procedure. Thus, the introducer sheath may facilitate introducing various devices into the vessel, while minimizing trauma to the vessel wall and/or minimizing blood loss during a procedure.

In practice, the introducer sheath is often inserted into the patient's vasculature using the modified Seldinger technique. In the Seldinger technique, a needle is first inserted into the vessel and a guide wire then follows through the needle. Next, the needle is removed and a sheath/dilator combination is advanced over the guide wire. The dilator expands the puncture in the vessel to a size suitable to receive the distal end of an introducer sheath. After the distal end of the sheath is disposed within the vessel, the dilator and guide wire are removed, thereby allowing access to the vessel lumen or other body lumen via the inserted introducer sheath.

Upon completing the diagnostic and/or treatment procedure, the devices and introducer sheath are removed, leaving a puncture site in the vessel wall. One will appreciate that it is desirable to close the puncture site in vessel wall. Closing the wound can be difficult due to substantial bleeding that can occur through an open wound in a blood vessel. One method of closing the puncture site includes applying external pressure to the puncture site until clotting and wound sealing occur; however, the patient must remain bedridden for a substantial period after clotting to ensure closure of the wound. This procedure can be time consuming and expensive, requiring as much as an hour of a physician's or nurse's time. It also can be uncomfortable for the patient and may require that the patient remain immobilized in the operating room, catheter lab, or holding area. In addition, a risk of hematoma exists from bleeding before hemostasis occurs.

Another method of puncture site closure is the use of bioabsorbable fasteners or sealing plugs. Bioabsorbable fasteners or sealing plugs can overcome many of the disadvantages associated with manual compression. Typically, these approaches rely on the placement of a thrombogenic and bioabsorbable material, such as collagen, at the superficial arterial wall over the puncture site. While potentially effective, this approach can suffer from a number of disadvantages. For example, it can be difficult to properly locate the interface of the overlying tissue and the adventitial surface of the blood vessel. Placing the plug too far from that interface can result in failure to provide hemostasis, and subsequent hematoma and/or pseudo-aneurysm formation. Conversely, if the plug intrudes into the artificial lumen, intravascular clots and/or collagen pieces with thrombus attached can form and embolize downstream, causing vascular occlusion. Also, thrombus formation on the surface of a plug protruding into the lumen can cause a stenosis, which can obstruct normal blood flow. Other possible complications include infection, as well as adverse reaction to the collagen or other implant.

Yet another approach for vascular closure includes the use of suture-applying devices. Conventional suture-applying devices are introduced through the tissue tract and advanced until a distal end of the device extends through the puncture site. One or more needles in the device are then deployed and used to draw suture through the blood vessel wall. Next, the suture is secured to provide closure of the puncture site. While suture-applying devices can overcome many of the difficulties associated with other puncture site closure devices and methods, locating the tissue surrounding a puncture site can be difficult using some suture-applying devices and methods. Some complications that may arise by misplaced or insufficiently anchored sutures include oozing, excessive bleeding, and potential knot loosening.

BRIEF SUMMARY

Briefly summarized, implementations of the present invention provide devices and methods for closing openings in a body lumen efficiently and quickly. For example, one or more implementations of the present invention provide suturing devices with tissue ports configured to allow for location of body lumen wall tissue surrounding a puncture site with increased accuracy and ease. This method can provide for suture deployment over the guide wire permitting rapid re-access to the vessel by the clinician. Furthermore, one or more implementations of the present invention can reduce miss-deployment of needles, and can allow for closure of larger body lumen openings.

For example, in one implementation, a suturing device configured to close an opening in a body lumen can include a shaft having a distal end and a proximal end. The distal end of the shaft can be defined by the distal most surface of the shaft. The shaft can include a first needle exit opening extending through the distal end thereof. The shaft can further include a second needle exit opening extending through the distal end thereof. The suturing device can further include a foot member secured to the distal end of the shaft. Additionally, the suturing device can include first and second needle capture devices removably secured to the foot member. The suturing device can also include at least one length of suture removably secured to the foot member. The at least one length of suture can have a first end secured to the first needle capture device and a second end secured to the second needle capture device.

In another implementation, a suturing device configured to close an opening in a body lumen can include a shaft having a distal end and a proximal end. The suturing device can also include a foot having a proximal tissue location surface and a distal tip. Additionally, the suturing device can include a spinal member connecting the foot member to the shaft. Also, the suturing device can include an actuator configured to move the foot from a first configuration, in which the tissue location surface is adjacent the distal end of the shaft, to a deployed configuration, in which the tissue location surface is distally separated from the distal end of the shaft by a length of the spinal member.

In yet another implementation, a suturing device configured to close an opening in a body lumen can include an elongate member including a proximal portion and a distal portion. The suturing device can also include first and second needle lumens extending through the proximal portion of the elongate member to first and second needle exit openings. Furthermore, the suturing device can include first and second needle capture devices secured to the distal portion of the elongate member. The first and second needle capture devices can be aligned with the first and second needle exit openings. Additionally, the first and second needle capture devices can be separated from the first and second needle exit openings by one or more tissue ports extending into the elongate member between the proximal portion and the distal portion. The suturing device can also include at least one length of suture within the distal portion of the shaft. The at least one length of suture can have a first end secured to the first needle capture device and a second end secured to the second needle capture device.

In addition to the foregoing, an implementation of a method of closing an opening in a body lumen wall can involve advancing a suturing device over a guidewire into the body lumen. The suturing device can include a shaft, a foot secured to a distal end of the shaft, and at least one tissue port located between the distal end of the shaft and the foot. The method can also involve advancing a pair of needles simultaneously through the shaft, out of needle exit openings in the distal end of the shaft, through wall tissue of the body lumen located in at least one tissue port, and into a pair of needle capture devices secured to the foot. Additionally, the method can involve withdrawing the pair of needles and the pair of needle capture devices from the suturing device, thereby at least partially withdrawing a suture connected to the pair of needle capture devices from the foot. Further, the method can involve employing the suture to close the opening in the body lumen wall.

Another implementation of a method of closing an opening in a body lumen wall can involve advancing a suturing device into the opening of the body lumen wall. The suturing device can include a shaft and a foot secured to a distal end of the shaft. The method can further involve articulating the foot from a first configuration in which the foot is adjacent a distal end of the shaft to a deployed configuration in which the foot is distally separated from the distal end of the shaft. The method can also involve advancing one or more needles through the shaft, through wall tissue of the body lumen located in between the shaft and the foot, and into one or more needle capture devices secured to the foot. The method can additionally involve employing the suture to close the opening in the body lumen wall.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. It should be noted that the figures are not drawn to scale, and that elements of similar structure or function are generally represented by like reference numerals for illustrative purposes throughout the figures. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figure 1:
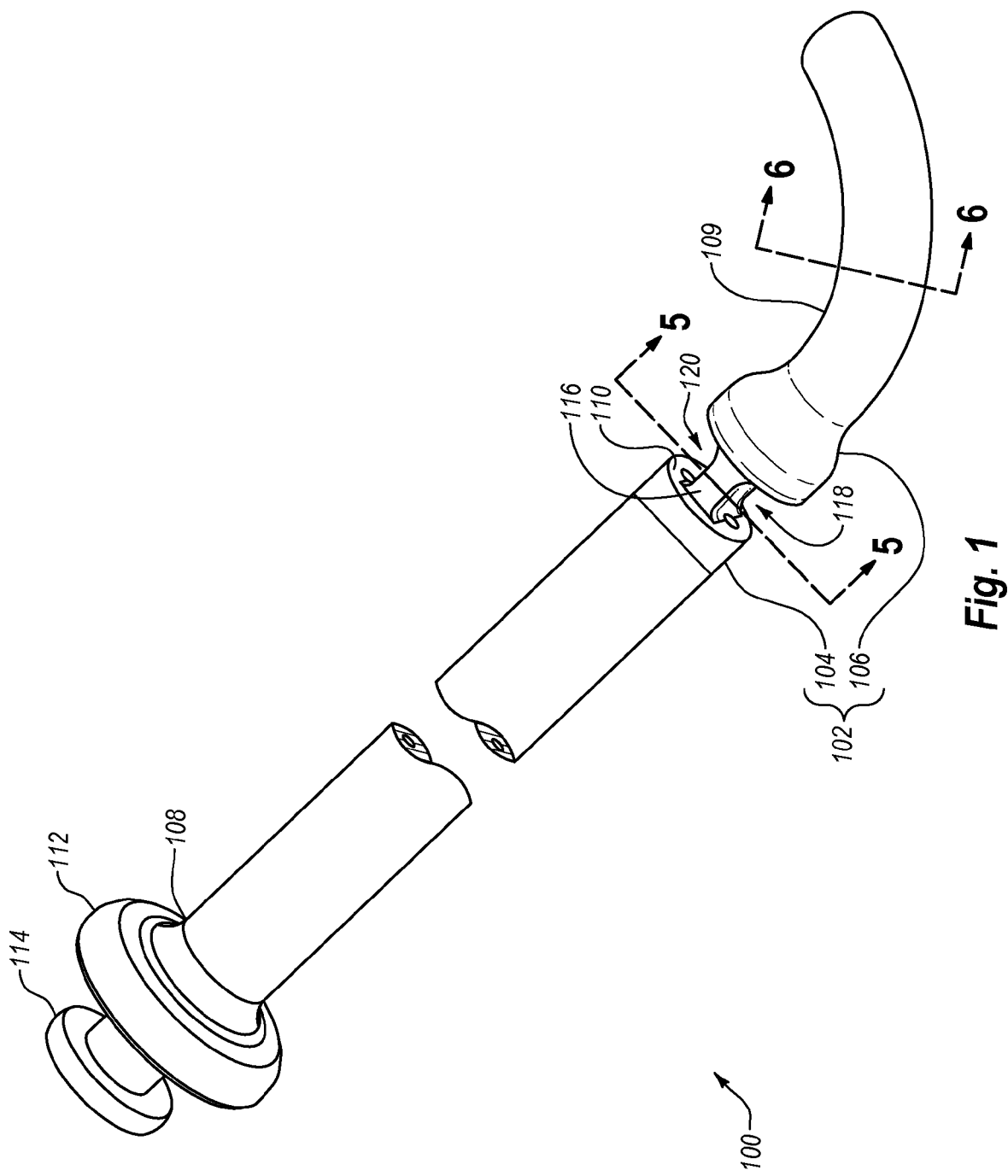
FIG. 1 illustrates a perspective view of a suturing device with a passive foot in accordance with an implementation of the present invention.

As previously mentioned, implementations of the present invention include devices and methods for closing openings in a body lumen efficiently and quickly. For example, one or more implementations of the present invention provide suturing devices with tissue ports configured to allow for location of body lumen wall tissue surrounding a puncture site with increased accuracy and ease. This method can provide for suture deployment over the guide wire permitting rapid re-access to the vessel by the clinician. Furthermore, one or more implementations of the present invention can reduce miss-deployment of needles, and can allow for closure of larger body lumen openings.

In particular, one implementation of the present invention can include a suturing device having a body including a shaft and a foot for insertion into an opening in a body lumen. The body can include tissue ports between the shaft and the foot configured to receive tissue of the body lumen surrounding the opening. The foot can include a suture secured to needle capture devices. Needles can be advanced within the shaft, through tissue within the tissue ports, and into the needle capture devices. The needle capture devices can then be withdrawn, thereby harvesting the suture, which can then be used to close the opening in the body lumen.

In some implementations of the present invention, the tissue ports in the body of the suturing device can be passive. In other words, the tissue ports can be formed between the shaft and the foot and remain open at all times. In alternative implementations, the tissue ports can be non-passive. In such implementations, the foot can articulate between a pre-deployed configuration and deployed configuration. In the pre-deployed configuration the tissue ports can be at least partially closed. For example, in one implementation the foot can abut against the shaft when in the pre-deployed configuration. In the deployed configuration the tissue ports can be open. For example, in one implementation the foot can be distally displaced from the foot when in the deployed configuration, thereby opening tissue ports between the foot and the shaft. In implementations including an articulating foot, the foot can be used to draw or push tissue surrounding an opening in a body lumen into the tissue ports.

Additionally, one or more implementations of the present invention include devices and procedures that allow a medical practitioner to insert a first suturing device over a guidewire into a tissue opening, deploy at least one suture, and remove the suturing device from the tissue opening before removing the guidewire. One will appreciate that this can allow the medical practitioner to run an additional suturing device over the same guidewire if the medical practitioner is not able to close the tissue opening using the first suturing device. For example, if needles used to harvest the suture of the first suturing device miss-deploy or otherwise fail to harvest the suture, the medical practitioner can remove the first suturing device and deploy another without having to place a second guidewire.

As an initial matter, as used herein, the term "proximal" refers to a direction toward a user (i.e., a medical practitioner or surgeon) of a suturing device and away from the patient, or a location closer to the user of the suturing device. As used herein, the term "distal" refers to a direction towards the patient and away from the user of the suturing device, or a location closer to the patient.

Turning now to the Figures, FIG. 1 shows an implementation of a suturing device 100 for closing an incision, a puncture, a passage, or opening through tissue or a body lumen. In particular, the implementation shown by Figure in is a suturing device 100 that includes passive tissue ports. In some examples, the suturing device 100 can close communication with a blood vessel or other body lumen. As shown in FIG. 1, the suturing device 100 can include a body or elongate member 102. The body 102 can have an annular configuration positioned about a central axis. For example, the body 102 illustrated in FIG. 1 includes a circular cross-section. In additional implementations, the body 102 may include other non-circular shapes as well, such as elliptical or other symmetrical or non-symmetrical shapes.

In any event, the body 102 can include a proximal portion or shaft 104 and a distal portion or foot 106. FIG. 1 further illustrates that the suturing device 100 can include a flexible, guidebody 109 extending distally from the distal end of the foot 106. As explained in greater detail below, the guidebody 109 can be advanced along a guidewire into a body lumen. Thus, at least the distal portion of the guidebody 109 can be formed from a flexible or elastomeric material that is biocompatible, particularly with blood. For example, in some implementations the guidebody 109 can be composed of a biocompatible polymeric material, such as, for example, silicone rubber, polyolefin, polyurethane, polytetrafluoroethylene, or similar materials. In additional implementations, the guidebody can be coated or impregnated with a lubricant, bioactive agent, such as an anticoagulant material, Polyvinylpyrrolidone (PVP), or the like. For example, the bioactive agent may have any therapeutic effect. Examples of additional suitable therapeutic properties may include anti-proliferative, anti-inflammatory, antiplatelet, anti-fibrin, antithrombotic, anti-mitotic, antibiotic, antiallergic, antioxidant properties, and/or other therapeutic properties.

For example, a bioactive agent may be used to reduce scar tissue response when after the guidebody is withdrawn from the tissue of a body lumen. Reducing scar tissue response, structural tissue response, restenosis, and/or thrombosis may facilitate access to the tissue after the opening has been sutured. For example, if a device did not use a beneficial agent to reduce scar tissue response, structural tissue response, restenosis, and/or thrombosis after deployment, these and/or other tissue responses may hinder future access to the tissue.

The foot 106 can include a flared portion that extends radially outward of the guidebody 109 and/or shaft 104. The foot 106 may be machined or cast from a composite material, such as, for example, carbon fiber. In some implementations, the foot 106 can be molded as two separate halves which can be subsequently affixed together. In yet further implementations, the foot 106 may comprise a biocompatible material, such as, for example, stainless steel, nylon, or similar materials.

The shaft 104 can include a proximal end 108 and a distal end 110 (i.e., the terminal end or surface of the shaft 104). The shaft 104 can comprise a biocompatible material, such as stainless steel, carbon fiber, nylon, another suitable polymer, or similar materials. Furthermore, in some implementations the shaft 104 may be flexible to accommodate insertion into a body lumen. In alternative implementations, the shaft 104 may comprise a rigid construction so as to avoid substantial deflection during use.

A handle 112 can be secured to the proximal end 108 of the shaft 104. The handle 112 can be of sufficient dimensions to allow a medical practitioner to grasp the handle 112 and use it to manipulate the suturing device 100 during use. Furthermore, the handle 112 can support a needle actuation handle 114. The proportions of the needle actuation handle 114 and needles 122/124 may be change with respect to each other to improve needle stroke and column strength. The handle 112 and the needle actuation handle 114 may include a bioabsorbable metal, alloy, polymer, plastic, composite, other materials, or combinations thereof.

The foot 106 can be secured to the distal end 110 of the shaft 104 by a spinal member 116. The spinal member 116 can separate the distal end 110 of the shaft 104 from the foot 106, and thus, define one or more tissue ports 118, 120. The spinal member 116 can be composed of a biocompatible material that is substantially resistant to deformation, and therefore, can maintain alignment between the needle lumen 126, 128 and the needle capture devices 136, 138. One will appreciate that the spinal member's resistance to deformation can help ensure that needles 122, 124 are not miss-deployed. Furthermore, the spinal member can serve to maintain structural integrity between the shaft 104 and foot 106. Examples of suitable materials include stainless steel, polytetrafluoroethylene, nylon, polyamids, and similar materials.

Figure 5:
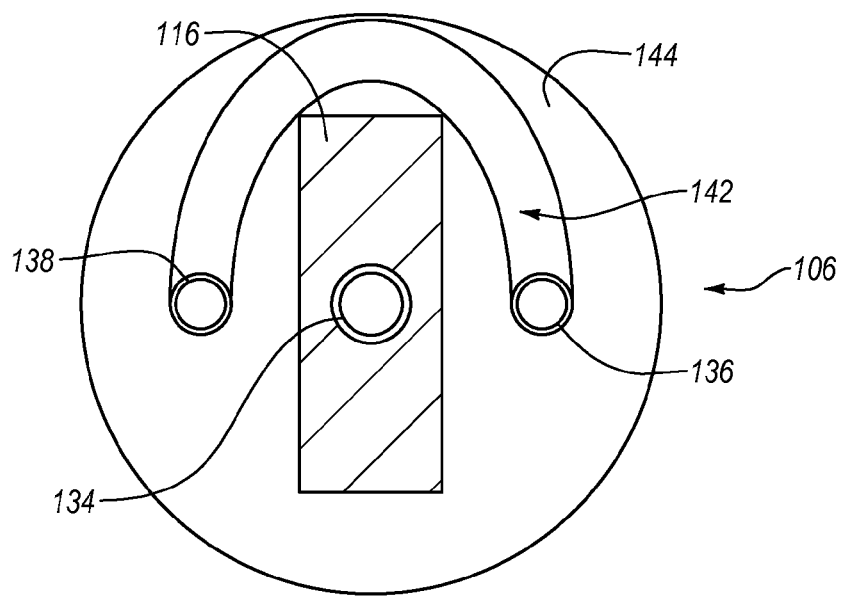
FIG. 5 illustrates a partial, cross-sectional view of the suturing device of FIG. 1 taken along the line 5-5 of FIG. 1.

Furthermore, FIG. 5 illustrates that the spinal member 116 can have a width equal to approximately the diameter of the foot 106. Thus, referring again to FIG. 1, the spinal member 116 can define two tissue ports 118, 120 separating the distal end 110 of the shaft 104 from the foot 106. In alternative implementations, the spinal member 116 can have a width smaller than the diameter of the shaft 104, and thus, define a single circumferential tissue port. Alternatively, the suturing device 100 can include three or more tissue ports.

In any event, the body 102 can include one or more tissue ports 118, 120 separating the distal end 110 of the shaft 104 from the foot 106. As explained in greater detail below, the tissue ports 118, 120 can be configured to receive tissue surrounding an opening, such as a puncture wound, in a body lumen wall. The tissue ports 118, 120 can thus help locate the tissue surrounding an opening, and allow for the suturing of the tissue to close the opening.

Figure 2:
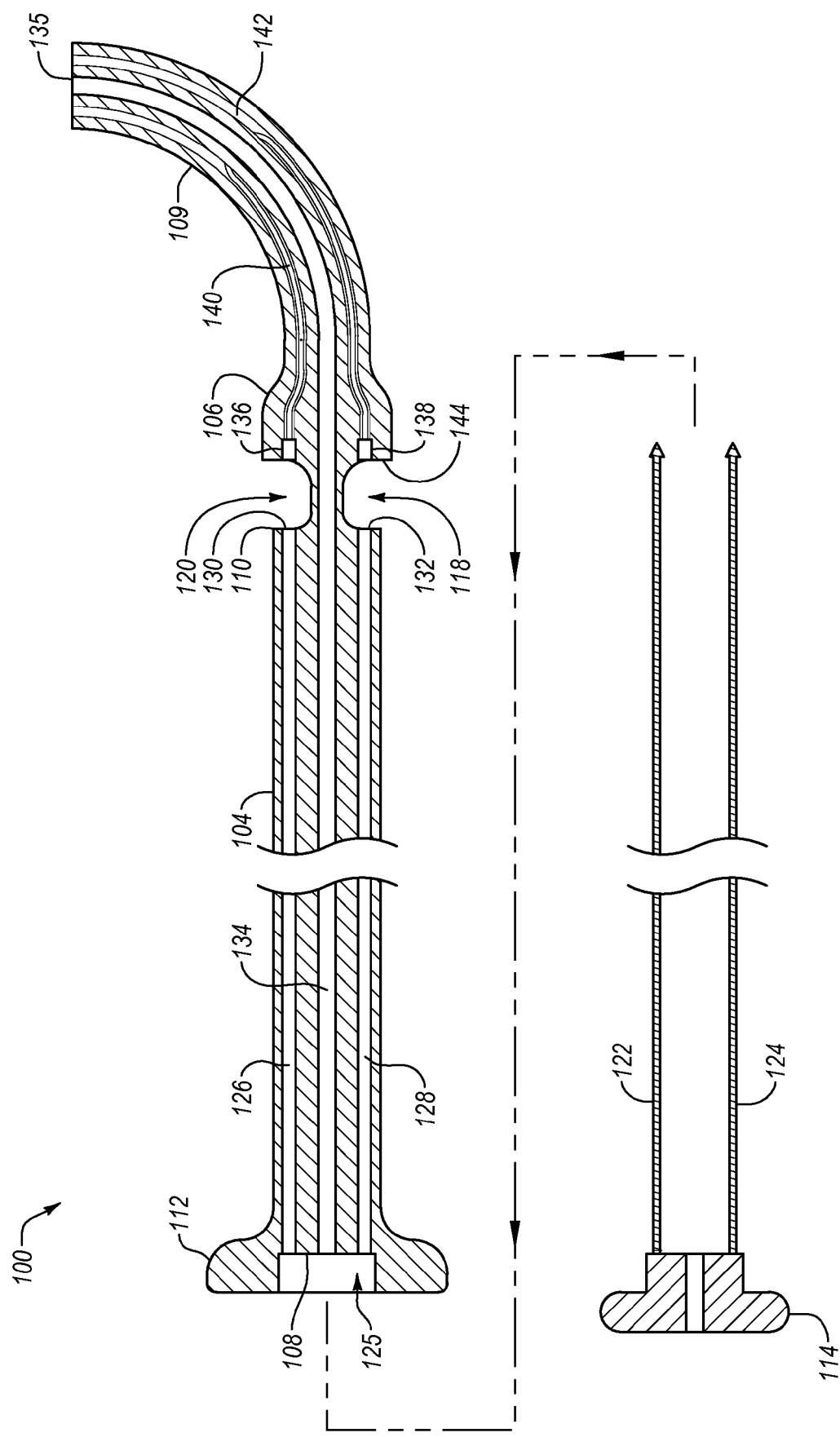
FIG. 2 illustrates an exploded, cross-sectional view of the suturing device of FIG. 1.
Figure 3:
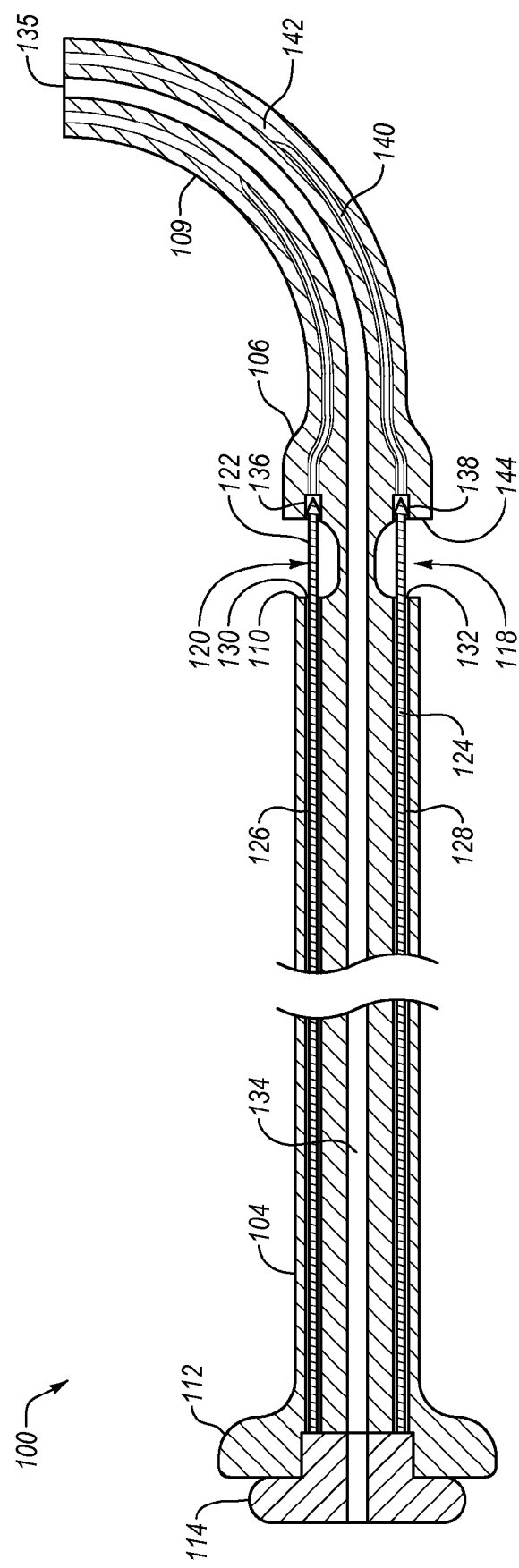
FIG. 3 illustrates a cross-sectional view of the suturing device of FIG. 1 with the needles thereof deployed.

Referring now to FIGS. 2 and 3, an exploded cross-sectional view and an assembled cross-sectional view, respectively, of the suturing device 100 are illustrated. As shown, the needle actuation handle 114 can include one or more needles secured thereto. In particular, the implementation shown in FIGS. 2 and 3 includes a first needle 122 and a second needle 124. In additional implementations, the suturing device 100 can include a single needle or three or more needles.

One or more of the needles for use with the suturing devices of the present invention can be provided as substantially described in U.S. Pat. No. 6,136,010 issued to Modesitt et al. and/or U.S. Pat. No. 5,792,152 issued to Klein et al, which are incorporated herein by reference in their entirety. As such in some implementations, the needles for use with the present invention can be flexible. Alternatively, needles for use with the present invention can be rigid. In particular, the needles can include sufficient column strength so as to avoid any meaningful deflection as they are advanced through tissue. By having a rigid construction, the needles can pass from the shaft 104, through tissue within the tissue ports 118, 120, and into the foot 106 without deflection. One will appreciate that this can help decrease or eliminate miss-deployment of needles sometimes associated with flexible needles. For example, a rigid construction can help ensure that the needles 122, 124 pass into the foot, instead of deflecting and missing the foot 106, or more specifically engagement features within the foot 106.

In any event, the needle actuation handle 114 can be engageable with or be secured to one or more needles. For example, FIG. 2 illustrates that the needle actuation handle 114 can be secured to the first needle 122 and the second needle 124. The needle actuation handle 114 can be sized to be positioned within a receptacle 125 extending into the proximal end 108 of the handle 112 and/or shaft 104. The needle actuation handle 114 can allow a medical practitioner to advance the needles 122, 124 into the shaft 104 and then the foot 106. Specifically, the needle actuation handle 114 can be configured such that a medical practitioner can advance the needles 122, 124 in a proximal direction toward the patient, and then subsequently in a distal direction away from the patient. In alternative implementations, the suturing device 100 may not include a needle actuation handle 114. In such implementations, the proximal ends of the needles 122, 124 can be configured to held and manipulated by the medical practitioner to advance and retract the needles 122, 124.

FIGS. 2 and 3 illustrate that the shaft 104 of the body 102 can include a plurality of axial lumens therein. For example, FIGS. 2 and 3 illustrate that the shaft 104 can include a pair of needle lumens 126, 128. The needle lumens 126, 128 can extend from the proximal end 108 to the distal end 110 of the shaft 104. In particular, the distal end 110 end of the shaft 104 can include a first needle exit opening 130 and a second needle exit opening 132, at the respective ends of the needle lumens 126, 128. The needle lumen 126, 128 can guide the needles 122, 124 from the proximal end 108 of the shaft 104, through the shaft 104, and out of the needle exit openings 130, 132.

In addition to the needle lumens 122, 124, the shaft 104 can include additional lumens. For example, the shaft 104 can include a foot position verification lumen, such as that described herein below in reference to the suturing device 300 shown in FIGS. 10A-131. Additionally, as shown in FIGS. 2 and 3, the shaft 104 can include a guidewire lumen 134. The guidewire lumen 134 can extend along the length of the shaft 104, through the foot 106, and through the guidebody 109. The guidewire lumen 134 can extend substantially along the central axis of the suturing device 100 as shown in FIGS. 2 and 3, or alternatively be offset from the central axis of the suturing device 100. Furthermore, in some implementations, the guidewire lumen 134 can serve as the spinal member 116.

The guidewire lumen 134 can receive or follow a guidewire left in place after a diagnostic or medical procedure. In particular, as explained in greater detail below, a medical practitioner can insert the suturing device 100 into a body lumen or other site to be repaired by sliding the guidewire lumen 134 over the pre-placed guidewire. For example, a medical practitioner can place an opening 135 in the distal end of the guidebody 109 over a guidewire (not shown). The guidewire can then extend through the guidewire lumen 134 and out of the needle actuation handle 114. Thus, the guidewire can extend out of the proximal end of the suturing device 100 without interfering with the needles 122, 124, needle lumens 126, 128, or suture. The guidewire can be removed after placement of the suturing device 100 in a body lumen, after deployment of the needles 126, 128, or after removal of the suturing device 100 from the patient, as considered prudent by the medical practitioner.

In addition to the guidewire lumen 134, the foot 106 can include one or more needle capture devices. For example, FIGS. 2 and 3 illustrate that the foot 106 can include a first needle capture device 136 and a second needle capture device 138. In alternative implementations, the foot 106 can include one needle capture device or three or more needle capture devices. One will appreciate that the number of needle capture devices in the foot 106 can correspond to the number of needles 122, 124 and needle lumens 126, 128 in the shaft 104. Each needle capture device 136, 138 can correspond to and be aligned with a needle lumen 126, 128, and a needle exit opening 130, 132. One will appreciate that by being aligned, the needles 122, 124 can pass out of the needle exit openings 130, 132, through the tissue ports 118, 120 and into the needle capture devices 136, 138.

Figure 6:
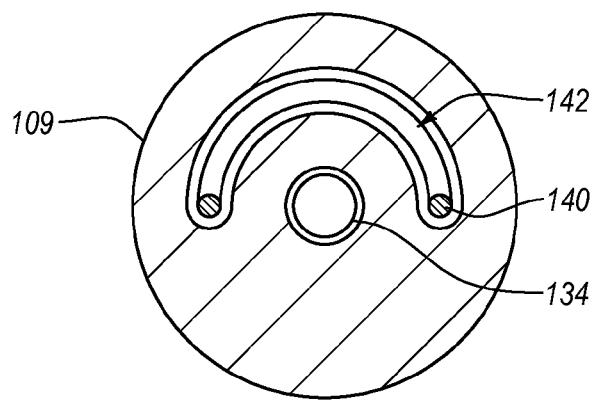
FIG. 6 illustrates a cross-sectional view of the suturing device of FIG. 1 taken along the line 6-6 of FIG. 1.

The needle capture devices 136, 138 can be secured to a suture 140 removably stored within a suture lumen 142 within the foot 106 and/or guidebody 109. For example, FIGS. 2 and 3 illustrates that the suturing device 100 includes a length of suture 140 having its respective ends secured to the first and second needle capture devices 136, 138. In particular, as illustrated by FIG. 6, the suture lumen 142 can extend at least partially around the guidewire lumen 134 and allow the suture 140 to wrap from the first needle capture device 136 to the section needle capture device 138. In alternative implementations, each needle capture device 136, 138 can have two or more sutures, ends or otherwise, secured thereto. As explained in greater detail below, multiple sutures may be desirable when closing larger openings or punctures within a body lumen.

The various implementations of the present invention may include any of a variety of suture types, such as, for example, monofilament or braided sutures. The sutures may be absorbable or non-absorbable, and may be made of polyester, polypropylene, polyglycolic acid, nylon, silk, or any of a variety of different materials.

Referring again to FIGS. 2 and 3, the suture 140 and the suture lumen 142 can extend from the foot 106 into the guidebody 109. In alternative implementations, the entire suture, or a substantially portion thereof, may be housed within the foot 106. For example, in some implementations, the suture 140 can be coiled and stored within the flared portion of the foot 106. In yet further implementations, the suture 140 can be stored or attached to the outer surfaces of the foot 106 or guidebody 109.

As shown by FIGS. 2 and 3, the needle capture devices 136, 138 can be configured to receive and secure the needles 122, 124 to the suture 140. In particular, once the needles 122, 124 are advanced into the needle capture devices 136, 138, the needle capture devices 136, 138 can lock the needles 122, 124 therein. Thereafter, when the needles 122, 124 are retracted from the foot 106 and the shaft 104, the needles 122, 124 can pull the suture 140 at least partially from the foot 106, through the needle lumens 126, 128, and out of the proximal end 108 of the shaft 104 or suturing device 100. In particular, by retracting the needles 122, 124, the suture 140 can be removed from the foot 106. Specifically, the suture 140 can pass out of the opening of the suture lumen 142 in the tissue location surface 144 (FIG. 5). Once the suture 140 has been harvested from the suturing device 100, the medical practitioner can remove the suturing device 100, retrieve the suture 140, and use it to close or otherwise seal an opening in a body lumen.

The needle capture devices 136, 138 can be substantially flush with a tissue location surface 144 (i.e., the surface of the foot opposite the distal end 110 of the shaft 104) as shown in FIGS. 2 and 3. Alternatively, the needle capture devices 136, 138 can reside further within the foot 106, as explained in greater detail below with reference to FIG. 9B. In such implementations, the foot 106 can include needle receiving lumens or funnels that extend from the tissue location surface 144 to the needle capture devices 136, 138, and that can guide the needles 122, 124 into the needle capture devices 136, 138.

As shown by FIGS. 2 and 3, the needles 122, 124 can be advanced in a distal direction from the proximal end 108 of the shaft 104 within the needle lumens 126, 128 by pressing the needle actuation handle 114 into the receptacle 125 of the handle 112 and/or shaft 104. The needles 122, 124 can advance out of the needle exit openings 130, 132, through tissue located within the tissue ports 118, 120, and into the needle capture devices 136, 138 within the foot 106. By being inserted into the needle capture devices 136, 138, the needle needles 122, 124 can be locked or secured to the suture 140. The needles 122, 124 and suture 140 can then be withdrawn proximately through the needle tracts formed in the tissue within the tissue ports 118, 120, and proximally out of the shaft 104 through the needle lumens 126, 128. In particular, by retracting the needles 122, 124, the suture 140 can be removed from the foot 106. Specifically, the suture 140 can pass out of the opening of the suture lumen 142 in the tissue location surface 144 (FIG. 5). Once the needles 122, 124 and suture 140 have been withdrawn from the foot 106, the suturing device 100 can be withdrawn from the patient. The suture 140 can then be drawn tight, closing the opening in the body lumen. A surgical knot or other suture securing device can complete the closure of the opening in the body lumen.

As previously mentioned, the needles 122, 124 can be configured to engage the needle capture devices 136, 138. One will appreciate that the needles 122, 124 and the needle capture devices 136, 138 can include various configurations so long as the needle capture devices 136, 138 can secure the needles 122, 124 to the suture 140, and allow the suture 140 to be harvested. For example, the needle capture devices 136, 138 of the present invention can include a net or other structure configured to receive and lock a needle to the suture 140.

Figure 4:
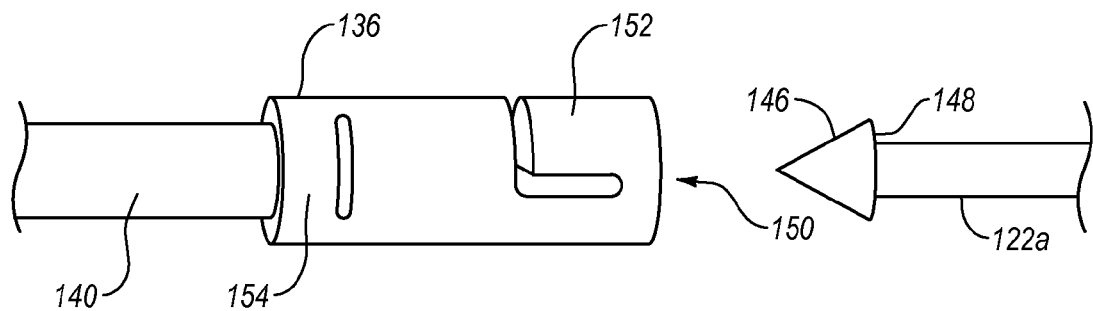
FIG. 4 illustrates a perspective view of a needle capture device and associated needle for use in the suturing device of FIG. 1.

In some implementations, as illustrated by FIG. 4, a needle 122a can include a barbed end 146 defining a recessed engagement surface 148. The needle capture device can comprise a needle attachment fitting or cuff 136. Specifically, the needle attachment cuff 136 can have a roughly cylindrical shape and include an axial channel 150 configured to receive the barbed end 146 of needle 122a therein. In additional implementations, the needle attachment cuff 136 can include shapes other than cylindrical ones, such as, for example, conical. The needle attachment cuff 136 can include one or more features configured to lock the barbed end 146 of the needle 122a therein. For instance, as shown in FIG. 4, the needle attachment cuff 136 can include at least one tab 152. The tab 152 may be mechanically formed to be smaller than the diameter of surface 148. The tab 152 can be resiliently biased into channel 150. As the needle 122a advances into the needle attachment cuff 136, the barbed end 146 can displace the tab 152 clear of the channel 150 so as to allow the barbed end 146 of the needle 122a to pass axially into the channel 105 of the needle attachment cuff 136. Once the barbed end 146 is disposed axially beyond the tab 152, the tab 152 tab can flex back into the channel 150 over the recessed surface 148, thereby locking the needle 122a to the needle attachment cuff 136. One will appreciate that each needle attachment cuff can include more than one tab 152, which can increase the reliability of the attachment between the needle 122a and the needle attachment cuff 136.

Additionally, FIG. 4 illustrates that the needle attachment cuff 136 can include a collar 154 to facilitate attachment of the needle attachment cuff 136 to suture 140. For instance, the collar 154 can be crimped about the suture 140 to mechanically affix the suture 140 to the needle attachment cuff 136. In addition and/or instead of mechanical crimping, the suture 140 may be bonded to the needle attachment cuff 136 using an adhesive, heat, fasteners, knots, or the like. As shown by FIG. 5, the foot 106 can house the needle attachment cuff 136. Or in other words, the needle attachment cuff 136 can extend distally into the tissue location surface 144 of the foot 106. In particular, in one implementation, the foot 106 can house a pair of needle attachment cuffs 136 on opposing sides of the spinal member 116 and/or guidewire lumen 134 (i.e., within the tissue ports 118, 120). FIG. 6 illustrates a cross-sectional view of the flexible guidebody 109. As shown by FIG. 6, and as previously mentioned, the guidewire lumen 134 and suture lumen 142 can extend into the flexible guidebody 109 in one or more implementations.

As mentioned previously, the needle capture devices 136, 138 can be removably secured to the foot 106 so they can be withdrawn proximally into the shaft 104 as the needles 122, 124 are withdrawn. Additionally, one will appreciate that the outer body of the needle capture devices 136, 138 can be configured with a taper or other feature to help allow the needle capture devices 136, 138 to be readily pulled through paths formed by the needles 122, 124 in tissue located within the tissue ports 118, 120 when the practitioner retracts the needles 122, 124 and the needle capture devices 136, 138 from the patient.

Reference is now made to FIGS. 7A-7G, which illustrate one implementation of a method of using the suturing device 100 to close an opening 210 in a body lumen 200. Specifically, the suturing device 100 can be inserted in a distal direction into the body lumen 200. This can be accomplished with or without the use of a guidewire. FIGS. 7A-7G illustrate an example in which a guidewire 202 is used.

Figure 7A:
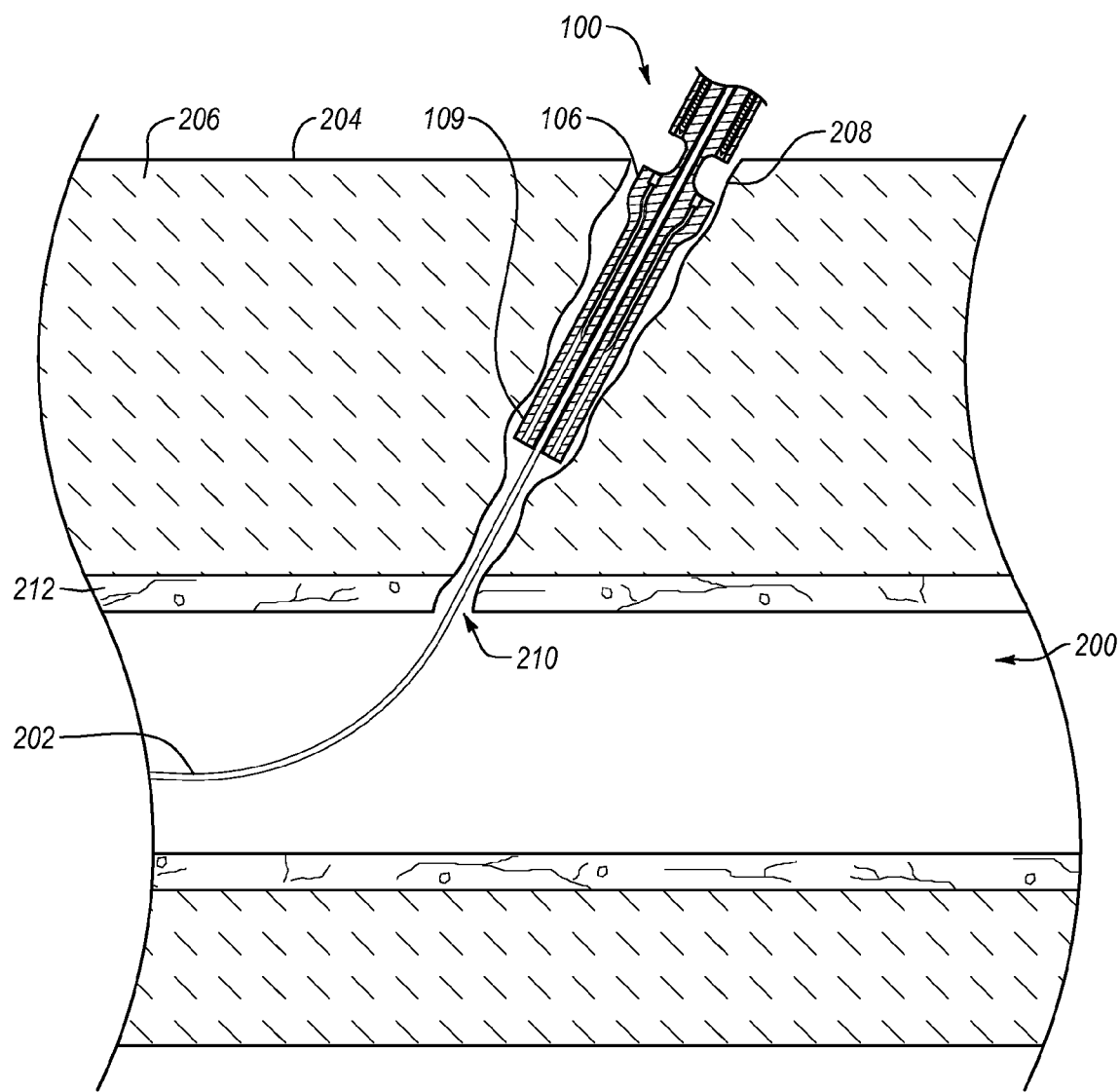
FIGS. 7A-7G illustrate cross-sectional views of a body lumen, showing a method for closing an opening in the wall of the body lumen using the suturing device of FIG. 1.
Figure 7B:
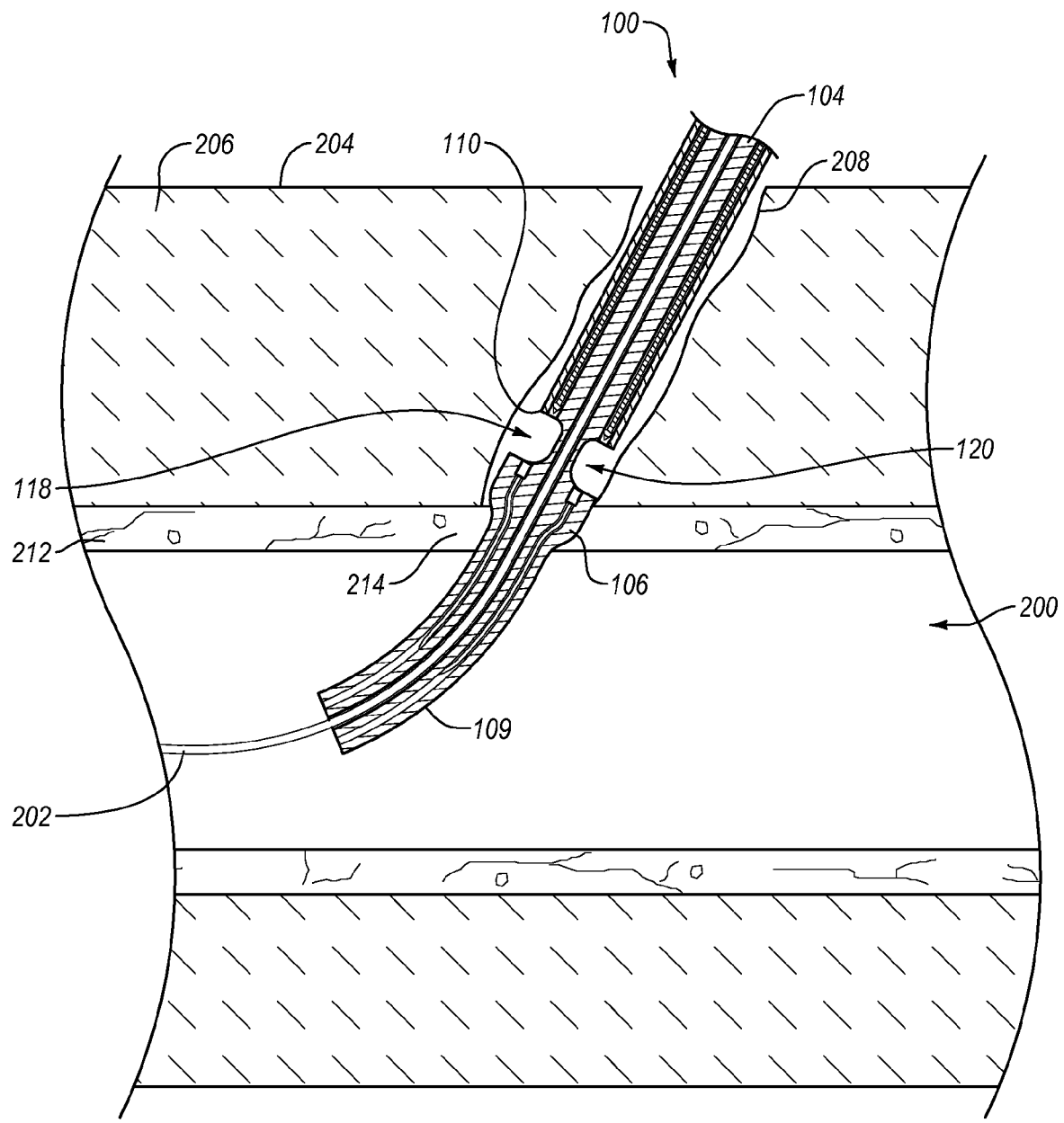

In particular, FIG. 7A illustrates that after accessing a body lumen, in this case a blood vessel 200, (using the Seldinger technique, for example), a guidewire 202 may be left extending into skin 204 and down through tissue 206 along a tissue tract 208, which may have been formed by an introducer sheath previously placed in connection with a intravascular medical or diagnostic procedure. As shown by FIG. 7A, the guidewire 202 may enter the body lumen 200 through an opening or puncture site 210 formed in the body lumen wall 212. The guidewire 202 may extend along the body lumen 200. As illustrated by FIGS. 7A-7B, the flexible guidebody 109 can be advanced over the guidewire 202 in a monorail fashion, so that the guidewire 202 helps direct the suturing device 100 along the tissue tract 208 into the body lumen 200 through the opening 210.

Figure 7C:
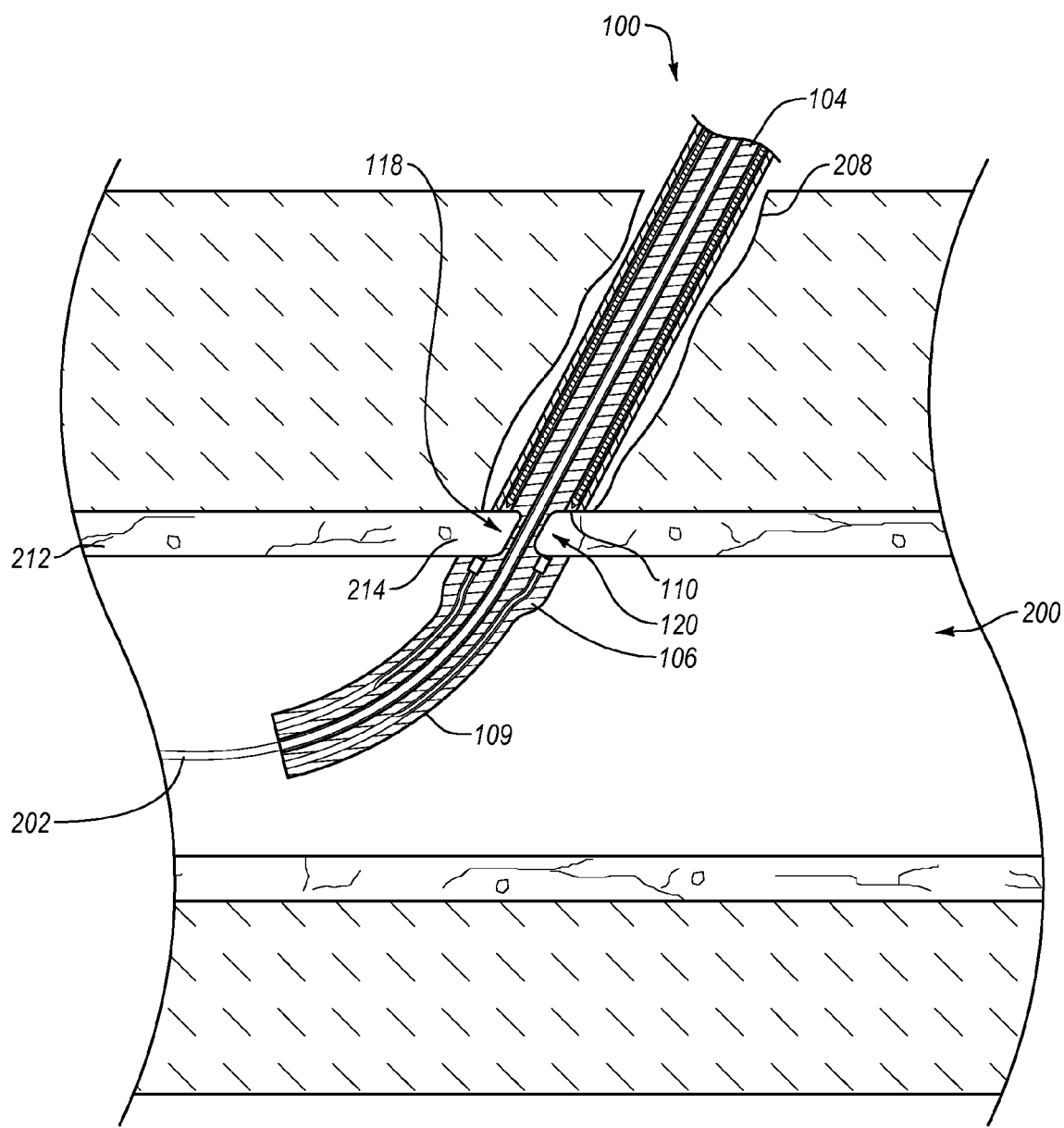

As shown by FIGS. 7B-7C, the suturing device 100 can be slowly advanced until resistance is encountered as the tissue ports 118, 120 cross the lumen wall 212 into the body lumen 200. The resistance can be provided by the radial flare of the foot 106 and/or by the distal end of the shaft 104. Alternatively, or additionally, the suturing device 100 can be advanced until blood is observed in a position indicator, such as that described below in relation to suturing device 300. In any event, once properly positioned, the suturing device 100 can be stabilized permitting the tissue 214 surrounding the opening 210 to rebound into the tissue ports 118, 120, as depicted in FIG. 7C.

Figure 7D:
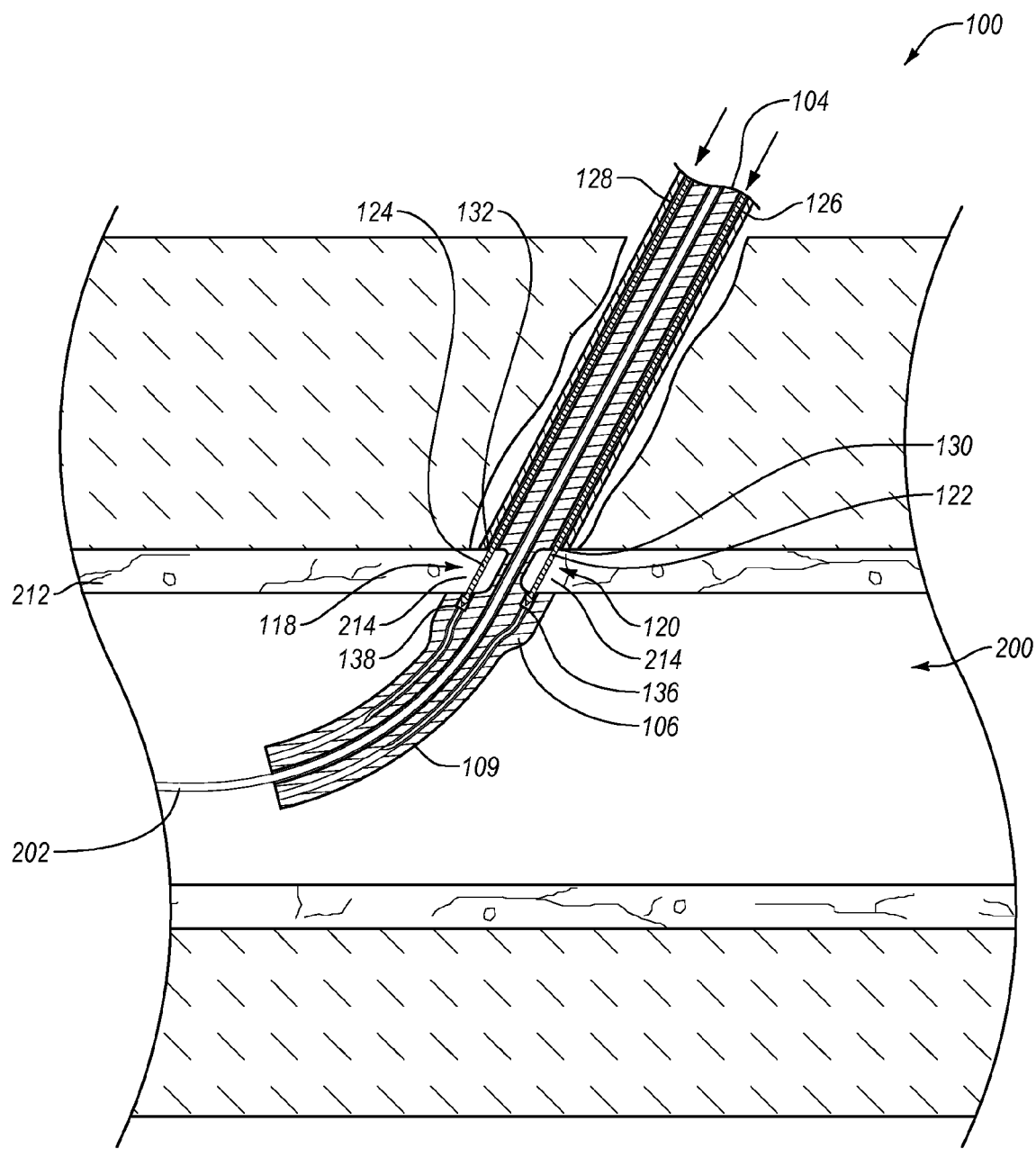
Figure 7E:
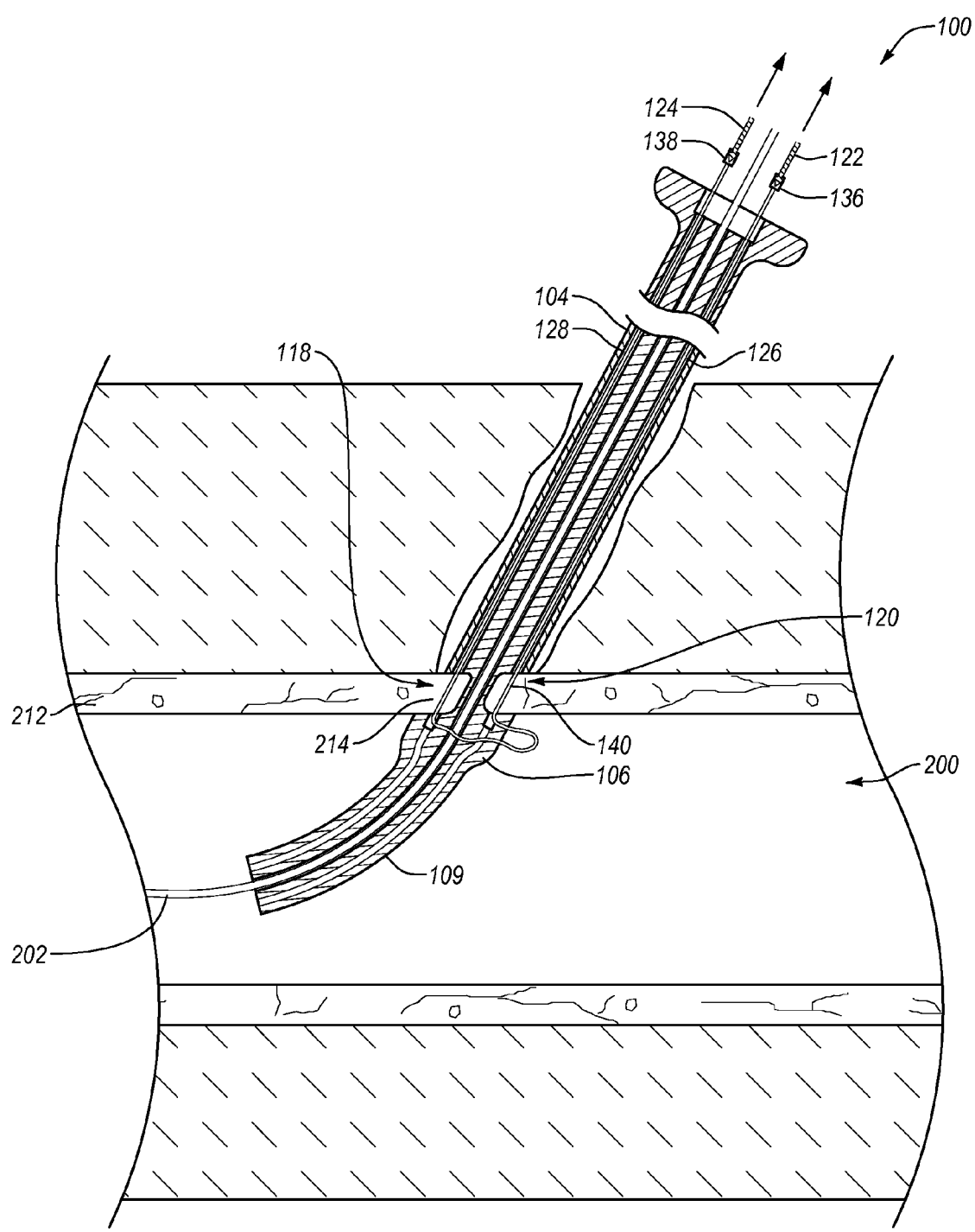

As shown in FIG. 7D, once the tissue 214 has entered into the tissue ports 118, 120, the needles 122, 124 can be advanced in a distal direction within the needle lumens 126, 128, out of the needle exit openings 130, 132, distally across the tissue ports 118, 120 through the tissue 214, and into the needle capture devices 136, 138. The needles 122, 124 and needle capture devices 136, 138 can then be withdrawn out of the foot 106, proximally across the tissue ports 118, 120 through the tissue 214, and out of the proximal end of the suturing device 100, as depicted by the arrow in FIG. 7E. FIG. 7E further shows that by withdrawing the needles 122, 124 and needle capture devices 136, 138, the distal end of the suture 140 can be withdrawn proximally out of the opening of the suture lumen 142 in the tissue location surface 144 and out of the foot 106.

Figure 7F:
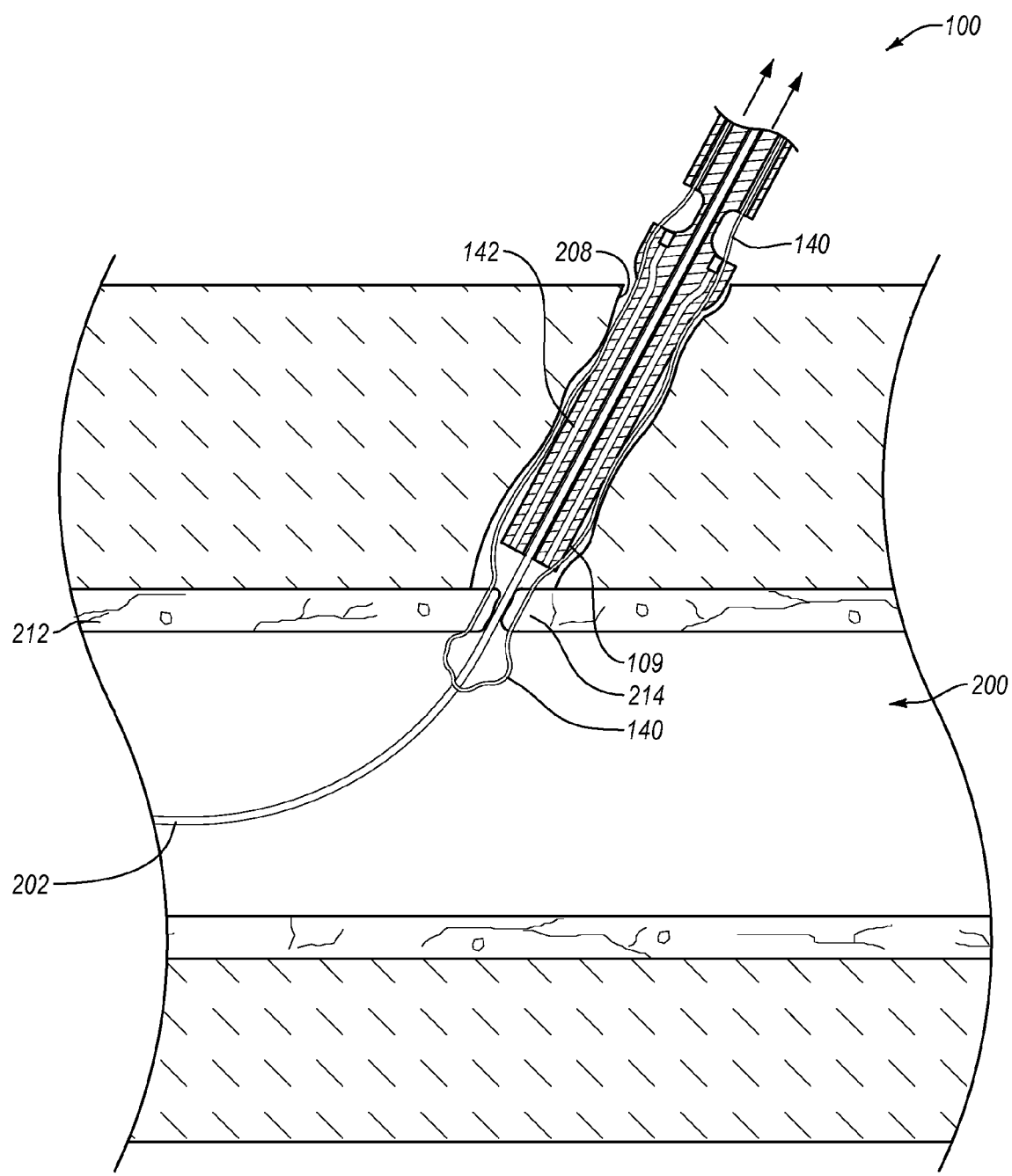

As indicated by the arrow of FIG. 7F, the suturing device 100 can next be withdrawn from the body lumen 200 and out of the tissue tract 208. As shown by FIG. 7F, the guidewire 202 can remain in place during the entire sequence to this point if desired. Thus, if the suture 140 fails to capture the tissue 214, or otherwise allow for the suture 140 to close the opening 210, another suturing device 100 can be inserted along the guidewire 202, and the above procedure repeated. One will appreciate that the ability to reuse the guidewire 202 if a problem is encountered can reduce the time, effort, and cost associated with resolving the problem and obtaining a dry closure of the body lumen 200.

Figure 7G:
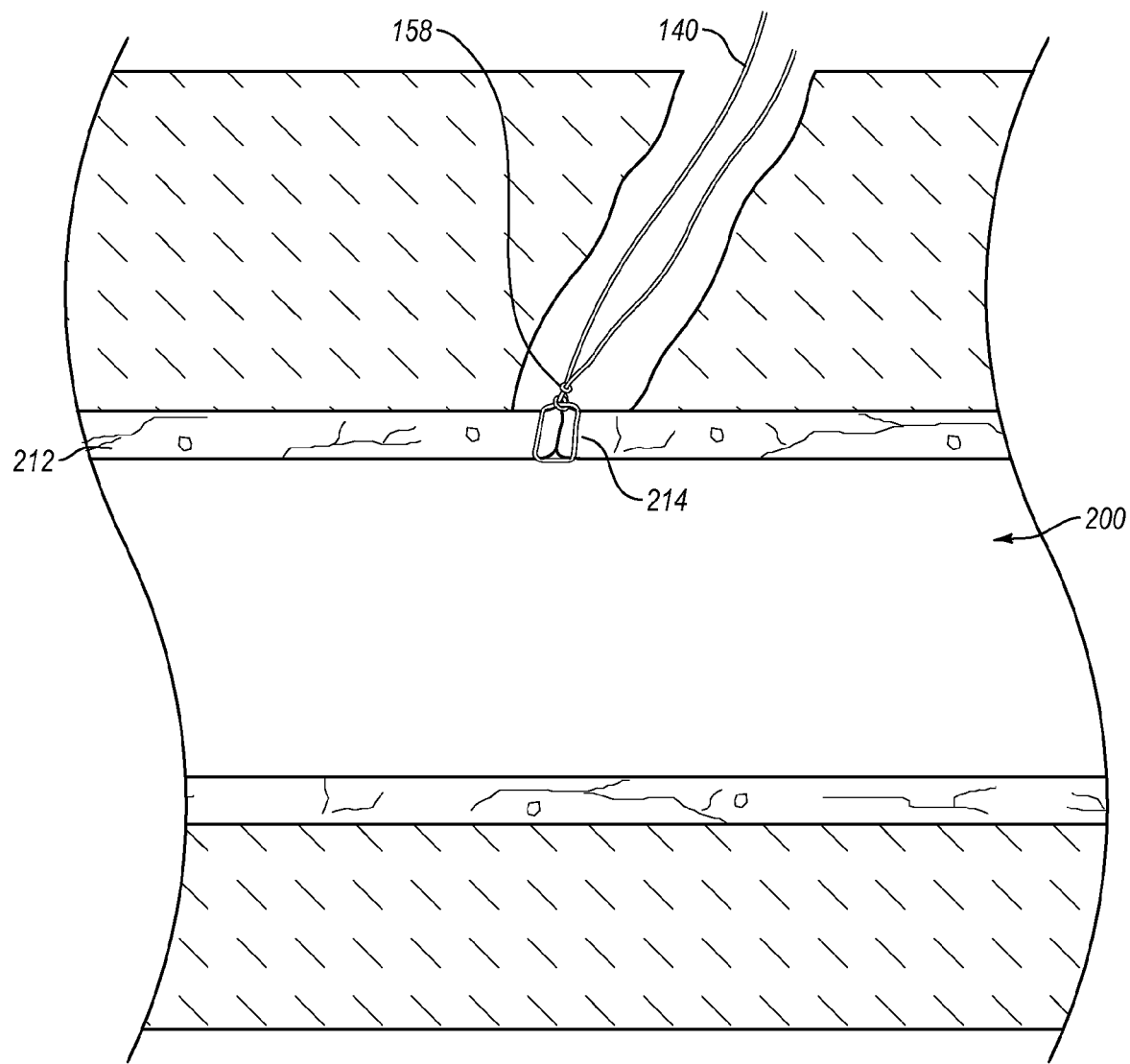

Finally, FIG. 7G illustrates that the guidewire 202 can be pulled from the patient. At this point, or prior thereto, the suture 140 can be employed to close the opening 210 in the body lumen 200. In particular, a surgical knot 158 can be tied securing the wound closure. A knot pusher, for example, the knot pushers described in U.S. Pat. No. 5,304,184 issued to Hathaway et al, U.S. Pat. No. 5,746,755 issued to Wood et al, and U.S. Pat. No. 6,132,439 issued to Kontos, can be used to advance the loosely tied knot to the exterior surface of the vascular vessel. In some implementations, the medical practitioner can then tie a suitable surgical knot 158 using the respective lengths of suture 140 to close the opening 210 (FIG. 7A). In other embodiments, the suture 140 can be secured using a variety of knot replacement technologies such as those disclosed in U.S. Pat. No. 7,108,710 issued to Anderson. Each of the above-identified patents are incorporated herein by reference in their entirety.

Figure 8:
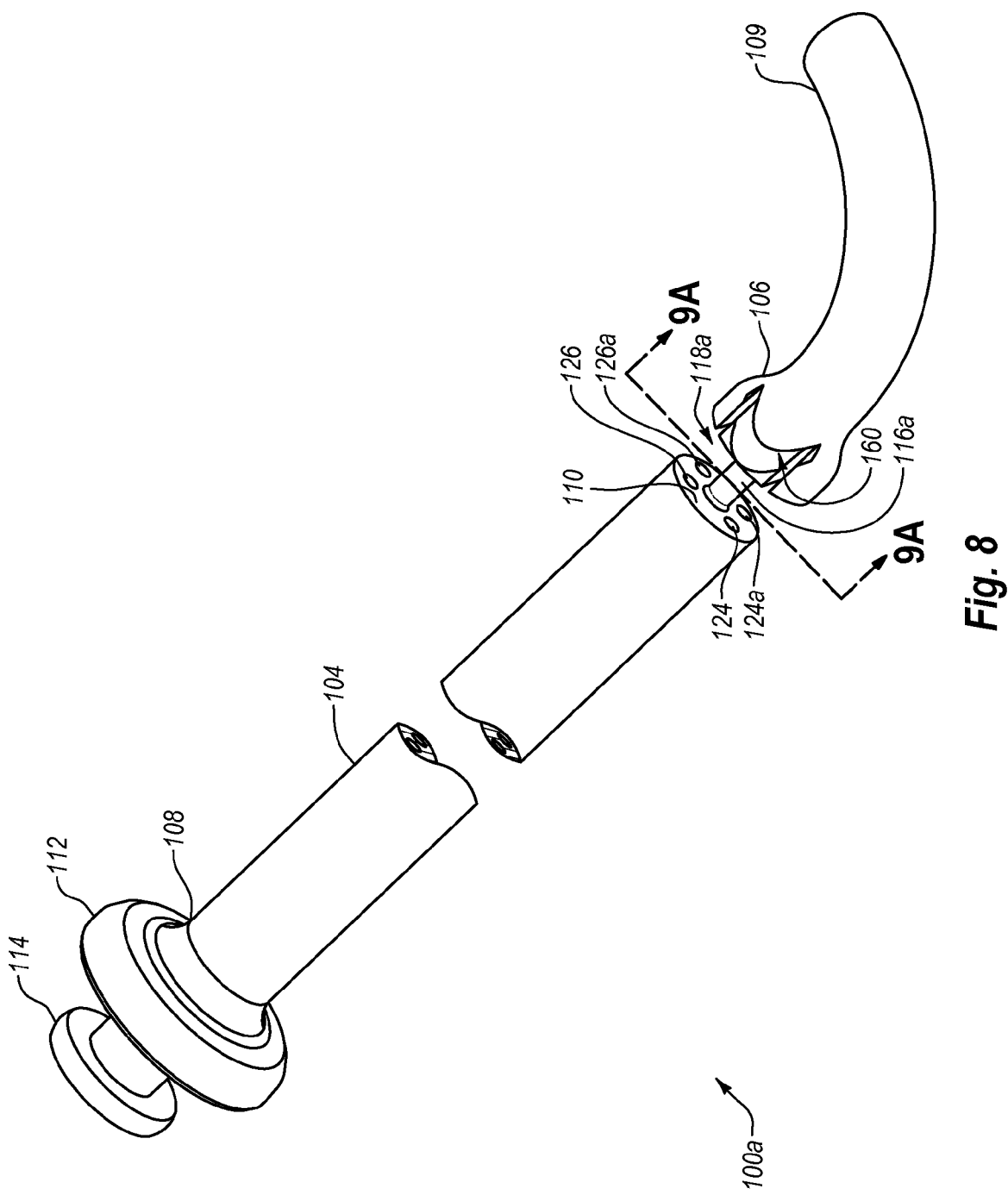
FIG. 8 illustrates a perspective view of another suturing device having a non-articulating foot in accordance with an implementation of the present invention.

In some cases, particularly for closure of large openings or punctures, it may be advantageous to provide multiple sutures 140 across the opening 210, either in parallel, in an "X" pattern, or in another configuration. For example, FIGS. 8 and 9 illustrate various views of a suturing device 100a similar to suturing device 100, except that suturing device 100a includes the use of more than two needles and associated needle lumens, needle capture devices, sutures, and the like. In particular, the suturing device 100a can include four needle lumens 124, 126, 124a, 126a, and four associated needles, four needle capture devices, and two sutures. Additional implementations of the present invention having multiple suture systems may have six, eight, or ten or more needles, or may even have odd numbers of needles and needle capture devices, particularly where one or more needle capture devices have a plurality of suture ends extending there from. This can allow a wide variety of stitching patterns to be provided by such multiple loop implementations.

More particularly, FIG. 8 illustrates that the suturing device 100a can include a shaft 104 and a distal portion or foot 106. FIG. 8 further illustrates that the suturing device 100a can include a flexible, guidebody 109 extending distally from the end of the foot 106. The foot 106 can include a flared portion that extends radially outward of the guidebody 109 and/or shaft 104. The shaft 104 can include a proximal end 108 and a distal end 110. A handle 112 can be secured to the proximal end 108 of the shaft 104. The handle 112 can be of sufficient dimensions to allow a medical practitioner to grasp the handle 112 and use it to manipulate the suturing device 100a during use. Furthermore, the handle 112 can support a needle actuation handle 114.

Figure 9A:
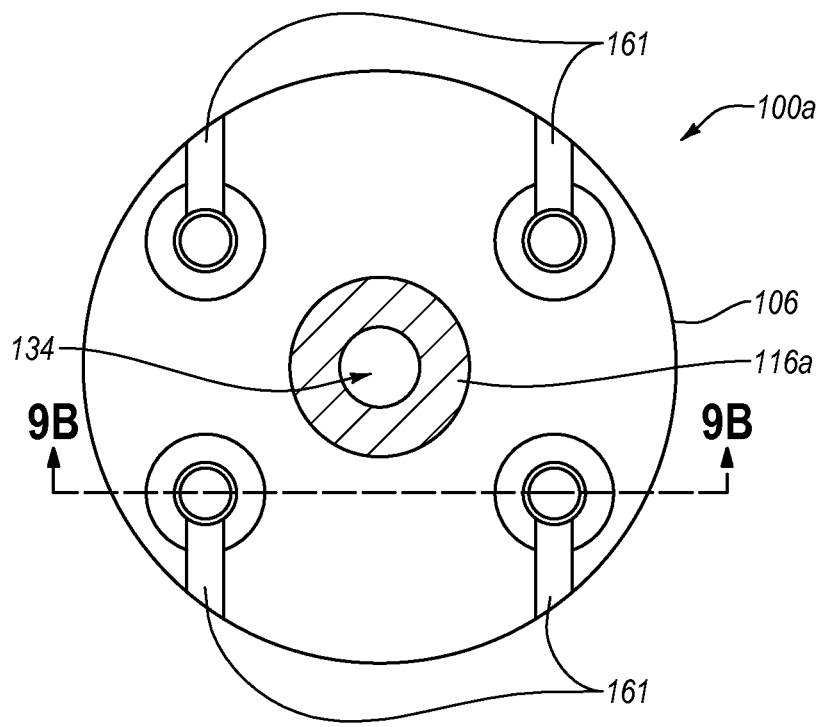
FIG. 9A illustrates a partial, cross-sectional view of the suturing device of FIG. 8 taken along the line 9A-9A of FIG. 8.

Furthermore, as illustrated by FIGS. 8 and 9A, the spinal member 116a can have a circular cross-section and a diameter several times smaller than the diameter of the shaft 104 and/or foot 106. Thus, the suturing device 100a can include a single, circumferential tissue port 118a. In yet further implementations, suturing devices of the present invention can include a single tissue port that extends only partially around the circumference of the shaft 104 and foot 106. In additional implementations, suturing devices of the present invention can include three, four, five, or more tissue ports.

FIGS. 8 and 9A further illustrate that the suturing device 100a can include one or more suture exit slots 160. The suture exit slots 160 can extend from inside the foot 106 and/or guidebody 109 from the sutures 140, radially outward and in a proximal direction. The suture exit slots 160 can replace the opening of the suture lumen 142 in the tissue location surface 144 used in the suturing device 100 and function to allow the sutures 140 to be pulled radially out from the foot 106 and/or guidebody 109 as the needles and needle capture devices are withdrawn proximally from the suturing device 100a. In other words, the sutures 140 can be pulled out of, and separated from foot 106 and/or guidebody 109 as the needles and needle capture devices are distally withdrawn (i.e., before the shaft 104, foot 106, and guidebody the suturing device 100a are withdrawn). One will appreciate that by having the suture exit slots 160, the space needed within the foot 106 and/or guidebody 109 to house the sutures 140 may be reduced.

Figure 9B:
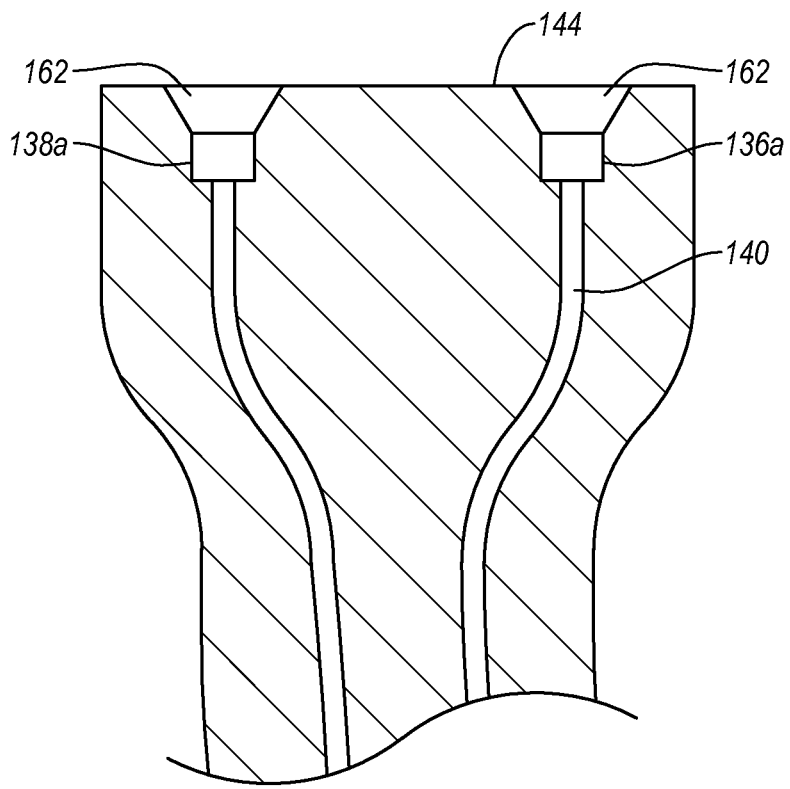
FIG. 9B illustrates a cross-sectional view of the suturing device of FIG. 9A taken along the line 9B-9B of FIG. 9A.

FIGS. 9A, 9B further illustrate that the suturing device 100a can include retaining slots 101. The retaining slots 161 can be configured to allow the foot 106 to receive and retain therein needle capture devices 136a, 138a. For example, the ports within the foot 106 within which the needle capture devices 136a, 138a can have a diameter smaller than the outer diameter of the needle capture devices 136a, 138a. The retaining slots 161 can allow the ports, which hold the needle capture devices 136a, 138a within the foot 106, to expand to receive the needle capture devices 136a, 138a. Once within the ports of the foot 106, the retaining slots 161 can allow the ports to bias toward and retain the needle capture devices 136a, 138a therein.

As alluded to earlier, the suturing devices of the present invention can include needle receiving lumens or funnels for guiding the needles into the needle capture devices 136a, 138a. For example, FIGS. 9A and 9B illustrate that the needle capture devices 136a, 138a can reside within the foot 106 a distance from the tissue location surface 144. Needle receiving lumens or funnels 162 can extend from the tissue location surface 144 to the needle capture devices 136a, 138a. The funnels 162 can have a diameter at the tissue location surface 144 that is larger than the diameter of the needle capture devices 136a, 138a. The diameter can then taper as the funnels extend toward the needle capture devices 136a, 138a. One will appreciate in light of the disclosure herein that the funnels 162 can thus guide the needles into the needle capture devices 136a, 138a in the event that they are slightly deflected out of alignment when passing through tissue.

While the implementations described hereinabove included passive tissue ports or non-articulating foot, the present invention is not so limited. As previously mentioned, implementations of the present invention can also include suturing devices with an articulating foot or non-passive tissue ports. Such implementations can include a foot that articulates between a pre-deployed configuration and deployed configuration. In the pre-deployed configuration the tissue ports can be at least partially closed. In the deployed configuration the tissue ports can be open. For example, in one implementation the foot can be distally displaced from the shaft when in the deployed configuration, thereby opening tissue ports between the foot and the shaft. In implementations including an articulating foot, the foot can be used to draw or push tissue surrounding an opening in a body lumen to be repaired into the tissue ports.

For example, FIGS. 10A-11B illustrate perspective view of a suturing device 300 with an actuating foot 106a in accordance with an implementation of the present invention. The suturing device 300 can include a body 102a comprising a proximal portion or shaft 104a and a distal portion or foot 106a. FIGS. 10A-12B further illustrate that the suturing device 300 can include a flexible, guidebody 109a extending distally from the end of the foot 106a. The foot 106a can include a flared portion that extends radially outward of the guidebody 109a. The shaft 104a can include a proximal end 108 and a distal end 110. A handle 112a can be secured to the proximal end 108 of the shaft 104a. The handle 112a can be of sufficient dimensions to allow a medical practitioner to grasp the handle 112a and use it to manipulate the suturing device 300 during use. Furthermore, the handle 112a can support a needle actuation handle 114a.

Similar to the suturing device 100, the suturing device 300 can include one or more needles 122, 124 secured to the needle actuation handle 114a. The needle actuation handle 114a can be sized to be positioned within a receptacle extending into the proximal end of the handle 112a. The needle actuation handle 114a can allow a medical practitioner to advance the needles 122, 124 into the shaft 104a and foot 106a. In particular, the shaft 104a can include one or more needle lumens 126, 128 extending from the proximal end 108 to the distal end 110 of the shaft 104a. The needle lumen 126, 128 can guide the needles 122, 124 from the proximal end 108 of the shaft 104a, through the shaft 104a, and into the foot 106a.

Additionally, the foot 106a can include one or more needle capture devices. For example, FIGS. 10B and 11B illustrates that the foot 106a can include a first needle capture device 136 and a second needle capture device 138, each removably secured within a tissue location surface 144 of the foot 106a. Each needle capture device 136, 138 can correspond to and be aligned with a needle lumen 126, 128. Referring now to FIG. 11C, the suturing device 100a can include retaining slots 161a configured to allow the foot 106a to receive and retain therein needle capture devices 136, 138.

The needle capture devices 136, 138 can be secured to a suture 140 removably stored within the foot 106a and/or guidebody 109a. For example, a length of suture 140 can have its ends secured to the first and second needle capture devices 136, 138. As previously mentioned, the needle capture devices 136, 138 can be configured to receive and secure the needles 122, 124 to the suture 140. In particular, once the needles 122, 124 are advanced into the needle capture devices 136, 138, the needle capture devices 136, 138 can lock the needles 122, 124 therein. Thereafter, when the needles 122, 124 are retracted from the foot 106a and the shaft 104a, the needles 122, 124 can pull the proximal ends of the suture 140 from the foot 106a, through the needle lumens 126, 128 and out of the proximal end 108 of the shaft 104a.

As shown by FIG. 11C, the suture 140 can extend from the needle capture devices 136, 138, out of retaining slots 161a, along the outer wall of the foot 106a, and into the guidebody 109a via suture exit slot 160a. As the needles 122, 124 are retracted from the foot 106a and the shaft 104a, the distal portion or loop of the suture 140 can be pulled from the guidebody 109a and foot 106a. In particular, as the suture 140 is pulled proximately, the suture 140 can exit the guidebody 109a and foot 106a via the suture exit slot 160a and retaining slots 161a. Once the suture 140 has been pulled from the guidebody 109a and foot 106a, the suturing device 300 can be proximately withdrawn from the patient. As shown in FIG. 11C, the suture exit slot 160a can extend generally radially outward from the center of the guidebody 109a. The radial configuration can help ensure that the suture exit slot 160a does not catch or pull on tissue as the suturing device 300 is withdrawn.

The suturing device 300 can further include a foot actuator mechanism 302. As shown in FIGS. 10A-11B, a medical practitioner can slide the foot actuator mechanism 302 distally toward the foot 106a, thereby causing the foot 106a to be distally displaced from a first configuration (FIGS. 10A-10B) in which the foot 106a abuts against the distal end 110 of the shaft 104a and a deployed configuration (FIGS. 11A-11B) in which the foot 106a is distally separated from the distal end 110 of the shaft 104a.

Figure 11A:
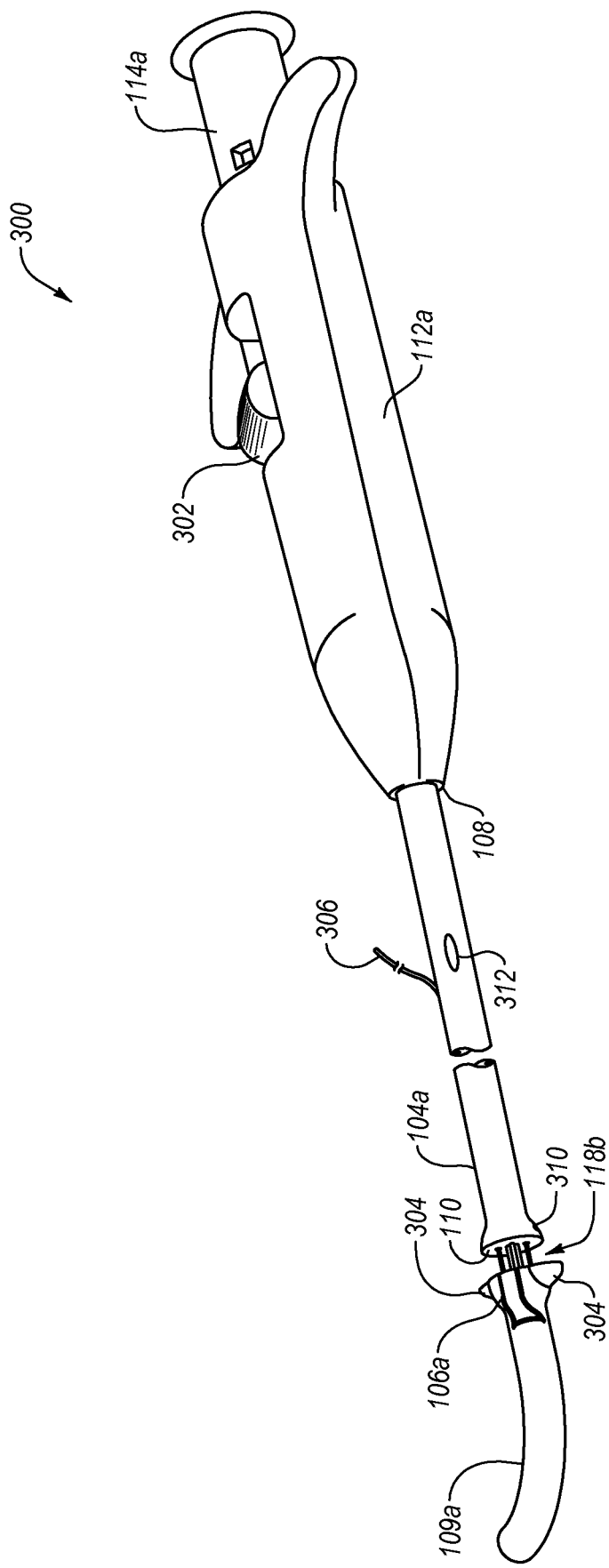
FIG. 11A illustrates a perspective view of the suturing device of FIG. 10A with the articulating foot in a deployed configuration.
Figure 11B:
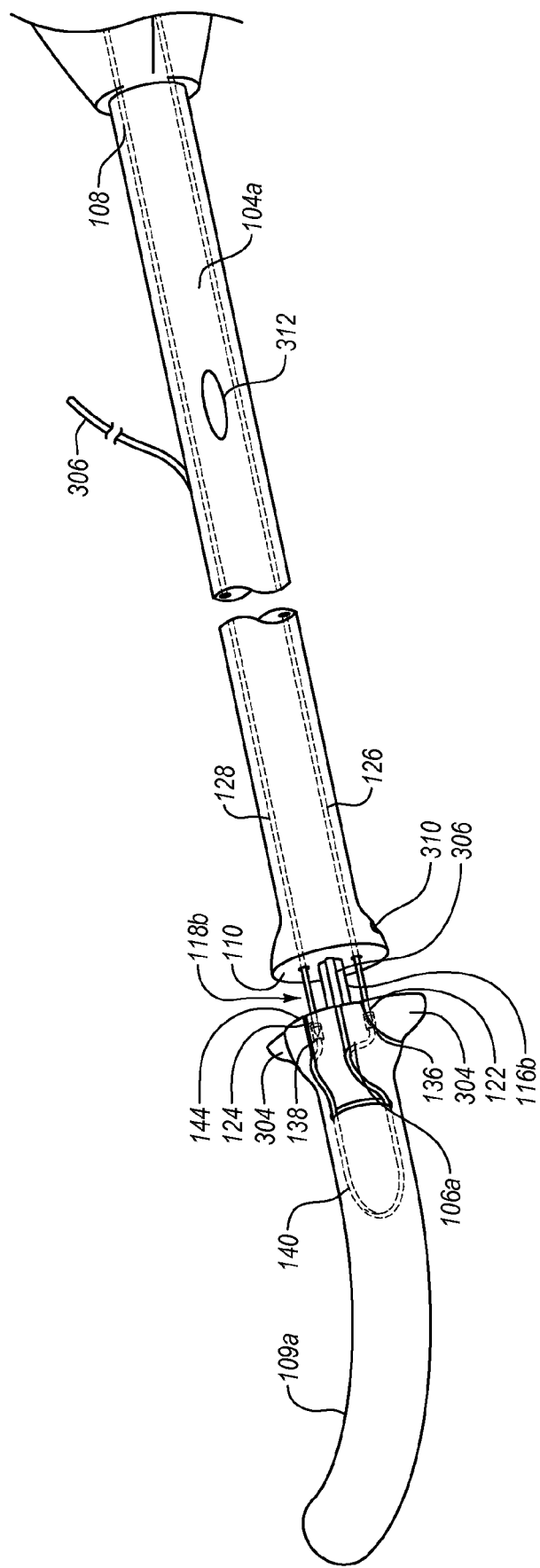
FIG. 11B illustrates an enlarged view of the shaft and articulating foot of the suturing device of FIG. 11A.
Figure 11C:
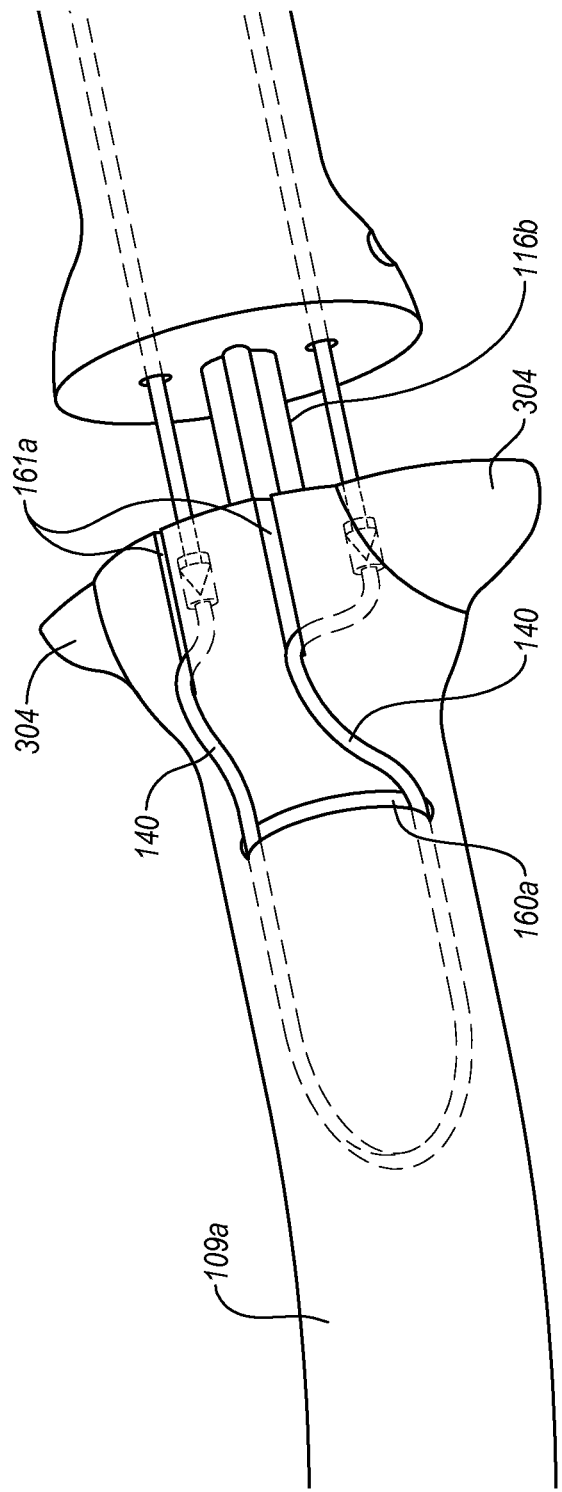
FIG. 11C illustrates a further enlarged view of the articulating foot of the suturing device of FIG. 11A.

As shown by FIGS. 11A-11B, by actuating the foot 106a into the deployed configuration, a tissue port 118b can be opened up between the foot 106a and the shaft 104a. As discussed previously, the tissue port 118b can receive tissue surrounding body lumen opening to be closed using the suturing device 300. As shown in FIGS. 11A-11B, when in the deployed configuration the foot actuator mechanism 302 can distally displace a spinal member 116b within the shaft 104a, thereby distally displacing the foot 106a secured, which may be secured to the spinal member 116b. Thus, the spinal member 116b can help define the tissue port 118b.

Figure 10A:
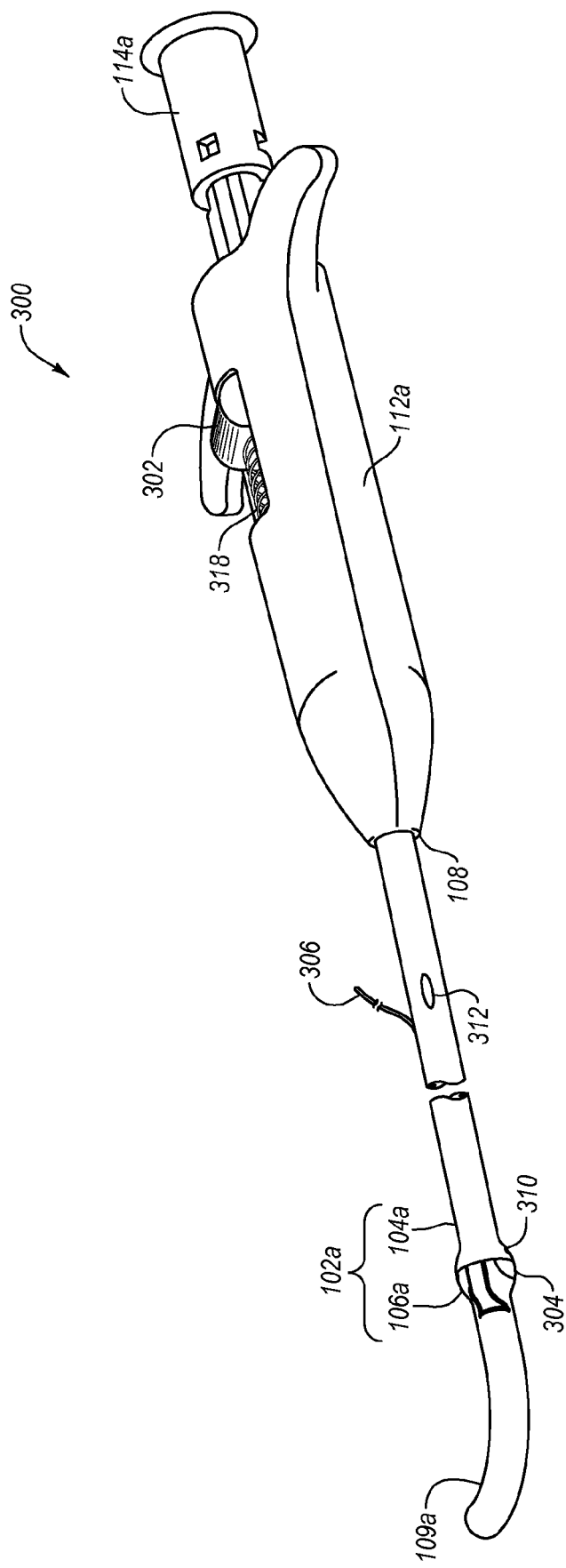
FIG. 10A illustrates a perspective view of a suturing device with an articulating foot in parked configuration in accordance with an implementation of the present invention.
Figure 10B:
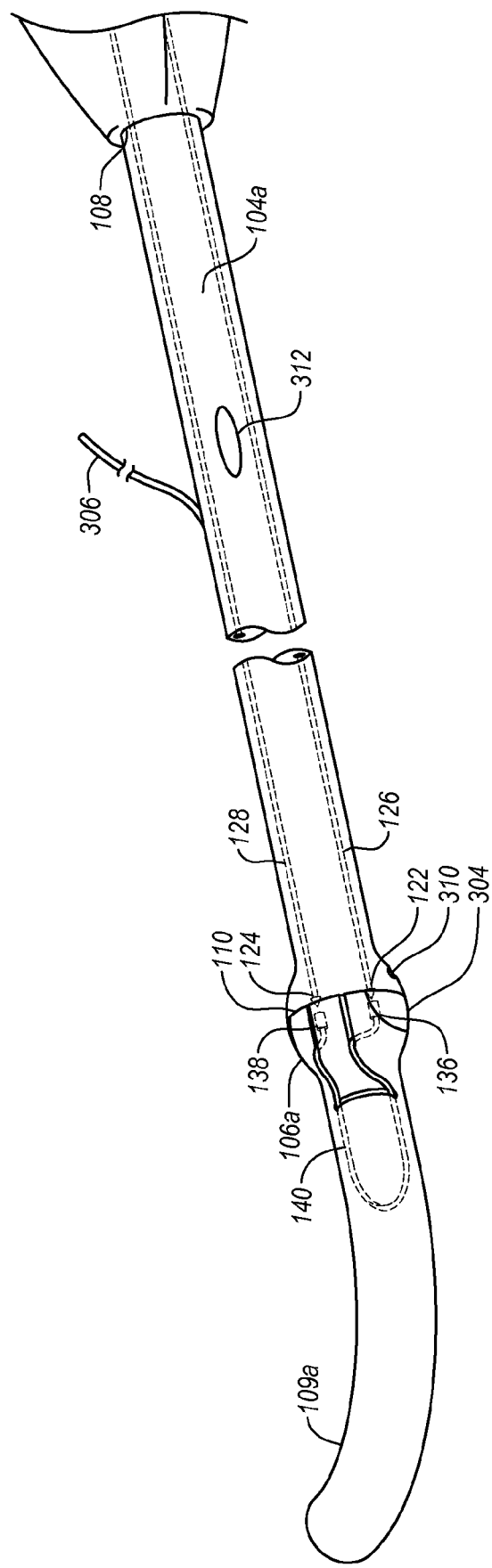
FIG. 10B illustrates an enlarged view of the shaft and articulating foot of the suturing device of FIG. 10A.

The foot actuator mechanism shown in FIGS. 10A and 11A comprises a tab 302 directly secured to the spinal member 116b. In such implementations, the foot actuator mechanism 302 can the medical practitioner with tactile feedback on how far the foot 106a has been deployed. In particular, in some implementations the distance the foot actuator mechanism 302 slides distally within the handle 112a can have a 1:1 ratio with respect to the distance the foot 106a separates from the distal end 110 of the shaft 104a. In alternative implementations, the distance the foot actuator mechanism 302 slides distally within the handle 112a can have a 2:1 ratio, a 3:1, a 4:1 ratio, or a greater ratio with the distance the foot 106a separates from the distal end 110 of the shaft 104a. In yet further implementations, the distance the foot actuator mechanism 302 slides distally within the handle 112a can have a 1:2 ratio, a 1:4 ratio, or a smaller ratio with respect to the distance the foot 106a separates from the distal end 110 of the shaft 104a.

A wide variety of foot actuation mechanisms can be employed to move the foot 106a between the first configuration (FIGS. 10A-10B) and the deployed configuration (FIGS. 11A-11B). The tab 302 illustrated in FIGS. 10A and 11A is only one example of such a mechanism. In additional implementations, the foot actuation mechanism can include a handle that pivots from a position generally perpendicular to the central axis of the handle 112a to a position generally parallel to the central axis of the handle 112a. In yet further implementations, the foot actuation mechanism can include a handle secured to the spinal member 116b that is positioned between the handle 112a and the needle actuation handle 114a. In such implementations, the medical practitioner can depress the foot actuation mechanism handle at least partially within the handle 112a to deploy the foot 106a. The medical practitioner can then depress the needle actuation handle 114a at least partially within the foot actuation mechanism handle to deploy the needles 122, 124.

In any event, once the foot 106a is deployed (FIGS. 11A-11B) the medical practitioner can proximally withdraw the foot 106a until it abuts against the inner wall of a body lumen to be closed. After which, the medical practitioner can compress the foot 106a and the shaft 104a together thereby urging or pushing tissue into the tissue port 118b. Thus, the articulating foot 106a can function to help ensure that tissue surrounding an opening to be closed is properly positioned within the tissue port 118b prior to deployment of the needles 122, 124.

In some implementations, the foot actuation mechanism 302 can be biased toward the first configuration (FIGS. 10A-10B). For example, FIG. 10A illustrates that the suturing device 300 can include a biasing member 318 configured to bias the foot actuation mechanism 318 toward the proximal end of the handle 112a. FIG. 10A illustrates that the biasing member 318 can comprise a leaf string. In alternative implementations, the biasing member 118 can include an elastomeric projection, or other structure that provides biasing characteristics similar to a spring, including, for example, a torsion spring, or a twin spring. One will appreciate in light of the disclosure herein that the biasing member 318 can cause the foot 106a to automatically move from the deployed configuration (FIGS. 10A-10B) toward the first configuration (FIGS. 11A-11B) upon release of the foot actuation mechanism 302. Thus, the biasing member 318 can cause the foot 106a to automatically capture tissue and urge the tissue into the tissue port 118b once the tissue location surface 144 is abutted against the inner wall of the body lumen, and the foot actuation mechanism 302 is released. In alternative implementations, the foot actuation mechanism 302 may not include a biasing member, and the actuation of the foot 106a can be a manual procedure performed by the medical practitioner.

In some implementations of the present invention, the suturing device 300 can include a locking mechanism configured to releasably lock the foot 106a in one or more configurations, such as, for example, the first or pre-deployed configuration, the deployed configuration, or a position between the first and deployed configurations. For instance, the locking mechanism can lock the foot 106a, and the foot actuation mechanism 302, in the deployed configuration (FIGS. 10A-10B) to ensure that the foot 106a is not compressed toward the shaft 104a, or vice versa, until the foot location surface 144 is positioned against the inner wall of a body lumen to be repaired. Alternatively or additionally, the locking mechanism can releasably lock the foot 106a in place relative to the shaft 104a once tissue has been captured in the tissue port 118b. This can help ensure that the foot 106a and the shaft 104a pinch or otherwise hold the tissue surrounding an opening to be repaired until the medical practitioner can deploy the needles 122, 124.

Figure 12A:
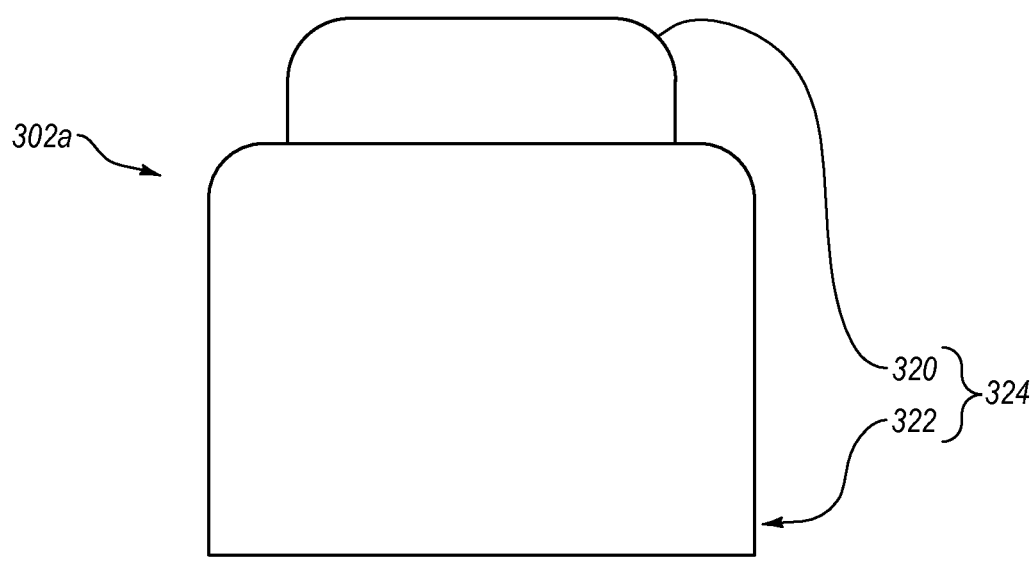
FIG. 12A illustrates an end view of a foot actuator mechanism with a locking mechanism for use in the suturing device of FIG. 10A in accordance with an implementation of the present invention.
Figure 12B:
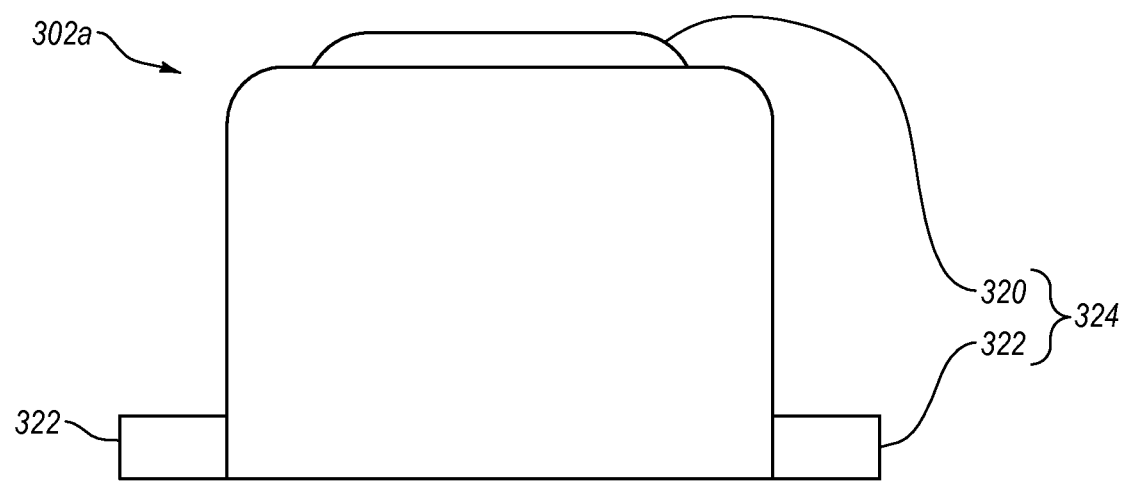
FIG. 12B illustrates the foot actuator mechanism and locking mechanism of FIG. 12A with the locking mechanism engaged.

For example, FIGS. 12A and 12B illustrate one implementation of a foot actuation mechanism that includes a locking mechanism 324. Specifically, FIGS. 12A and 12B illustrate that the locking mechanism 324 can include a button 320 and one or more protrusions 322. Specifically, in the illustrated implementation, the foot actuation mechanism 302a includes a button 320. When the button 320 is in the decompressed position shown in FIG. 12A, the foot actuation mechanism 302a, and the foot 116a, can freely move relative to the handle 112a and/or shaft 104a. Alternatively, when the button 320 is in the compressed position shown in FIG. 12B, one or more protrusions 322 may extend out from the foot actuation mechanism 302a. When extended, the one or more protrusions 322 may engage corresponding grooves (not shown) located within the handle 112a, thereby locking the foot actuation mechanism 302a and the foot 106a relative to the handle 112a and/or shaft 104a. Thus, the locking mechanism 324 can allow a medical practitioner to lock the foot 106a in one or more positions relative to the shaft 104a.

In order to release the locking mechanism 324, the medical practitioner can decompress the button 320, thereby withdrawing the one or more protrusions 322 into the foot actuation mechanism 302a. When in the decompressed position, the foot actuation mechanism 302a, and the foot 116a, can freely move relative to the handle 112a and/or shaft 104a.

In additional implementations, the suturing devices can include locking mechanisms having other configurations. For example, such locking mechanisms can include spring-loaded tabs (not shown) that extend into the housing 112a or shaft 104a from the foot actuation mechanism. Such spring-loaded tabs can prevent actuation of the foot 106a unless deactivated by compressing a button or other release mechanism similar to the button 320.

In some implementations of the present invention, the suturing device 300 can include both a biasing member 318 and a locking mechanism 324. Alternatively, the suturing device 300 can include one of a biasing member 318 and a locking mechanism 324, or neither a biasing member 318 or a locking mechanism 324. One will appreciate that the inclusion of the biasing member 318 and/or locking mechanism 324 can be based on a medical practitioner's preference.

Referring again to FIGS. 10A-11A, the suturing device can include a foot position indicator lumen 308 (FIGS. 13A-13I) that extends distally from a position port 310 to position indicator 312 located on the shaft 104a. When the foot 106a is properly positioned for deployment within a blood vessel or other body lumen (i.e., the tissue location surface 144 is completely within the body lumen), blood pressure can cause blood to flow into the position port 310, proximally through the indicator lumen 308 (FIGS. 13A-13I) to the position indicator 312.

As shown in FIGS. 10A-11B, the position indicator may optionally comprise a window 312 in which blood within the indicator lumen may be visible. In particular, FIGS. 10A-11B illustrate that the shaft 104a (or in alternative implementations the handle 112a) can include a clear window 312. In further implementations, the position indicator can comprise a length of the indicator lumen 308 that extends outside of the shaft 104a or handle 112a through which blood can flow out, indicating to the medical practitioner that the foot 106a is properly positioned. In yet further implementations, the position indicator can include electrical pressure sensors, electrolytic fluid detectors, or the like.

In additional implementations, the foot 106a or the distal portion of the shaft 104a can include a radiopaque material to increase visibility during placement. Optionally, the radiopaque material can be a layer or coating any portion of the foot 106a or shaft 104a. The radiopaque materials can be platinum, tungsten, silver, stainless steel, gold, tantalum, bismuth, barium sulfate, or a similar material.

It is further contemplated that the external surface and/or internal surface of the devices or members (e.g., exterior and luminal surfaces) as well as the entire body can be coated with another material having a composition different from the primary material. The use of a different material to coat the surfaces can be beneficial for imparting additional properties to the device or member, such as providing radiopaque characteristics, drug-reservoirs, and improved biocompatibility.

In one embodiment, at least one biocompatible polymeric layer can be a coating that is applied over the entire suturing device 300, or to select portions. Examples of such biocompatible polymeric materials can include a suitable hydrogel, hydrophilic polymer, hydrophobic polymer biodegradable polymers, bioabsorbable polymers, and monomers thereof. Examples of such polymers can include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like. Additionally, the coating can include hydrophilic and/or hydrophobic compounds, polypeptides, proteins, amino acids, polyethylene glycols, parylene, heparin, phosphorylcholine, or the like.

The coatings can also be provided on the suturing device 300 or portion thereof to facilitate the loading or delivery of beneficial agents or drugs, such as therapeutic agents, pharmaceuticals and radiation therapies. As such, the material and/or holes can be filled and/or coated with a biodegradable material.

FIGS. 10A-11A further illustrates that the suturing device 300 can include one or more balloons 304 secured to the foot 106a. The balloons 304 can be inflated by sending air or another fluid into a balloon lumen 306 extending from the shaft 104a into the foot 106a. Once inflated, the balloons 304 can effectively increase the surface area of the tissue location surface 144 and aid in locating the tissue surrounding an opening in a body lumen to be closed, as explained in greater detail below. One will appreciate that a medical practitioner can inflate the balloons 304 after receiving an indication from the position indicator 312 that the foot 106a is in a position ready for deployment. In particular, the balloons 304 can be inflated prior actuating the foot actuator mechanism 302 to deploy the foot 106a or after deploying the foot 106a.

In any case, the balloons 304 can help ensure that the foot 106a cannot be proximally withdrawn back through the body lumen when the foot 106a and shaft 104a are compressed together to draw tissue into the tissue port 118b. One will appreciate that the balloons 304 can provide the aforementioned functions without dilating or otherwise damaging the opening in the body lumen to be closed. In particular, because the balloons 304 can be deflated prior to passing the foot 106a distally or proximally through the body lumen, the balloons 304 can avoid damaging the tissue surround the opening of a body lumen to be closed.

FIGS. 13A-13I illustrate one implementation of a method of using the suturing device 300 to close an opening 210 in a body lumen 200. The method can include inserting the suturing device 300 in a distal direction into the body lumen 200. This can be accomplished with or without the use of a guidewire. FIGS. 13A-13I illustrate an example in which a guidewire 202 is used.

Figure 13A:
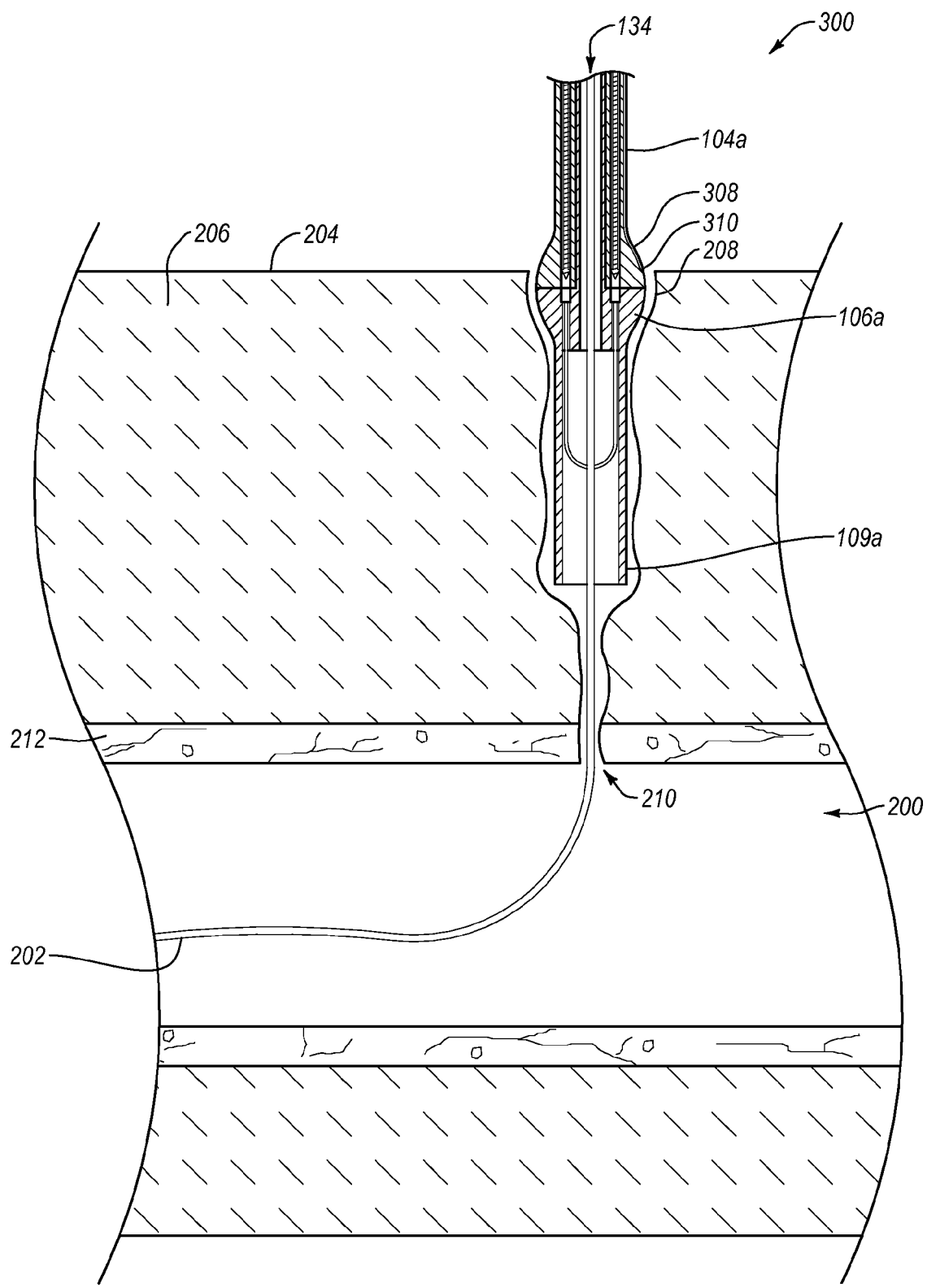
FIGS. 13A-13I illustrate cross-sectional views of a body lumen, showing a method for closing an opening in the wall of the body lumen using the suturing device of FIG. 10A.
Figure 13B:
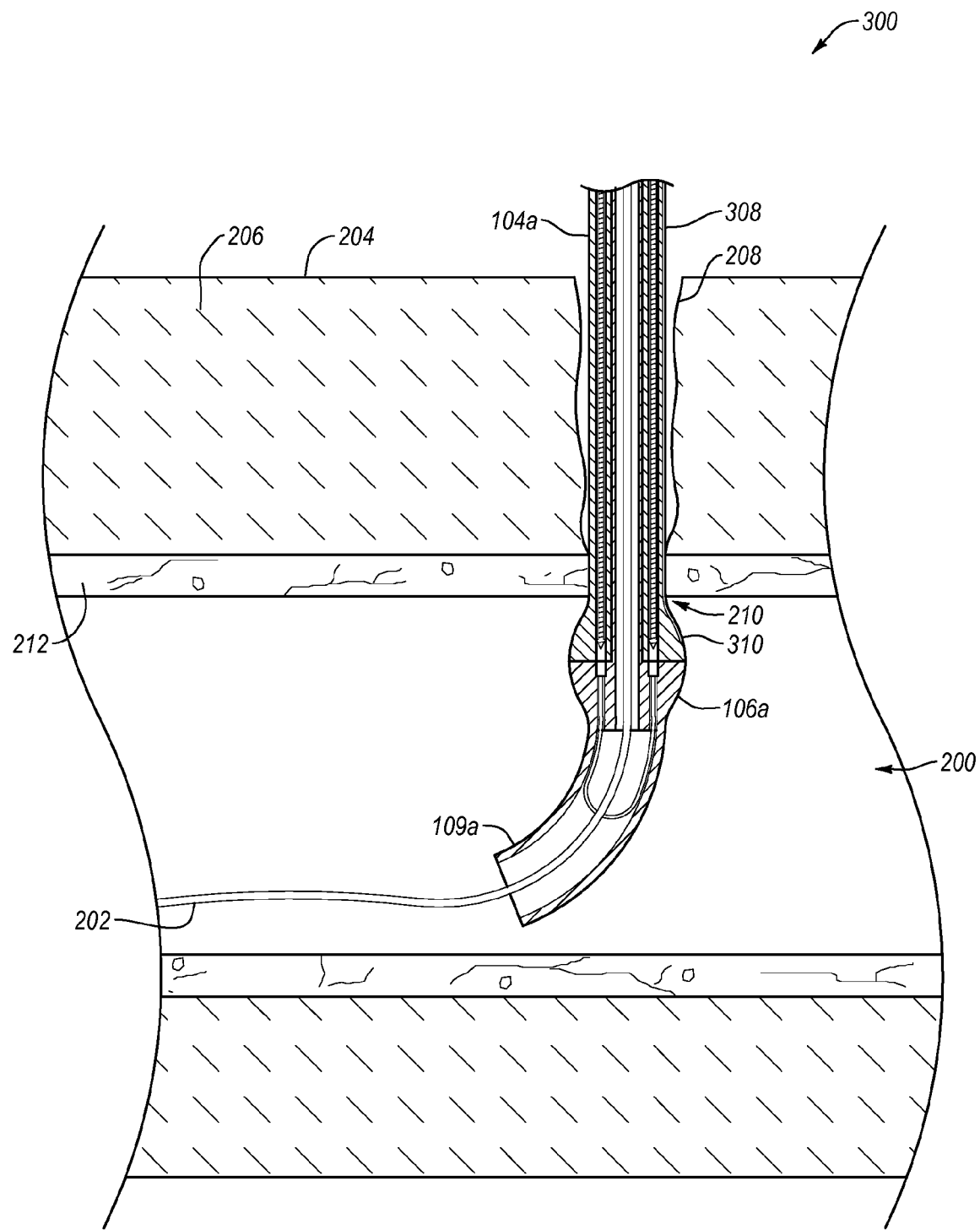

As shown by FIG. 13A, the guidewire 202 may enter the body lumen 200 through an opening or puncture site 210 formed in the body lumen wall 212. The guidewire 202 may extend along the body lumen 200. As illustrated by FIGS. 13A-13B, the flexible guidebody 109a and the guidewire lumen 134 can be advanced over the guidewire 202 in a monorail fashion, so that the guidewire 202 helps direct the suturing device 300 along the tissue tract 208 into the body lumen 200 through the opening 210.

As shown by FIGS. 13A-13B, the suturing device 300 can be slowly advanced until the position port 310 passes by the body lumen wall 212. Once past the body lumen wall 212, blood pressure can cause blood to flow into the position port 310, proximally through the indicator lumen 308 to the position indicator 312 (FIGS. 10A-11B). In alternative implementations, blood can pass out of the end of the indicator lumen 308, notifying the medical practitioner that the foot 106a is in a position within the body lumen 202, and is ready for deployment.

When the foot 106a is positioned within the body lumen 202, the medical practitioner can slide the foot actuation mechanism 302 distally along the handle 112a (FIGS. 10B and 11B), thereby causing the foot 106a to distally separate from the distal end 110 of the shaft 104a, as shown by FIG.

Figure 13C:
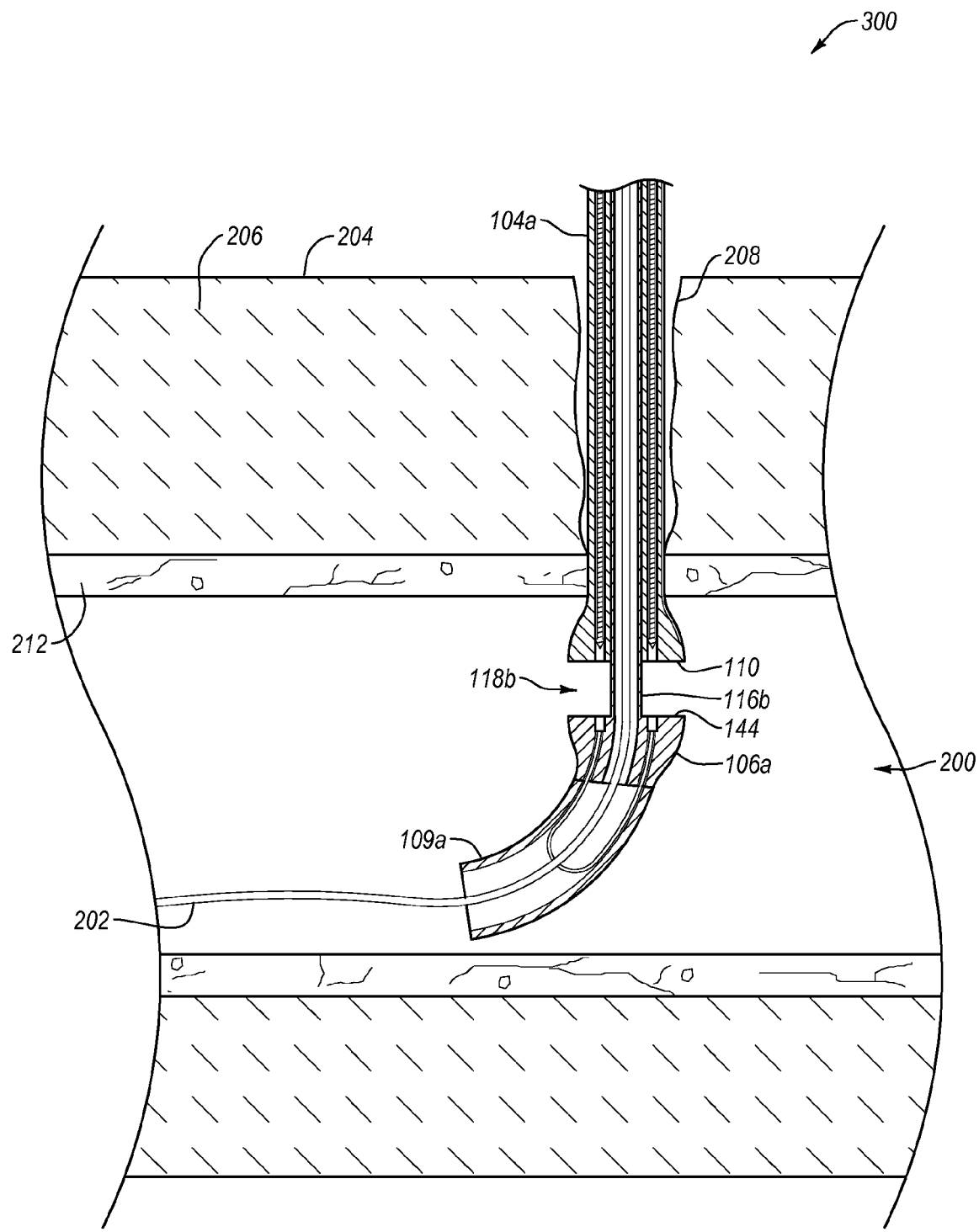

13C. In other words, the foot 106a can be articulated from a first configuration, in which the tissue location surface 144 of the foot 106a is abutted against the distal end 110 of the shaft 104a, to a deployed position, in which the tissue location surface 144 of the foot 106a is distally separated from the distal end 110 of the shaft 104a. As illustrated by FIG. 13C, by deploying the foot 106a, a tissue port 118b can be opened between the foot 106a and the shaft 104a. Once in the deployed position, the medical practitioner can compress a locking mechanism 324 (FIGS. 12A and 12B) to lock the foot 106a relative to the shaft 104a.

Figure 13D:
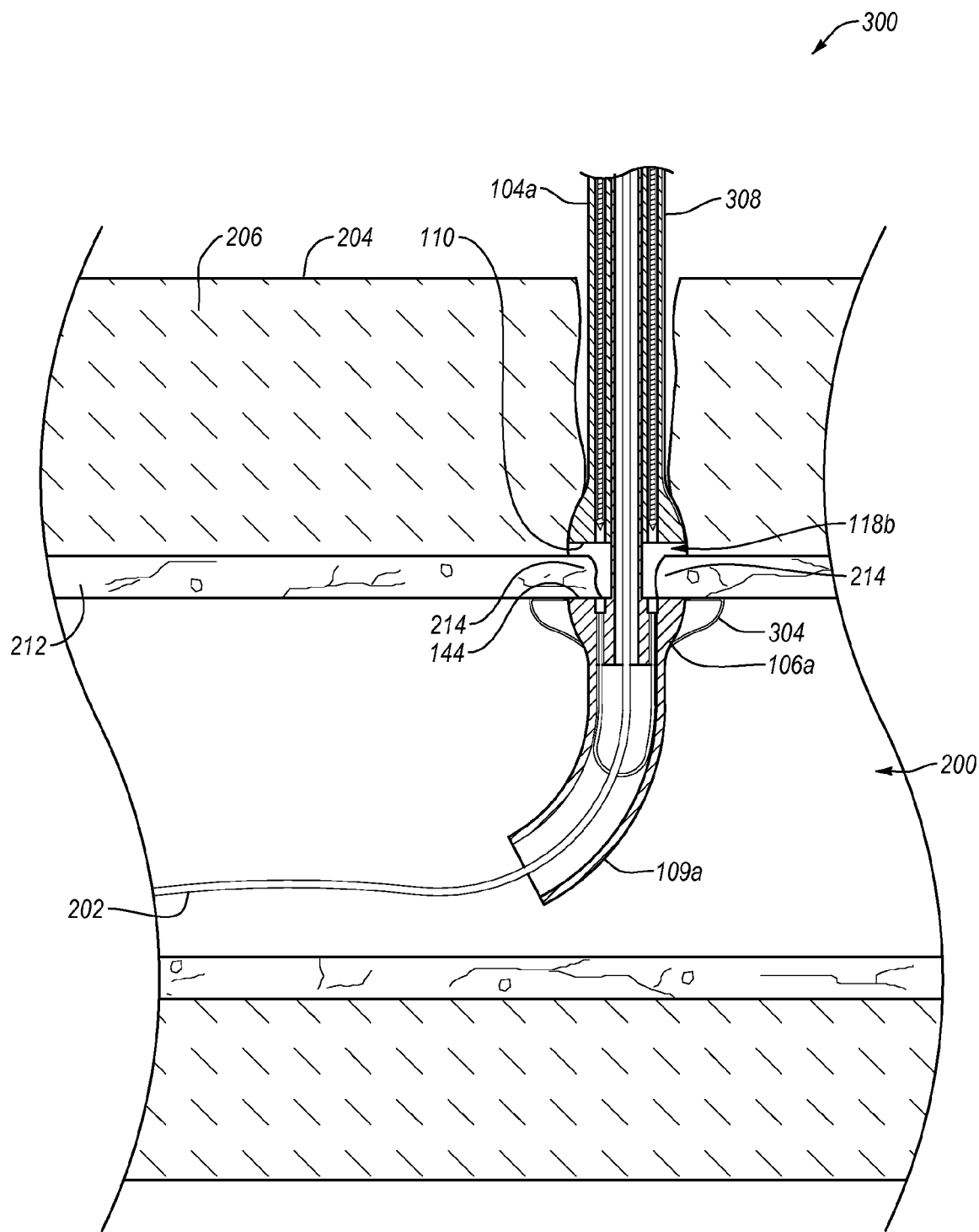

As shown by FIG. 13D, the medical practitioner can optionally inflate the one or more balloons 304. The balloons 304 can effectively increase the surface area of the tissue location surface 144 of the foot 106a. The medical practitioner can then slowly retract the suturing device 300 until resistance is felt when the tissue location surface 144 and/or the balloons 304 abut against the inner surface of the body lumen wall 212. By so doing, the distal end 110 of the shaft 104a can pass back through the opening 210 in the body lumen wall 212.

Figure 13E:
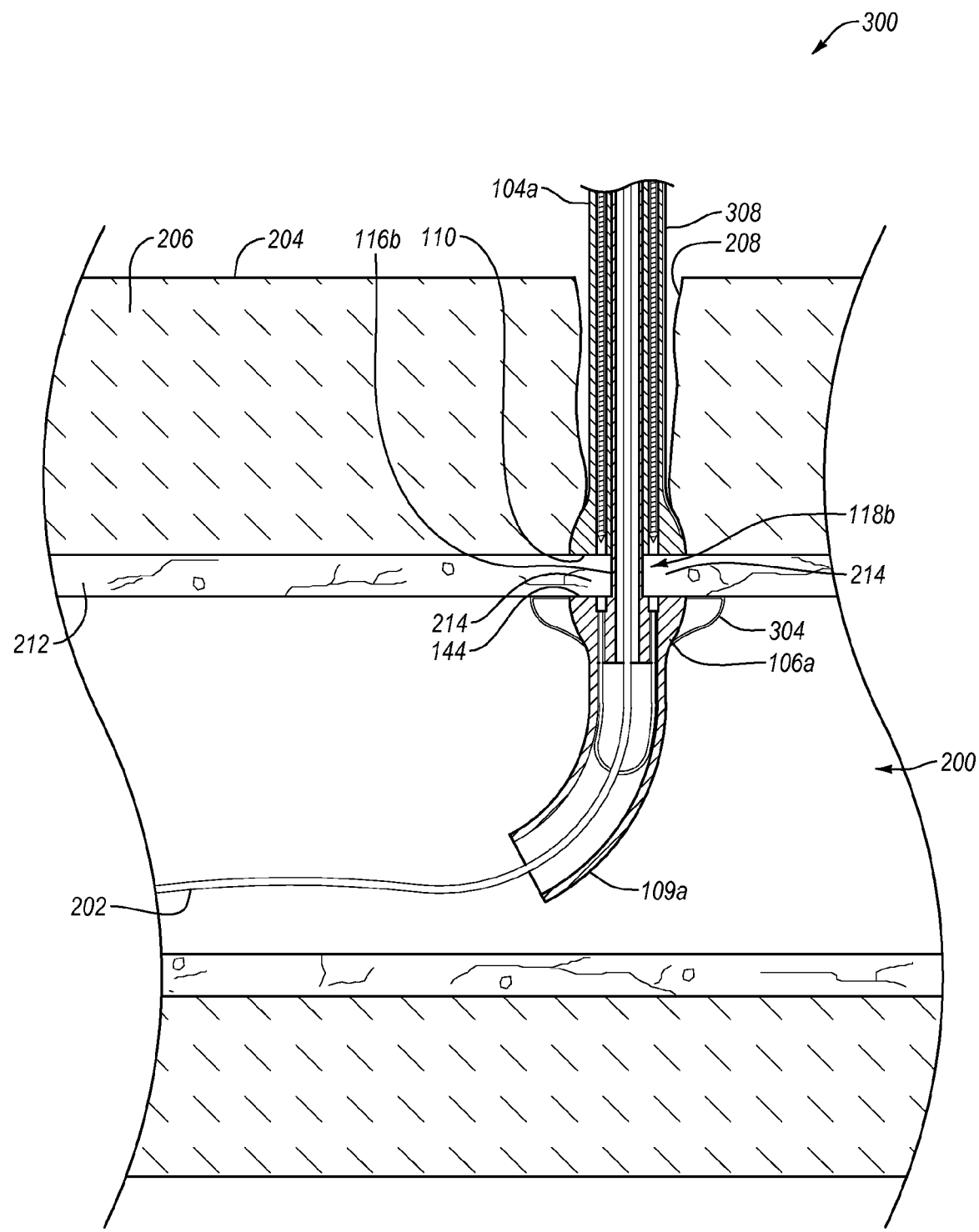

Once the shaft 104a is located on the proximal side of the body lumen wall 212, and the foot 106a is positioned on the distal side of the body lumen wall 212, the tissue 214 of the body lumen wall 212 adjacent the opening 210 can at least partially rebound or otherwise extend into the tissue port 118b, as shown by FIG. 13D. At this point, with the foot 106a locked in place, the medical practitioner can disengage the locking mechanism 324 (FIGS. 12A-12B). After the locking mechanism 324 is disengaged, the biasing member 318 (FIG. 10A), if included, can draw the shaft 104a and the foot 106a together. Otherwise, the medical practitioner can manually draw the shaft 104a and the foot 106a together using the foot actuation mechanism 302. The action of the foot 106a and the shaft 104a compressing toward each other can draw the tissue 214 further into the tissue port 118b, as depicted in FIG. 13E. In other words, the distal surface 110 of the shaft 104a and the tissue location surface 144 of the foot 106a can draw or push the tissue 214 into the tissue port 118b toward the spinal member 116b.

Figure 13F:
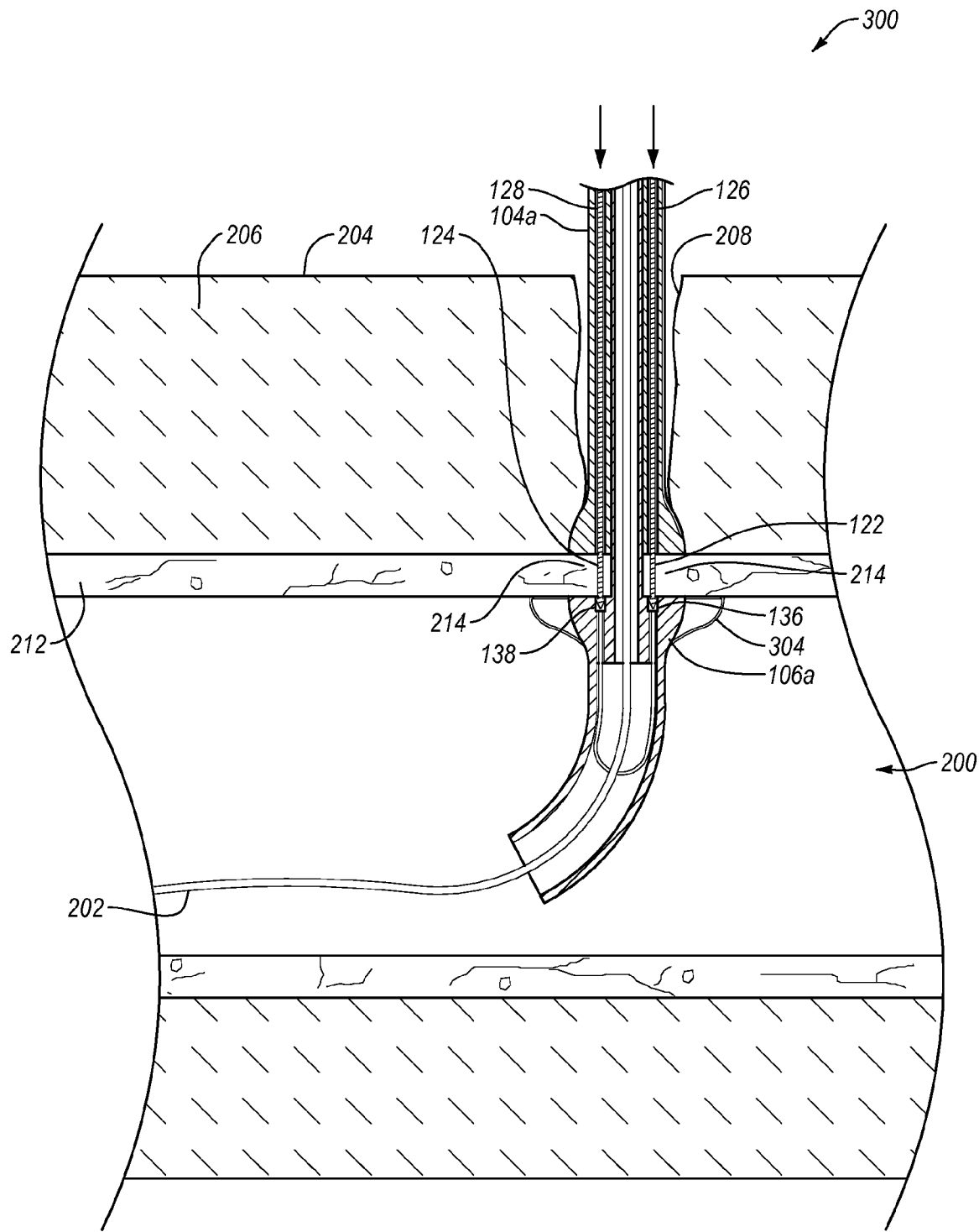

Next the medical practitioner can optionally lock the foot 106a in place relative to the shaft 104a using the locking mechanism 324 (FIGS. 12A and 12B). If the suturing device 300 includes a biasing member 318, the foot 106a may not be locked in place at this point. In any event, once the tissue 214 is positioned within the tissue port 118a, the needles 122, 124 can be deployed as shown in FIG. 13F. In particular, needles 122, 124 can be advanced in a distal direction within the needle lumens 126, 128, out of the needle exit openings 130, 132, distally across the tissue port 118a through the tissue 214, and into the needle capture devices 136, 138, as indicated by the arrows of FIG. 13F. This can be done by pushing the needle actuation handle 114a into the handle 112a (FIGS. 10A and 11A). The needles 122, 124 and needle capture devices 136, 138 can then be withdrawn out of the foot 106a, proximally across the tissue port 118b through the tissue 214, and out of the proximal end suturing device 300, as depicted by the arrows in FIG. 13G. One will appreciate that withdrawing the needles 122, 124 and needle capture devices 136, 138 can at least partially withdraw the proximal ends of the suture 140 from the foot 106a, allowing the ends of the suture 140 to be retrieved by the medical practitioner.

Figure 13G:
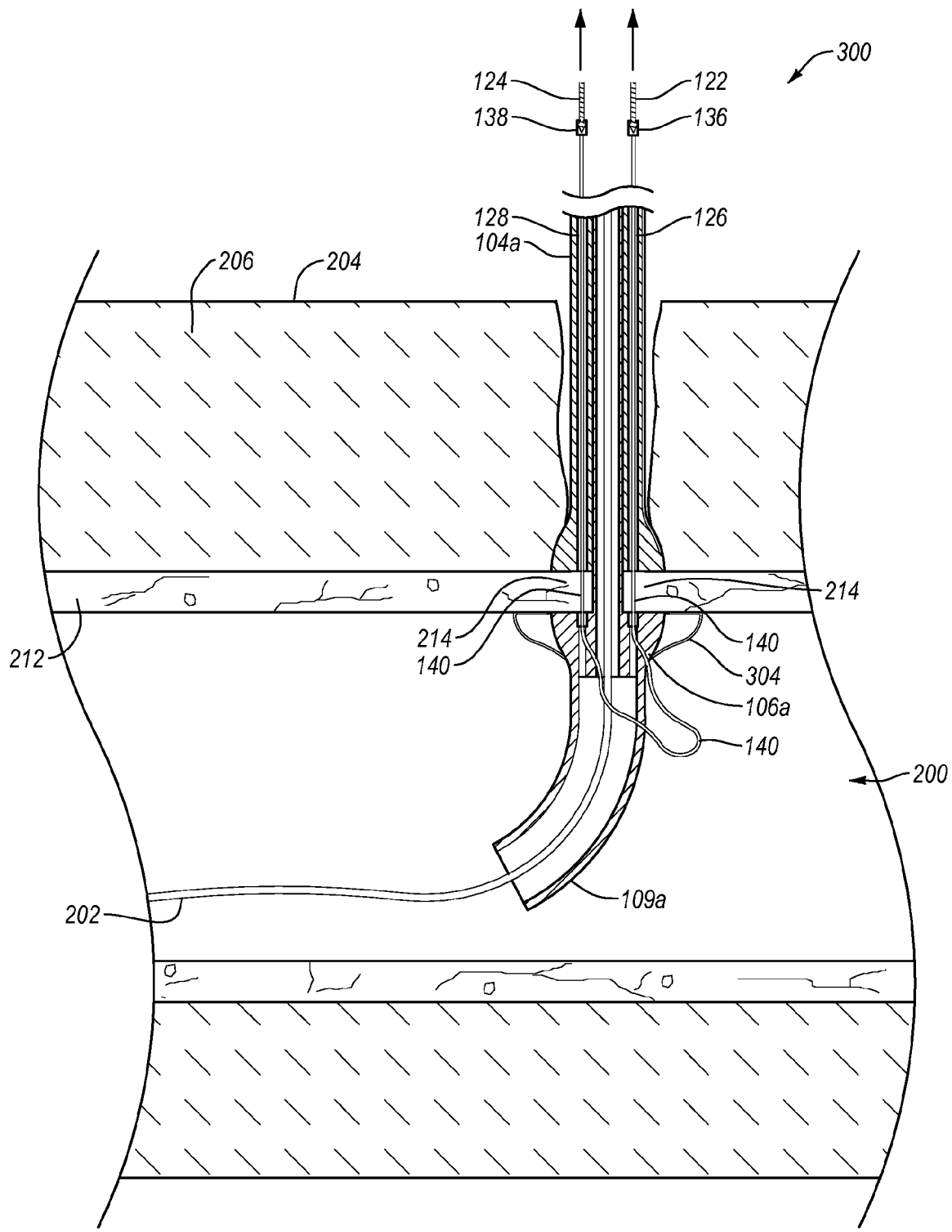

Furthermore, as shown by FIG. 13G, as the needles 122, 124, are withdrawn, the distal end of the suture 140 (i.e., the suture loop) can be pulled from the guidebody 109a and foot 106a via the suture exit slot 160a.

Figure 13H:
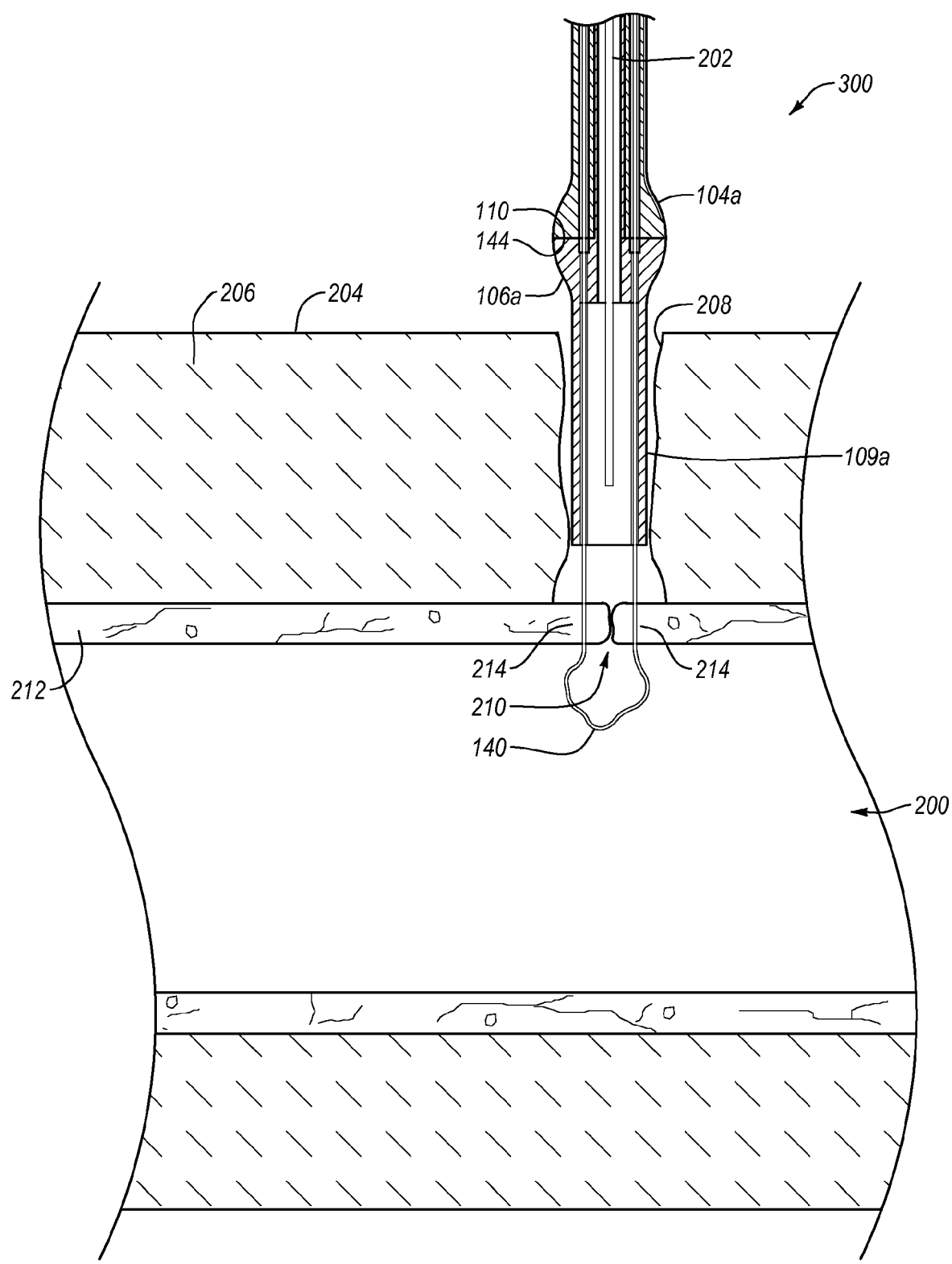
Figure 13I:
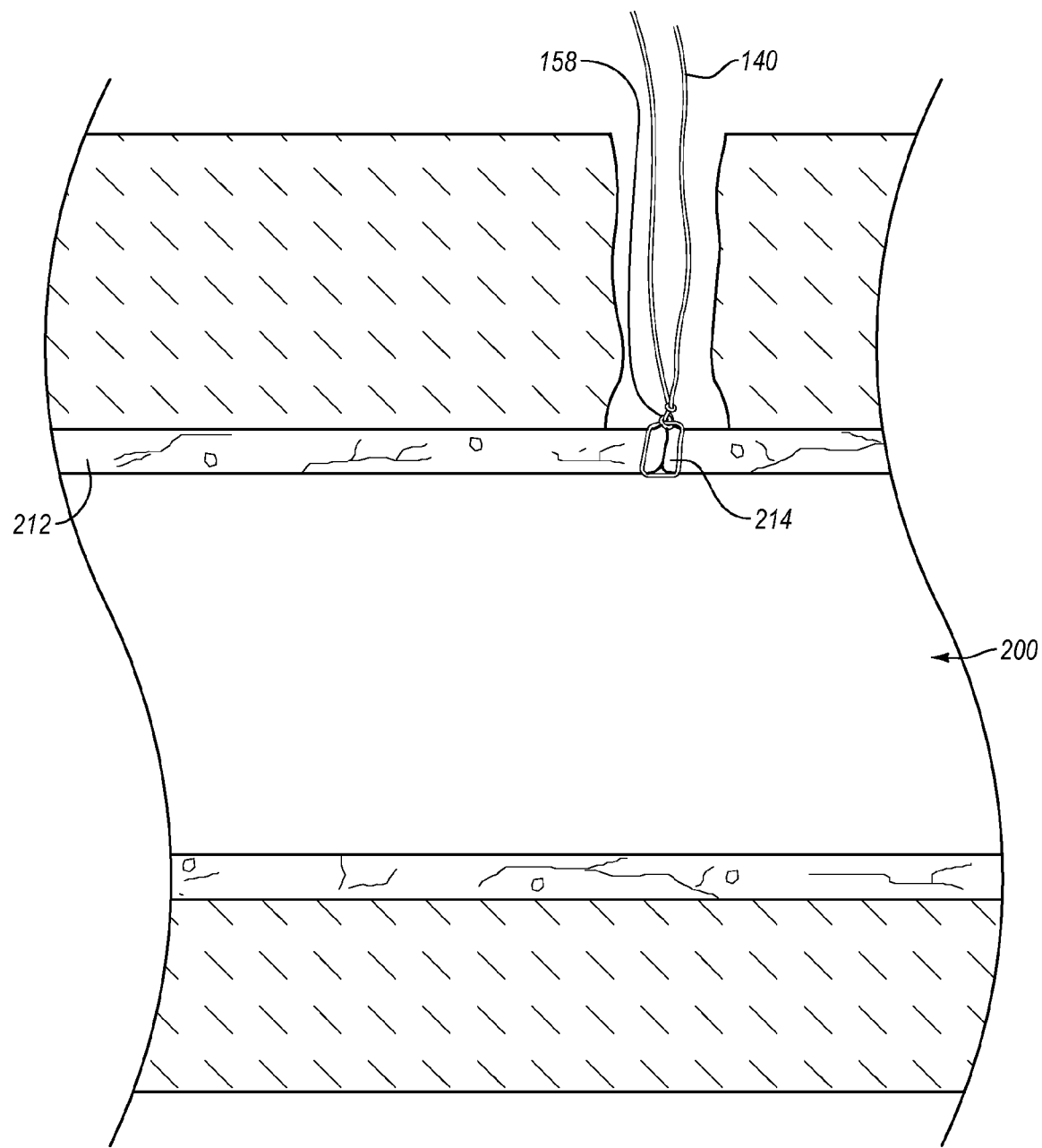

At this point, or before or after, if desired, the medical practitioner can withdraw the guidewire 202 from the body lumen 200 and the suturing device 300, as shown by FIG. 13H. FIG. 13H illustrates that the suturing device 300 can then be withdrawn from the body lumen 200 and out of the tissue tract 208. The medical practitioner can articulate the foot 106a from the deployed position to the first position using the foot actuation mechanism 302 either before or during the withdrawal of the suturing device 300. Once the suturing device 300 has been removed, the suture 140 can be employed to close the opening 210 in the body lumen 200, as shown by FIG. 13I. In particular, a surgical knot 158 can be tied thereby closing the opening in the body lumen 200.

The embodiments of the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. For example, the sutures described herein can further be prearranged to define a pre-tied knot, such as the pre-tied knots disclosed in U.S. Pat. No. 7,235,087 previously incorporated herein. Additionally, the suturing devices of the present invention can further include barbed sutures, or be used to deploy cleats or other devices to aid in closing a body lumen opening. Furthermore, where structures, elements, acts, steps, or stages have been described with reference to a specified implementation or device; each of the individual structures, elements, acts, steps, or stages, or a combination thereof, are contemplated to be combinable with each other and with other implementations and devices described herein. All changes which come within the meaning and range of equivalency of the claims are to be embraced within their scope.

What is claimed is:

1. A suturing device configured to close an opening in a body lumen, the suturing device comprising:
    a shaft having a distal end, a proximal end, and a guidewire lumen extending from the proximal end toward the distal end, the distal end of the shaft being defined by the distal most surface of the shaft;
    a first needle exit opening extending through the distal end of the shaft;
    a second needle exit opening extending through the distal end of the shaft;
    a foot member secured to the distal end of the shaft, the guidewire lumen extending from the shaft through the foot member, a proximal end of the foot member having a flared portion and a guide body portion extending distally of the flared portion, the flared portion extending radially outwardly of an outward surface of the shaft and an outward surface of the guide body;
    a first needle capture device removably secured to the foot member;
    a second needle capture device removably secured to the foot member; and
    at least one length of suture removably secured to the foot member, the at least one length of suture having a first end and a second end, the first end being secured to the first needle capture device and the second end being secured to the second needle capture device.

2. The suturing device of claim 1, further comprising at least one tissue port separating the first needle capture device from the first needle exit opening and the second needle capture device from the second needle exit opening, the at least one tissue port being configured to receive wall tissue of the body lumen.

3. The suturing device of claim 2, further comprising an actuator configured to move the foot member from a first configuration adjacent the distal end of the shaft to a deployed configuration distally separated from the distal end of the shaft, thereby opening the at least one tissue port.

4. The suturing device of claim 2, further comprising a pair of needles configured to be advanced from through the shaft, out of the first and second needle exit openings, across the at least one tissue port, and into the first and second needle capture devices.

5. The suturing device of claim 1, further comprising a spinal member connecting the foot member to the shaft.

6. A suturing device, configured to close an opening in a body lumen, the suturing device comprising:
- a shaft having a distal end, a proximal end, and a guidewire lumen extending from the proximal end toward the distal end, the distal end of the shaft being defined by the distal most surface of the shaft;
- a first needle exit opening extending through the distal end of the shaft;
- a second needle exit opening extending through the distal end of the shaft;
- a foot member secured to the distal end of the shaft, the guidewire lumen extending from the shaft through the foot member;
- a first needle capture device removably secured to the foot member;
- a second needle capture device removably secured to the foot member; and at least one length of suture removably secured to the foot member within a suture lumen, the at least one length of suture having a first end and a second end, the first end being secured to the first needle capture device and the second end being secured to the second needle capture device, the suture lumen extending at least partially around the guidewire lumen,
- wherein the suture lumen receives the entire length of the at least one length of suture.

7. The suturing device of claim 6, further comprising at least one tissue port separating the first needle capture device from the first needle exit opening and the second needle capture device from the second needle exit opening, the at least one tissue port being configured to receive wall tissue of the body lumen.

8. The suturing device of claim 7, further comprising a pair of needles configured to be advanced from through the shaft, out of the first and second needle exit openings, across the at least one tissue port, and into the first and second needle capture devices.

9. The suturing device of claim 6, further comprising a spinal member connecting the foot member to the shaft.

10. The suturing device of claim 9, wherein the spinal member comprises a width equal to about a diameter of a guide body portion of the foot member.

11. The suturing device of claim 9, further comprising a pair of tissue ports disposed between the shaft and the foot member at the spinal member.

12. The suturing device of claim 9, wherein the spinal member forms a single circumferential tissue port.

13. The suturing device of claim 6, wherein the suture lumen extends 180 degrees around the guidewire lumen.

14. The suturing device of claim 6, further comprising a handle.

15. A suturing device, configured to close an opening in a body lumen, the suturing device comprising:
- a shaft having a distal end, a proximal end, and a guidewire lumen extending from the proximal end toward the distal end, the distal end of the shaft being defined by the distal most surface of the shaft;
- a first needle exit opening extending through the distal end of the shaft;
- a second needle exit opening extending through the distal end of the shaft;
- a foot member secured to the distal end of the shaft, the guidewire lumen extending from the shaft through the foot member, the foot includes a flared portion and a guide body portion, the flared portion extending outwardly greater than the guide body portion and the shaft;
- a first needle capture device removably secured to the foot member;
- a second needle capture device removably secured to the foot member; and
- at least one length of suture removably secured to the foot member within a suture lumen, the at least one length of suture having a first end and a second end, the first end being secured to the first needle capture device and the second end being secured to the second needle capture device, the suture lumen extending at least partially around the guidewire lumen.

16. The suturing device of claim 15, further comprising a needle actuation handle selectively engageable with the shaft.

17. The suturing device of claim 16, wherein the needle actuation handle is secured to a first needle and a second needle.

18. The suturing device of claim 16, wherein the shaft comprises a receptacle disposed at the proximal end of the shaft, the needle actuation handle being configured to be received within the receptacle.

* * * * *